(12) United States Patent
Bornheimer et al.

(10) Patent No.: US 10,663,476 B2
(45) Date of Patent: May 26, 2020

(54) OPTICAL IMAGING SYSTEM AND METHODS FOR USING THE SAME

(71) Applicant: Becton, Dickinson and Company, Franklin Lakes, NJ (US)

(72) Inventors: Scott Bornheimer, Berkeley, CA (US); Edward Goldberg, Los Gatos, CA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 129 days.

(21) Appl. No.: 15/993,503

(22) Filed: May 30, 2018

(65) Prior Publication Data
US 2019/0004067 A1    Jan. 3, 2019

Related U.S. Application Data

(62) Division of application No. 14/537,769, filed on Nov. 10, 2014, now Pat. No. 10,018,640.

(Continued)

(51) Int. Cl.
*G01N 33/72* (2006.01)
*G01N 21/31* (2006.01)
(Continued)

(52) U.S. Cl.
CPC .......... *G01N 33/721* (2013.01); *G01J 3/0208* (2013.01); *G01J 3/04* (2013.01); *G01J 3/42* (2013.01); *G01N 21/31* (2013.01); *G01N 21/6428* (2013.01); *G01N 21/359* (2013.01); *G01N 21/6408* (2013.01); *G01N 21/6445* (2013.01); *G01N 2021/0346* (2013.01); *G01N 2021/6439* (2013.01); *G01N 2021/6491* (2013.01); *G01N 2201/062* (2013.01)

(58) Field of Classification Search
None
See application file for complete search history.

(56) References Cited

U.S. PATENT DOCUMENTS

| 816,135 A | 3/1906 | Stroud |
|---|---|---|
| 3,819,913 A | 6/1974 | Carter et al. |

(Continued)

FOREIGN PATENT DOCUMENTS

| DE | 102009016712 | 10/2010 |
|---|---|---|
| EP | 0682245 A1 | 11/1995 |

(Continued)

OTHER PUBLICATIONS

Beach, J. M. "A LED light calibration source for dual-wavelength microscopy," Cell Calcium, 21 (1 ): 63-68 (1997).

(Continued)

*Primary Examiner* — Xiaoyun R Xu
(74) *Attorney, Agent, or Firm* — Peter W. Schroen; Bret E. Field; Bozicevic, Field & Francis LLP

(57) ABSTRACT

Aspects of the present disclosure include methods and systems for assaying a sample for an analyte. Methods according to certain embodiments include illuminating a sample with a slit-shaped beam of light, detecting light transmitted through the sample, determining absorbance of the transmitted light at one or more wavelengths and calculating concentration of the analyte based on the absorbance to assay the sample for the analyte. Systems for practicing the subject methods are also described.

19 Claims, 13 Drawing Sheets

Related U.S. Application Data

(60) Provisional application No. 61/903,804, filed on Nov. 13, 2013, provisional application No. 61/949,833, filed on Mar. 7, 2014.

(51) Int. Cl.
  *G01J 3/02* (2006.01)
  *G01J 3/04* (2006.01)
  *G01N 21/64* (2006.01)
  *G01J 3/42* (2006.01)
  *G01N 21/359* (2014.01)
  *G01N 21/03* (2006.01)

(56) References Cited

U.S. PATENT DOCUMENTS

| | | |
|---|---|---|
| 3,916,205 A | 10/1975 | Kleinerman |
| 3,963,350 A | 6/1976 | Watanabe et al. |
| 4,088,448 A | 5/1978 | Lilja et al. |
| 4,125,828 A | 11/1978 | Resnick et al. |
| 4,133,873 A | 1/1979 | Noller |
| 4,337,222 A | 6/1982 | Kitajima et al. |
| 4,501,496 A | 2/1985 | Griffin |
| 4,586,190 A | 4/1986 | Tsuji |
| 4,727,020 A | 2/1988 | Recktenwald |
| 4,751,188 A | 6/1988 | Valet |
| 4,857,735 A | 8/1989 | Noller |
| 4,959,305 A | 9/1990 | Woodrum |
| 5,053,626 A | 10/1991 | Tillotson |
| 5,073,857 A | 12/1991 | Peters et al. |
| 5,102,625 A | 4/1992 | Milo |
| 5,134,662 A | 7/1992 | Bacus et al. |
| 5,159,642 A | 10/1992 | Kosaka |
| 5,187,749 A | 2/1993 | Sugimoto |
| 5,196,709 A | 3/1993 | Berndt |
| 5,200,152 A | 4/1993 | Brown |
| 5,294,799 A | 3/1994 | Aslund et al. |
| 5,332,905 A | 7/1994 | Brooker et al. |
| 5,348,859 A | 9/1994 | Brunhouse et al. |
| 5,385,539 A | 1/1995 | Maynard |
| 5,489,771 A | 2/1996 | Beach et al. |
| 5,491,343 A | 2/1996 | Brooker |
| 5,528,045 A | 6/1996 | Hoffman et al. |
| 5,547,849 A | 8/1996 | Baer et al. |
| 5,554,536 A | 9/1996 | Rising |
| 5,556,764 A | 9/1996 | Sizto et al. |
| 5,592,291 A | 1/1997 | Iida |
| 5,599,668 A | 2/1997 | Stimpson et al. |
| 5,627,037 A | 5/1997 | Ward et al. |
| 5,661,558 A | 8/1997 | Nogami et al. |
| 5,674,457 A | 10/1997 | Williamsson et al. |
| 5,675,155 A | 10/1997 | Pentoney et al. |
| 5,681,529 A | 10/1997 | Taguchi et al. |
| 5,692,503 A | 12/1997 | Kuenstner |
| 5,732,150 A | 3/1998 | Zhou et al. |
| 5,733,721 A | 3/1998 | Hemstreet et al. |
| 5,773,301 A | 6/1998 | Ziegler |
| 5,851,835 A | 12/1998 | Groner |
| 5,898,487 A | 4/1999 | Hage |
| 6,043,880 A | 3/2000 | Andrews et al. |
| 6,064,474 A | 5/2000 | Lee et al. |
| 6,064,897 A | 5/2000 | Lindberg et al. |
| 6,094,592 A | 7/2000 | Yorkey et al. |
| 6,103,197 A | 8/2000 | Werner |
| 6,154,282 A | 11/2000 | Lilge et al. |
| 6,159,740 A | 12/2000 | Hudson et al. |
| 6,181,418 B1 | 1/2001 | Palumbo et al. |
| 6,187,592 B1 | 2/2001 | Gourley |
| 6,214,629 B1 | 4/2001 | Freitag et al. |
| 6,226,347 B1 | 5/2001 | Golenhofen |
| 6,262,798 B1 | 7/2001 | Shepherd et al. |
| 6,294,094 B1 | 9/2001 | Muller et al. |
| 6,305,804 B1 | 10/2001 | Rice et al. |
| 6,342,376 B1 | 1/2002 | Kozian et al. |
| 6,345,191 B1 | 2/2002 | Hartmann et al. |
| 6,350,613 B1 | 2/2002 | Wardlaw et al. |
| 6,410,341 B1 | 6/2002 | Freitag et al. |
| 6,453,060 B1 | 9/2002 | Riley et al. |
| 6,477,394 B2 | 11/2002 | Rice et al. |
| 6,479,299 B1 | 11/2002 | Parce et al. |
| 6,493,567 B1 | 12/2002 | Krivitski et al. |
| 6,519,025 B2 | 2/2003 | Shepherd et al. |
| 6,563,585 B1 | 5/2003 | Rao et al. |
| 6,594,075 B1 | 7/2003 | Kanao |
| 6,611,320 B1 | 8/2003 | Lindberg et al. |
| 6,612,111 B1 | 9/2003 | Hodges |
| 6,638,769 B2 | 10/2003 | Lilja et al. |
| 6,665,060 B1 | 12/2003 | Zahniser et al. |
| 6,696,240 B1 | 2/2004 | Kloepfer et al. |
| 6,716,588 B2 | 4/2004 | Sammak et al. |
| 6,723,290 B1 | 4/2004 | Wardlaw |
| 6,740,527 B1 | 5/2004 | Wong et al. |
| 6,825,921 B1 | 11/2004 | Modlin et al. |
| 6,828,567 B2 | 12/2004 | Amirkhanian et al. |
| 6,831,733 B2 | 12/2004 | Pettersson et al. |
| 6,858,400 B2 | 2/2005 | Bristow |
| 6,862,534 B2 | 3/2005 | Sterling et al. |
| 6,869,570 B2 | 3/2005 | Wardlaw |
| 6,898,458 B2 | 5/2005 | Zeng et al. |
| 6,960,165 B2 | 11/2005 | Ueno et al. |
| 6,985,224 B2 | 1/2006 | Hart |
| 6,999,173 B2 | 2/2006 | Kleinfeld et al. |
| 7,075,628 B2 | 7/2006 | Shepherd et al. |
| 7,094,562 B2 | 8/2006 | Bittner |
| 7,096,124 B2 | 8/2006 | Sterling et al. |
| 7,115,841 B2 | 10/2006 | Zeng et al. |
| 7,133,545 B2 | 11/2006 | Douglass et al. |
| 7,146,372 B2 | 12/2006 | Bacus et al. |
| 7,149,332 B2 | 12/2006 | Bacus et al. |
| 7,271,912 B2 | 9/2007 | Sterling et al. |
| 7,279,134 B2 | 10/2007 | Chan et al. |
| 7,303,922 B2 | 12/2007 | Jeng et al. |
| 7,319,894 B2 | 1/2008 | Higgins |
| 7,324,674 B2 | 1/2008 | Ozawa et al. |
| 7,420,660 B2 | 9/2008 | Muller et al. |
| 7,426,407 B2 | 9/2008 | Higgins |
| 7,477,382 B2 | 1/2009 | Grey et al. |
| 7,515,268 B1 | 4/2009 | Ayliffe et al. |
| 7,518,727 B2 | 4/2009 | Pentoney et al. |
| 7,539,335 B2 | 5/2009 | Fukuyama |
| 7,560,073 B1 | 7/2009 | Peter et al. |
| 7,625,712 B2 | 12/2009 | Paul et al. |
| 7,630,063 B2 | 12/2009 | Padmanabhan et al. |
| 7,674,598 B2 | 3/2010 | Paul et al. |
| 7,738,094 B2 | 6/2010 | Goldberg |
| 7,762,946 B2 | 7/2010 | Sugimoto |
| 7,781,226 B2 | 8/2010 | Mcdevitt et al. |
| 7,790,464 B2 | 9/2010 | Tarasev |
| 7,826,728 B2 | 11/2010 | Konno et al. |
| 7,854,891 B2 | 12/2010 | Yamamoto et al. |
| 7,892,551 B2 | 2/2011 | Glencross |
| 7,903,241 B2 | 3/2011 | Wardlaw et al. |
| 7,952,692 B2 | 5/2011 | Primack et al. |
| 8,009,894 B2 | 8/2011 | Lindberg et al. |
| 8,125,623 B2 | 2/2012 | Munger et al. |
| 8,224,058 B2 | 7/2012 | Lindberg et al. |
| 8,244,021 B2 | 8/2012 | Lett et al. |
| 8,306,594 B2 | 11/2012 | Paseman et al. |
| 8,353,848 B2 | 1/2013 | Long et al. |
| 8,377,398 B2 | 2/2013 | Mcdevitt et al. |
| 8,406,859 B2 | 3/2013 | Zuzak et al. |
| 8,483,789 B2 | 7/2013 | Higgins |
| 8,488,903 B2 | 7/2013 | Higuchi |
| 8,541,227 B2 | 9/2013 | Christensen et al. |
| 2003/0152927 A1 | 8/2003 | Jakobsen et al. |
| 2003/0170613 A1 | 9/2003 | Straus |
| 2003/0175947 A1 | 9/2003 | Liu et al. |
| 2003/0230728 A1 | 12/2003 | Dai et al. |
| 2004/0115831 A1 | 6/2004 | Meathrel et al. |
| 2004/0125370 A1 | 7/2004 | Montagu |
| 2004/0189311 A1 | 9/2004 | Glezer et al. |
| 2004/0191124 A1 | 9/2004 | Noetzel et al. |
| 2004/0224329 A1 | 11/2004 | Gjerde et al. |
| 2005/0142565 A1 | 6/2005 | Samper et al. |

(56) References Cited

U.S. PATENT DOCUMENTS

| | | |
|---|---|---|
| 2005/0190058 A1 | 9/2005 | Call |
| 2006/0024756 A1 | 2/2006 | Tibbe et al. |
| 2006/0183236 A1 | 8/2006 | Berlin |
| 2006/0227325 A1 | 10/2006 | Rulison |
| 2006/0241495 A1 | 10/2006 | Kurtz |
| 2006/0252079 A1 | 11/2006 | Oldham et al. |
| 2007/0132994 A1 | 6/2007 | Kobayashi et al. |
| 2007/0178009 A1 | 8/2007 | Sakaino et al. |
| 2007/0259436 A1 | 11/2007 | Tarasev |
| 2008/0190220 A1 | 8/2008 | Backes et al. |
| 2008/0203319 A1 | 8/2008 | Pentoney et al. |
| 2008/0268469 A1 | 10/2008 | Srienc et al. |
| 2009/0038417 A1 | 2/2009 | Lee |
| 2009/0075324 A1 | 3/2009 | Pettersson |
| 2009/0181411 A1 | 7/2009 | Battrell et al. |
| 2009/0317806 A1 | 12/2009 | Hasson |
| 2010/0170789 A1 | 7/2010 | Mieda et al. |
| 2010/0291599 A1 | 11/2010 | Tague, Jr. et al. |
| 2011/0102768 A1 | 5/2011 | Dosmann et al. |
| 2011/0118139 A1 | 5/2011 | Mehta et al. |
| 2012/0040470 A1 | 2/2012 | Dorn et al. |
| 2012/0194805 A1 | 8/2012 | Ness et al. |
| 2012/0223260 A1 | 9/2012 | Hansen et al. |
| 2013/0041236 A1 | 2/2013 | Pugia et al. |
| 2013/0045529 A1 | 2/2013 | Goldberg et al. |
| 2013/0162990 A1 | 6/2013 | Kobayashi et al. |
| 2014/0200154 A1 | 7/2014 | Sugarman et al. |
| 2015/0125882 A1 | 5/2015 | Bornheimer et al. |

FOREIGN PATENT DOCUMENTS

| | | |
|---|---|---|
| EP | 0737855 A1 | 10/1996 |
| EP | 0788615 A1 | 8/1997 |
| EP | 0818682 | 1/1998 |
| EP | 0821784 B1 | 11/1998 |
| EP | 0959346 | 11/1999 |
| EP | 0663070 B1 | 5/2000 |
| EP | 0681177 | 7/2000 |
| EP | 0744600 | 8/2001 |
| EP | 0809807 B1 | 7/2002 |
| EP | 0800074 | 7/2003 |
| EP | 0969279 B1 | 10/2003 |
| EP | 1347702 | 10/2003 |
| EP | 1456649 B1 | 7/2006 |
| EP | 1701150 A1 | 9/2006 |
| EP | 1324021 B1 | 1/2008 |
| EP | 1924195 A2 | 5/2008 |
| EP | 1990638 A1 | 11/2008 |
| EP | 2041549 | 4/2009 |
| EP | 2083687 A1 | 8/2009 |
| EP | 1405073 B1 | 3/2010 |
| EP | 2232442 | 9/2010 |
| EP | 1698883 B1 | 1/2011 |
| EP | 2016390 B1 | 4/2013 |
| EP | 2605020 | 6/2013 |
| EP | 1558934 B1 | 7/2013 |
| JP | S6073343 | 4/1985 |
| JP | 2000292354 | 10/2000 |
| JP | 2001-088098 A3 | 4/2001 |
| JP | 2002-501173 | 1/2002 |
| JP | 2002-506208 A | 2/2002 |
| JP | 2002-516982 | 6/2002 |
| JP | 2004017374 | 2/2004 |
| JP | 2006515065 | 5/2006 |
| JP | 2006-149215 | 6/2006 |
| JP | 2008-525768 A1 | 7/2008 |
| JP | 2009-002933 | 1/2009 |
| JP | 2010-151683 | 7/2010 |
| WO | WO 94/09366 | 4/1994 |
| WO | WO 97/14951 | 4/1997 |
| WO | WO 99/20998 A1 | 4/1999 |
| WO | WO 99/35497 | 7/1999 |
| WO | WO 99/45384 A1 | 9/1999 |
| WO | WO 00/28297 A2 | 5/2000 |
| WO | WO 00/29847 | 5/2000 |
| WO | WO 02/44729 A1 | 6/2002 |
| WO | WO 02/50518 | 6/2002 |
| WO | WO 03/036290 A1 | 5/2003 |
| WO | WO 2004/100887 | 11/2004 |
| WO | WO 2004107969 A1 | 12/2004 |
| WO | WO 2005100539 | 10/2005 |
| WO | WO 2006/047831 A1 | 5/2006 |
| WO | WO 2006/096126 A1 | 9/2006 |
| WO | WO 2006/116616 | 11/2006 |
| WO | WO 2006/119368 A2 | 11/2006 |
| WO | WO 2007/012975 A1 | 2/2007 |
| WO | WO 2007/033318 A2 | 3/2007 |
| WO | WO 2007/051861 A1 | 5/2007 |
| WO | WO 2007/111555 A1 | 10/2007 |
| WO | WO 2008/002462 A2 | 1/2008 |
| WO | WO 2008/010761 | 1/2008 |
| WO | WO 2008/037068 A1 | 4/2008 |
| WO | WO 2008/103992 A2 | 8/2008 |
| WO | WO 2008/137212 | 11/2008 |
| WO | WO 2009/091318 | 7/2009 |
| WO | WO 2009/1 05711 | 8/2009 |
| WO | WO 2009/125998 | 10/2009 |
| WO | WO 2010/085658 A1 | 7/2010 |
| WO | WO 2011/133540 A2 | 10/2011 |
| WO | WO 2013/075031 A1 | 5/2013 |
| WO | WO 2013075031 | 5/2013 |

OTHER PUBLICATIONS

Cheng et al. "A microfluidic device for practical label-free CD4+ T cell counting of HIV—infected subjects," Lab Chip, 7: 170-178 (2007).

Debernardi et al. "Single cell Ca2+ /cAMP cross-talk monitoring by simutaneous Ca2+ /cAMP fluorescence ratio imaging," Proc. Natl. Acad. Sci. 93:4577-4582 (1996).

Fischer et al. "An affordable, portable fluorescent imaging device for skin lesion detection using a dual wavelength approach for image contrast enhancement and aminolaevulinic acid-induced protoporphyrin IX. Part I. Design, spectral and spatial characteristics," Lasers Med Sci., 16: 199-296 (2001).

Fischer et al. "An affordable, portable fluorescent imaging device for skin lesion detection using a dual wavelength approach for image contrast enhancement and aminolaevulinic acid-induced protoporphyrin IX. Part II. In vivo testing," Lasers Med Sci., 16: 207-212 (2001).

Fridley et al., Controlled release of dry reagents in porous media for tunable temporal and spatial distribution upon rehydration, Lab Chip. Nov. 7, 2012;12(21):4321-4327.

Fukano et al. "Fast dual-excitation radiometry with light-emitting diodes and high-speed liquid crystal shutters," Biochemical and Biophysical Research Communications, 340:250-255 (2006).

Gerstner et al. "Quantitative Histology by Multicolor Slide-based Cytometry," Cytometry Part A, 50A: 210-219 (2004).

Hart et al. "Light emitting diode excitation emission matrix fluorescence spectroscopy," Anlayst. (127): 1693-1699 (2002).

Heiden et al. "New Epi-Fluoresence optical system for independent analysis of two different fluorochromes in microscopy," Cytometry 20: 95-101 (1995).

Holland et al. "Point-of-care molecular diagnostic systems-past, present and future," Current Opinion in Microbiology, 8: 504-509 (2005).

Janossy et al. "Precise CD4 T-Cell counting using red diode laser excitation: for richer, for poorer," Cytometry (Clinical Cytometry) 50: 78-85 (2002).

Kassotis et al. "An inexpensive dual-excitation apparatus for fluorescence microscopy," Pfugers Arch., 409:47-51 (1987).

Lewis et al. "Color-blind fluorescence detection for four-color DNA sequencing"; PNAS; www.pnas.org/cgi/ doi/10/1073/pnas. 0501606102; Apr. 12, 2005; vol. 102, No. 5: 5346-5351.

Li et al. "CD4 T lymphocytes enumeration by an easy-to-use single platform Image cytometer for HIV monitoring in resource-constrained settings," Cytometry Part B (Clinical Cytometry) 728: 397-407 (2007).

(56) References Cited

OTHER PUBLICATIONS

Myers et al. "Innovations in optical microfluidic technologies for point-of-care diagnostics", Lab on a Chip, vol. 8, pp. 2015-2031 (2008).
Rodriguez et al. "A microchip CD4 counting method for HIV monitoring in resource-poor settings," PLoS Medicine, 2 (7): 0663-0672 (2005).
Shapiro, "Cellular astronomy—a foreseeable future in cytometry," Cytometry Part A, 60A: 115-124 (2004).
Shapiro, "Personal cytometers: Slow flow or no flow," Cytometry Part A, 69A: 620-630 (2006).
Toner et al. "Blood-on-a-chip," Annu. Rev. Biomed. Eng. 7: 77-103 (2005).
Tsien et al. "Measurement of cytosolic free Ca2+ in individual small cells using fluorescence microscopy with dual excitation wavelengths," Cell Calcium 6:145-157 (1985).
Warner et al. "Multicomponent analysis in clinical chemistry by use of rapid scanning fluorescence spectroscopy," Clin. Chern. 22/9: 1483-1492 (1967).
Wittrup et al. "Fluorescence array detector for large-field quantitative fluorescence cytometry," Cytometry 16: 206-213 (1994).
Yager et al. "Microfluidic diagnostic technologies for global public health," Nature 442: 412-418 (2006).
Ymeti et al. "A single platform image cytometer for resource-poor settings to monitor disease progression in HIV infection," Cytometry Part A 71A: 132-142 (2007).
Communication pursuant to Article A94(3) EPC for European application No. 4861862.2, dated Apr. 16, 2018, 7 pages.
Anonymous: "Absorbance—Wikipedia, the free encyclopedia," Oct. 23, 2013, Retrieved from the Internet: http:web.archive.org/web/20131023072058/https://en.wikipedia.org/wiki/Absorbance [retrieved on Jun. 20, 2017], 5 pages.
Anonymous: "Beer-Lambert law• Wikipedia, the free encyclopedia," May 26, 2013 Retrieved from the Internet: URL: http://web.archive.org/web/20130526203223/https://en.wikipedia.org/wiki/Beer-Lambert.law.[retrieved on Jun. 20, 2017], 6 pages.
Bornheimer et al., "Development of the BD F ACSPresto TM System for Point-of-Care Determination of CD4 absolute count %CD4, and total Hb", BD Biosciences IAS FACSPresto Poster (2013), 1 page.
Malmstadt et al. "'Smart' mobile affinity matrix for microfluidic immunoassays," Lab on a Chip 2004, vol. 4, pp. 412-415.
Tsougeni et al. "'Smart' polymeric microfluidics fabricated by plasma processing: controlled wetting, capillary filling and hydrophobic valving," Lab on a Chip 2010, vol. 10, pp. 462-469.

OPTICAL IMAGING SYSTEM AND METHODS FOR USING THE SAME

CROSS-REFERENCE TO RELATED APPLICATIONS

Pursuant to 35 U.S.C. § 119(e), this application claims priority to U.S. Provisional Patent Application Ser. No. 61/903,804, filed on Nov. 13, 2013, and U.S. Provisional Patent Application Ser. No. 61/949,833 filed on Mar. 7, 2014, the disclosures of which applications are incorporated herein by reference.

INTRODUCTION

The characterization of analytes in biological fluids has become an integral part of medical diagnoses and assessments of overall health and wellness of a patient. In particular, analyte detection in physiological fluids, e.g., blood or blood derived products is of ever increasing importance where the results may play a prominent role in the treatment protocol of a patient in a variety of disease conditions. In response to this growing importance of analyte detection, a variety of analyte detection protocols and devices for laboratory, clinical and at-home use have been developed.

For example, patients having abnormal levels of hemoglobin often suffer from various conditions including anemia, sickle cell anemia, loss of blood, nutritional deficiency, bone marrow problems and disorders, including polycythemia rubra vera, dehydration, lung disease, certain tumors, and drug abuse, including abuse of the drug erythropoietin. Specific treatment of these conditions often depends on the duration and level of hemoglobin abnormality. Therefore, being able to rapidly and accurately determine the concentration of hemoglobin in the blood of a patient would substantially help in diagnosing and managing conditions in a patient which arise due to abnormal levels of hemoglobin.

SUMMARY

Aspects of the present disclosure include methods for assaying a sample for an analyte. Methods according to certain embodiments include illuminating a sample in a sample chamber with a light source through a slit projection module, detecting light transmitted through the sample and calculating absorbance of the detected light at one or more wavelengths to assay the sample for the analyte. A slit projection module having a slit that narrows a beam of light from the light source coupled to a focusing lens to focuses light from the slit, a microcartridge device having a sample chamber for assaying the sample and imaging systems having a light source, a slit projection module, an objective lens for focusing light transmitted through the sample and a detector for detecting one or more wavelengths of the transmitted light suitable for practicing the subject methods are also described.

As summarized above, aspects of the present disclosure include a method of assaying a sample for an analyte where the method includes the steps of illuminating a sample in a sample chamber with a light source through a slit projection module, detecting light transmitted through the sample and calculating the absorbance of the detected light at one or more wavelengths to assay the sample for the analyte.

In some embodiments, the sample is illuminated with one or more broad spectrum light sources. The sample may be illuminated with light using one or more visible or near infrared light sources, in certain instances, with wavelengths which range from 500 nm to 850 nm. For example, the sample may be illuminated with two broad spectrum light sources where the sample is illuminated with first broad spectrum light source having a wavelength range from 500 nm to 700 nm and a second broad spectrum light source having a wavelength range from 700 nm to 850 nm. In certain embodiments, the one or more broad spectrum light sources have an irradiation profile with emission peaks at about 450 nm, 550 nm and 830 nm.

In embodiments, the sample is illuminated with the broad spectrum light source through a slit projection module having a slit that narrows a beam of light coupled to a focusing lens to focused narrowed light from the light source. The slit projection module, when illuminated projects a beam of light in the shape of a slit onto the sample chamber. In some embodiments, the sample chamber is illuminated by moving the sample chamber across the slit-shaped beam. In other embodiments, the sample chamber is illuminated by moving the slit-shaped projection module along the length of the sample chamber.

In some instances, the slit projection module narrows the beam of light such that length of the slit-shaped beam projection is less than the width of the sample chamber. In other instances, the slit projection module narrows the beam of light such that the length of the slit-shaped beam projection is greater than the width of the sample chamber. In yet other instances, the slit projection module narrows the beam of light such that the length of the slit-shaped beam projection is substantially the same as the width of the sample chamber. In these embodiments, the slit projection module narrows the beam of light such that the slit-shaped beam projection has a length of from about 2.5 mm to about 3.5 mm, such as about 3 mm. In some embodiments, the slit projection module is configured to project a light beam in the shape of a slit having a width of from about 25 µm to about 75 µm, such as for example about 50 µm.

In some embodiments, the sample is illuminated by moving the microfluidic chamber containing sample across the slit-shaped beam projection along 75% or more of the length of the microfluidic chamber. In certain instances, the sample is illuminated by moving the length of the sample chamber along the slit-shaped beam projection. In some instances, the method includes moving the length of the microfluidic chamber along the slit-shaped beam projection in discrete increments, such as for example in 1 mm or greater increments, such as 2 mm or greater increments and including 5 mm or greater increments. In other instances, methods also include continuously moving the length of the sample chamber along the slit-shaped beam projection. In some embodiments, the absorbance of light is measured continuously as the length of the sample chamber is moved along the slit.

In other embodiments, the sample is illuminated by moving the slit-projection module in a manner sufficient to displace the slit-shaped beam projection along 75% or more of the length of the microfluidic chamber. In certain instances, the sample is illuminated by moving the slit-projection module in a manner sufficient to displace the slit-shaped beam projection along the length of the sample chamber. In some instances, the method includes moving the slit-projection module in a manner sufficient to displace the slit-shaped beam projection along the length of the sample chamber in discrete increments, such as for example in 1 mm or greater increments, such as 2 mm or greater increments and including 5 mm or greater increments. In other instances, methods includes moving the slit-projection module in a manner sufficient to continuously move the slit-shaped beam projection along the length of the sample chamber. In some embodiments, the absorbance of light is measured continuously.

In some embodiments, detecting light transmitted through the sample includes spatially separating wavelengths of the transmitted light. In certain instances, spatially separating wavelengths of the transmitted light includes using a diffraction grating. In certain embodiments, detecting light transmitted through the sample includes projecting a non-diffracted image of the slit on the detector, such as for example for use in calibrating the detector.

In embodiments, methods also include calculating absorbance of the detected light at one or more wavelengths to assay the sample for the analyte. For example, the absorbance of the detected light may be calculated at two different wavelengths. In certain instances, to assay the sample for the analyte the absorbance of transmitted light is calculated at a wavelength between 500 nm and 600 nm, such as at 548 nm. In other instances, to assay the sample for the analyte the absorbance of transmitted light is calculated at a wavelength between 600 nm and 700 nm, such as 650 nm and such as at 675 nm. In yet other instances, to assay the sample for the analyte a first absorbance of transmitted light is calculated at a wavelength between 500 nm and 600 nm and a second absorbance is calculated at a wavelength between 600 nm and 700 nm, such as calculating absorbance of transmitted light at 548 nm and at 675 nm. In still another instance, to assay the sample for the analyte a first absorbance of transmitted light is calculated at a wavelength between 500 nm and 600 nm and a second absorbance is calculated at a wavelength between 600 nm and 700 nm, such as calculating absorbance of transmitted light at 548 nm and at 650 nm.

Aspects of the present disclosure also include systems for practicing the subject methods. Systems, according to certain embodiments, include a light source for illuminating a sample chamber and a slit projection module which contains a slit that narrows the beam of light from the light source and a focusing lens for focusing the light narrowed by the slit to provide a slit-shaped beam projection at the sample chamber. Systems also include an objective lens for focusing light transmitted through the sample and a detector for detecting one or more wavelengths of light transmitted through the sample.

In some embodiments, systems include one or more broad spectrum light sources. The broad spectrum light sources, in certain instances, include one or more visible or near infrared light sources, such as with wavelengths which range from 500 nm to 850 nm. For example, the first broad spectrum light source may have emission wavelengths ranging from 500 nm to 700 nm and the second broad spectrum light source having emission wavelengths ranging from 700 nm to 850 nm. In certain embodiments, the one or more broad spectrum light sources have an irradiation profile with emission peaks at about 450 nm, 550 nm and 830 nm.

Systems also include a slit projection module having a slit that narrows a beam of light from the light source and a focusing lens which focuses the narrowed beam of light to provide a projection of the beam of light in the shape of a slit. The slit projection module may be configured such that the length of the slit-shaped beam projection is orthogonal to the width of the sample chamber. The width of the light beam projected in the shape of a slit may vary, such as ranging from 75 µm to 125 µm, including 100 µm. The length of the light beam projected in the shape of a slit may also vary, ranging from 2 mm to 3 mm, such as 2.5 mm. The slit projection module may be configured to project a beam of light in the shape of a slit which is greater than the width of the sample chamber. Alternatively, the slit projection module may be configured to project a beam of light in the shape of a slit which is equal to the width of the sample chamber. Likewise, the slit projection module may be configured to project a beam of light in the shape of slit which is less than the width of the sample chamber.

In some instances, the slit projection module also includes an optical adjustment protocol. By "optical adjustment" is meant that the beam of light in the shape of a slit may be changed as desired, such as to increase or decrease the dimensions or to enhance the optical resolution of the slit shaped beam. In some instances, optical adjustment is a magnification protocol configured to increase the width of the slit, such as by 5% or greater, such as by 10% or greater, such as by 25% or greater, such as by 50% or greater and including increasing the width of the slit shaped beam by 75% or greater. In other instances, optical adjustment is a de-magnification protocol configured to decrease the width of the slit, such as by 5% or greater, such as by 10% or greater, such as by 25% or greater, such as by 50% or greater and including decreasing the width of the slit shaped beam by 75% or greater. In certain embodiments, optical adjustment is an enhanced resolution protocol configured to improve the resolution of the slit shaped beam, such as by 5% or greater, such as by 10% or greater, such as by 25% or greater, such as by 50% or greater and including enhancing the resolution of the slit shaped beam by 75% or greater. The slit shaped beam may be adjusted with any convenient optical adjustment protocol, including but not limited to lens, mirrors, pinholes, slits, and combinations thereof. In certain embodiments, the slit projection module includes a focusing lens coupled to the slit to focus the light narrowed by the slit. The focusing lens, for example may be a de-magnifying lens, such as having a magnification ratio from about 0.5 to 0.75. For instance, the de-magnifying lens may be a doublet achromatic de-magnifying lens having a magnification ratio of about 0.6.

Systems according to some embodiments also include an objective lens for focusing light transmitted through the sample chamber. In some instances, the objective lens is a magnifying lens, such as having a magnification ratio of from 1.5 to 2.5. For example, the objective lens may be a double achromatic magnifying lens having a magnification ratio of about 1.7.

As described above, the collected light transmitted through the sample may be spatially separated into distinct wavelengths for detection. In some embodiments, systems include a diffraction grating for separating light into separate wavelengths. In other embodiments, systems may include a plurality of filters for separating light into distinct wavelengths for detection. In yet other embodiments, systems may include a combination of one or more diffraction gratings and a plurality of filters.

Systems also include a detector for detecting transmitted light from the sample. In some embodiments, the detector is a charged coupled device. The detector, in certain instances, is configured to detect light transmitted through the sample at wavelengths ranging from 400 nm to 900 nm. For example, the detector may be configured to detect a spectrum of transmitted light from 500 nm to 800 nm.

In embodiments of the present disclosure, systems are configured to provide a spatial separation resolution of from 5 nm or less, such as 4 nm or less, such as 3 nm or less, such as 2 nm or less and including 1 nm or less. As such, in some embodiments systems including the slit projection module, objective lens, diffraction grating and detector for detecting transmitted light are configured to provide a spatial separation resolution of from 5 nm or less, such as 4 nm or less, such as 3 nm or less, such as 2 nm or less and including 1 nm or less. In other embodiments, systems including the slit projection module, objective lens, filter wheel and detector detecting transmitted light are configured to provide a spatial resolution of from 5 nm or less, such as 4 nm or less, such as 3 nm or less, such as 2 nm or less and including 1 nm or less.

Aspects of the present disclosure also include a slit projection module for assaying a sample according to the subject methods. The slit projection module, in some embodiments, includes a slit that narrows a beam of light from the light source and a focusing lens which focuses the narrowed beam of light to provide a beam of light in the shape of a slit. The slit projection module may be configured such that the length of the slit is orthogonal to the width of the sample chamber. In certain instances, the slit projection module is configured to project a light beam in the shape of a slit illuminating the sample chamber. The width of the light beam projected in the shape of a slit may vary, such as ranging from 75 μm to 125 μm, including 100 μm. The length of the light beam projected in the shape of a slit may also vary, ranging from 2 mm to 3 mm, such as 2.5 mm. The slit projection module may be configured to project a beam of light in the shape of a slit which is greater than the width of the sample chamber. Alternatively, the slit projection module may be configured to project a beam of light in the shape of a slit which is equal to the width of the sample chamber. Likewise, the slit projection module may be configured to project a beam of light in the shape of slit which is less than the width of the sample chamber. In certain embodiments, the slit projection module includes a focusing lens coupled to the slit to focus the light narrowed by the slit. The focusing lens, in certain embodiments, is a de-magnifying lens, such as having a magnification ratio from about 0.5 to 0.75. For example, the de-magnifying lens may be a doublet achromatic de-magnifying lens having a magnification ratio of about 0.6.

Methods also include calculating absorbance of the detected light at one or more wavelengths to assay the sample for the analyte. For example, the absorbance of the detected light may be calculated at two different wavelengths. In certain instances, to assay the sample for the analyte the absorbance of transmitted light is calculated at a wavelength between 500 nm and 600 nm, such as at 548 nm. In other instances, to assay the sample for the analyte the absorbance of transmitted light is calculated at a wavelength between 600 nm and 700 nm, such as at 675 nm. In yet other instances, to assay the sample for the analyte a first absorbance of transmitted light is calculated at a wavelength between 500 nm and 600 nm and a second absorbance is calculated at a wavelength between 600 nm and 700 nm, such as calculating absorbance of transmitted light at 548 nm and at 675 nm, including calculating absorbance of transmitted light at 548 nm and at 650 nm.

Aspects of the present disclosure also include a microfluidic device configured to perform an assay of a liquid sample, where the device includes a connected sample application site, and inlet, a capillary channel sample and a reagent mixing chamber for contacting a sample with one or more reagents. The microfluidic device in certain embodiments also includes a blank reference window configured for providing a blank during absorbance measurement.

BRIEF DESCRIPTION OF THE FIGURES

The invention may be best understood from the following detailed description when read in conjunction with the accompanying drawings. Included in the drawings are the following figures:

FIG. 2a depicts a side view of absorbance systems having a slit projection module. FIG. 2b depicts a top view of absorbance systems having a slit projection module.

FIG. 9a depicts an absorbance spectrum of hemoglobin at concentration of 25 g/dL in whole blood. FIG. 9b depicts an absorbance spectrum of hemoglobin at concentration of 7 g/dL in whole blood. FIG. 9c depicts a plot of hemoglobin concentration and absorbance at 569 nm.

DETAILED DESCRIPTION

Figure 1:
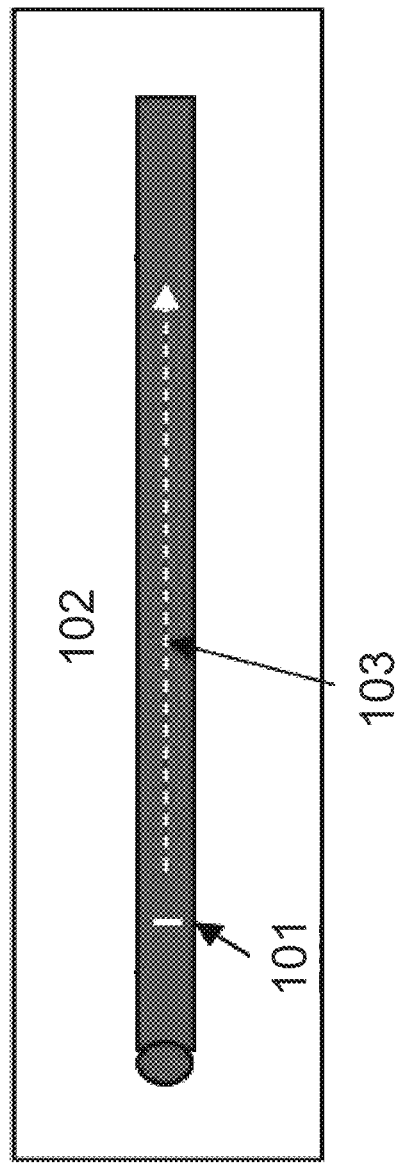
FIG. 1 illustrates an example of illuminating a sample chamber with a slit-shaped beam provided by a slit projection module according to certain embodiments.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, the present disclosure provides methods for assaying a sample for one or more analytes. In further describing embodiments of the disclosure, methods for assaying a sample for an analyte are first described in greater detail. Next, systems suitable for practicing the subject methods to assay the sample for the analyte are described. Microcartridges, computer controlled systems and kits are also provided.

Methods for Assaying a Sample for an Analyte

As summarized above, aspects of the present disclosure include methods for assaying a sample for one or more analytes. The term "assaying" is used herein in its conventional sense to refer to qualitatively assessing or quantitatively measuring the presence or amount of a target analyte species. In certain embodiments, methods include assaying a sample for hemoglobin.

A variety of different samples may be assayed according to methods of the invention, e.g., as described herein. In some instances, the sample is a biological sample. The term "biological sample" is used in its conventional sense to refer to a whole organism, plant, fungi or a subset of animal tissues, cells or component parts which may in certain instances be found in blood, mucus, lymphatic fluid, synovial fluid, cerebrospinal fluid, saliva, bronchoalveolar lavage, amniotic fluid, amniotic cord blood, urine, vaginal fluid and semen. As such, a "biological sample" refers to both the native organism or a subset of its tissues as well as to a homogenate, lysate or extract prepared from the organism or a subset of its tissues, including but not limited to, for example, plasma, serum, spinal fluid, lymph fluid, sections of the skin, respiratory, gastrointestinal, cardiovascular, and genitourinary tracts, tears, saliva, milk, blood cells, tumors, organs. Biological samples may be any type of organismic tissue, including both healthy and diseased tissue (e.g., cancerous, malignant, necrotic, etc.). In certain embodiments, the biological sample is a liquid sample, such as blood or derivative thereof, e.g., plasma, tears, urine, semen, etc., where in some instances the sample is a blood sample, including whole blood, such as blood obtained from venipuncture or fingerstick (where the blood may or may not be combined with any reagents prior to assay, such as preservatives, anticoagulants, etc.).

In certain embodiments the source of the sample is a "mammal" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some instances, the subjects are humans. The methods may be applied to samples obtained from human subjects of both genders and at any stage of development (i.e., neonates, infant, juvenile, adolescent, adult), where in certain embodiments the human subject is a juvenile, adolescent or adult. While the present invention may be applied to samples from a human subject, it is to be understood that the methods may also be carried-out on samples from other animal subjects (that is, in "non-human subjects") such as, but not limited to, birds, mice, rats, dogs, cats, livestock and horses.

In embodiments, the amount of sample assayed in the subject methods may vary, for example, ranging from 0.01 µL to 1000 µL, such as from 0.05 µL to 900 µL, such as from 0.1 µL to 800 µL, such as from 0.5 µL to 700 µL, such as from 1 µL to 600 µL, such as from 2.5 µL to 500 µL, such as from 5 µL to 400 µL, such as from 7.5 µL to 300 µL and including from 10 µL to 200 µL of sample.

In some embodiments, the biological sample is a specimen that has been preloaded into a container (e.g., blender cup, vortex microtube, sonicator vessel, etc.) and stored for a predetermined period of time before the biological sample is assayed. For example, the biological sample may be preloaded into a microfluidic cartridge, as described in greater detail below, for a period of time before the biological sample is assayed according to the subject methods. The amount of time the biological sample is stored following preloading into the container before assaying the biological sample may vary, such as 0.1 hours or more, such as 0.5 hours or more, such as 1 hour or more, such as 2 hours or more, such as 4 hours or more, such as 8 hours or more, such as 16 hours or more, such as 24 hours or more, such as 48 hours or more, such as 72 hours or more, such as 96 hours or more, such as 120 hours or more, such as 144 hours or more, such as 168 hours or more and including preloading the biological sample into the container 240 hours or more before assaying the biological sample or may range such as from 0.1 hours to 240 hours before assaying the biological sample, such as from 0.5 hours to 216 hours, such as from 1 hour to 192 hours and including from 5 hours to 168 hours before assaying the biological sample. For example, the biological sample may be preloaded into a container (e.g., microfluidic cartridge) configured for use with a system (as described below) for assaying the sample at a remote location (e.g., at home using an at-home kit or in a physician's office) and sent to a laboratory for assaying in accordance with the subject methods. By "remote location" is meant a location other than the location at which the sample is contained and preloaded into the container. For example, a remote location could be another location (e.g. office, lab, etc.) in the same city, another location in a different city, another location in a different state, another location in a different country, etc., relative to the location of the processing device, e.g., as described in greater detail below. In some instances, two locations are remote from one another if they are separated from each other by a distance of 10 m or more, such as 50 m or more, including 100 m or more, e.g., 500 m or more, 1000 m or more, 10,000 m or more, etc.

In practicing methods according to certain embodiments, a sample in a sample chamber is illuminated with a light source through a slit projection module, detecting light transmitted through the sample and calculating absorbance of the detected light at one or more wavelengths to assay the sample for the analyte. Depending on the target analyte, the sample may be illuminated with one or more sources of light. In some embodiments, the sample is illuminated with one or more broadband light sources. The term "broadband" is used herein in its conventional sense to refer to a light source which emits light having a broad range of wavelengths, such as for example, spanning 50 nm or more, such as 100 nm or more, such as 150 nm or more, such as 200 nm or more, such as 250 nm or more, such as 300 nm or more, such as 350 nm or more, such as 400 nm or more and including spanning 500 nm or more. For example, one suitable broadband light source emits light having wavelengths from 400 nm to 700 nm. Another example of a suitable broadband light source includes a light source that emits light having wavelengths from 500 nm to 700 nm. Any convenient broadband light source protocol may be employed, such as a halogen lamp, deuterium arc lamp, xenon arc lamp, stabilized fiber-coupled broadband light source, a broadband LED with continuous spectrum, superluminescent emitting diode, semiconductor light emitting diode, wide spectrum LED white light source, an multi-LED integrated white light source, among other broadband light sources or any combination thereof.

In other embodiments, the sample is illuminated with one or more narrow band light sources emitting a particular wavelength or narrow range of wavelengths. The term "narrow band" is used herein in its conventional sense to refer to a light source which emits light having a narrow range of wavelengths, such as for example, 50 nm or less, such as 40 nm or less, such as 30 nm or less, such as 25 nm or less, such as 20 nm or less, such as 15 nm or less, such as 10 nm or less, such as 5 nm or less, such as 2 nm or less and including light sources which emit a specific wavelength of light (i.e., monochromatic light). Any convenient narrow band light source protocol may be employed, such as a narrow wavelength LED, laser diode or a broadband light source coupled to one or more optical bandpass filters, diffraction gratings, monochromators or any combination thereof.

Depending on the analyte being assayed as well as interferents present the biological sample, the biological sample may be illuminated using one or more light sources, such as two or more light sources, such as three or more light sources, such as four or more light sources, such as five or more light sources and including ten or more light sources. Any combination of light sources may be used, as desired. For example, where two lights sources are employed, a first light source may be a broadband white light source (e.g., broadband white light LED) and second light source may be a broadband near-infrared light source (e.g., broadband near-IR LED). In other instances, where two light sources are employed, a first light source may be a broadband white light source (e.g., broadband white light LED) and the second light source may be a narrow spectra light source (e.g., a narrow band visible light or near-IR LED). In yet other instances, the light source is an plurality of narrow band light sources each emitting specific wavelengths, such as an array of two or more LEDs, such as an array of three or more LEDs, such as an array of five or more LEDs, including an array of ten or more LEDs.

Where more than one light source is employed, the sample may be illuminated with the light sources simultaneously or sequentially, or a combination thereof. For example, where the sample is illuminated with two light sources, the subject methods may include simultaneously illuminating the sample with both light sources. In other embodiments, the sample may be sequentially illuminated by two light sources. Where the sample is sequentially illuminated with two or more light sources, the time each light source illuminates the same may independently be 0.001 seconds or more, such as 0.01 seconds or more, such as 0.1 seconds or more, such as 1 second or more, such as 5 seconds or more, such as 10 seconds or more, such as 30 seconds or more and including 60 seconds or more. In embodiments where the sample is sequentially illuminated by two or more light sources, the duration the sample is illuminated by each light source may be the same or different.

The time period between illumination by each light source may also vary, as desired, being separated independently by a delay of 1 second or more, such as 5 seconds or more, such as by 10 seconds or more, such as by 15 seconds or more, such as by 30 seconds or more and including by 60 seconds or more. In embodiments where the sample is sequentially illuminated by more than two (i.e., three or more) light sources, the delay between illumination by each light source may be the same or different.

Depending on the assay protocol, illumination of the sample may be continuous or in discrete intervals. For example, in some embodiments, the sample may be illuminated continuously throughout the entire time the sample is being assayed. Where the light includes two or more light sources, the sample may be continuously illuminated by all of the light sources simultaneously. In other instances, the sample is continuously illuminated with each light source sequentially. In other embodiments, the sample may be illuminated in regular intervals, such as illuminating the sample every 0.001 microseconds, every 0.01 microseconds, every 0.1 microseconds, every 1 microsecond, every 10 microseconds, every 100 microseconds and including every 1000 microseconds.

The sample may be illuminated with the light source one or more times at any given measurement period, such as 2 or more times, such as 3 or more times, including 5 or more times at each measurement period.

As described in greater detail below, the light source for illuminating the sample may emit a spectrum of light having wavelengths ranging from 400 nm to 900 nm, such as from 450 nm to 850 nm, such as from 500 nm to 800 nm, such as from 550 nm to 750 nm and including from 600 nm to 700 nm. In some embodiments, the sample is illuminated with a single broad band light source emitting light with wavelengths from 400 nm to 900 nm. In other embodiments, the sample is illuminated with light with wavelengths from 400 nm to 900 nm using a plurality of light sources. For example, the sample may be illuminated with by a plurality of narrow band light sources each independently emitting light having wavelengths in the range of 400 nm to 900 nm.

In certain embodiments, the sample is illuminated with two broadband light sources emitting light with wavelengths from 400 nm to 900 nm. For example, the light sources may be white light LED emitting light having wavelengths ranging from 400 nm to 700 nm and a near-infrared LED emitting light having wavelengths ranging from 700 nm to 900 nm. Depending on the type of light source, as described above, the irradiation profile of each light source may vary, having any number of emission peaks. In certain instances, the sample is illuminated with a white light LED emitting light having wavelengths ranging from 400 nm to 700 nm and having emission peaks at about 450 nm and 550 nm and a near-infrared LED emitting light having wavelengths ranging from 700 nm to 900 nm and having an emission peak at about 830 nm.

In other embodiments, the sample is illuminated with by a plurality of narrow band lamps or LEDs each independently emitting specific wavelengths of light in the range of 400 nm to 900 nm. In one example, the narrow band light source is one or more monochromatic LEDs emitting light in the range of 500 nm to 700 nm, such as at 504 nm, 506 nm, 514 nm, 532 nm, 543 nm, 548 nm, 550 nm, 561 nm, 568 nm, 579 nm, 580 nm, 585 nm, 586 nm or any combination thereof. In another example, the narrow band light source is one or more narrow band lamps emitting light in the range of 500 nm to 700 nm, such as a narrow band cadmium lamp, cesium lamp, helium lamp, mercury lamp, mercury-cadmium lamp, potassium lamp, sodium lamp, neon lamp, zinc lamp or any combination thereof.

In embodiments of the present disclosure the sample is illuminated with a slit of illuminating light. The slit of illuminating light, e.g., as described in greater detail below, may be produced using any convenient protocol. In some embodiments, the slit of illuminating light is produced using a slit projection module, which includes a slit that may or may not be optically coupled to one or more additional components, e.g., one or more lenses. For example, in some instances the slit of illuminating light is produced from one or more light sources through a slit projection module having a slit that narrows a beam of light coupled to a focusing lens to focus the narrowed beam of light from the light source. The slit projection module narrows the beam of light and produces a beam of light in the shape of a slit projected onto the sample chamber. During interrogation of the sample, the sample chamber, the slit projection module or both the sample chamber and slit projection module may be moved (if desired) to displace the slit-shaped beam of light across the sample chamber.

As described above, the slit projection module is configured to provide a slit-shaped beam having a length and width, where the length and width of the illuminating slit may vary. The slit projection module includes a slit having an aperture configured to narrow the beam of light from the one or more light sources and a focusing lens coupled to the slit for focusing the light passing through the slit aperture. The slit aperture may be any convenient shape, including but not limited to an oval, rectangle or other polygon. In certain embodiments, the slit aperture is rectangular. Depending on the desired dimensions of slit-shaped beam provided by the light source, as described above, the dimensions of the slit aperture may vary, having a length which ranges from 01 mm to 10 mm, such as from 1.25 mm to 9.5 mm, such as from 1.5 mm to 9 mm, such as from 2 mm to 8 mm, such as from 2.5 mm to 7 mm, such as from 3 mm to 6 mm and including from 3.5 mm to 5 mm. The width of the slit aperture may range from 1 μm to 250 μm, such as from 2 μm to 225 μm, such as from 5 μm to 200 μm, such as from 10 μm to 150 μm, and including from 15 μm to 125 μm, for example a slit having an aperture width of 100 μm.

The light beam narrowed by the slit may, where desired, be focused using a focusing lens coupled to the slit. In some embodiments, the narrowed light beam is focused through a de-magnifying lens having a magnification ratio ranging from 0.1 to 0.95, such as a magnification ratio of from 0.2 to 0.9, such as a magnification ratio of from 0.3 to 0.85, such as a magnification ratio of from 0.35 to 0.8, such as a magnification ratio of from 0.5 to 0.75 and including focusing the narrowed light beam through a de-magnifying lens having a magnification ratio of from 0.55 to 0.7, for example a magnification ratio of 0.6. For example, the narrowed light beam is, in certain instances, focused through a double achromatic de-magnifying lens having a magnification ratio of about 0.6.

As described in greater detail below, the slit projection module may be configured to provide a slit-shaped beam having a length and width which varies. In some embodiments, the slit projection module is configured to provide a slit-shaped beam having a length which ranges from 1 mm to 5 mm, such as from 1.5 mm to 4.5 mm, such as from 2 mm to 4 mm, such as from 2.5 mm to 3.5 mm and including a slit-shaped beam having a length of 3 mm. In these embodiments, the slit projection module is configured to provide a slit-shaped beam having a width which ranges from 10 μm to 100 μm, such as from 15 μm to 95 μm, such as from 20 μm to 90 μm, such as from 25 μm to 85 μm, such as from 30 μm to 80 μm, such as from 35 μm to 75 μm, such as from 40 μm to 70 μm, such as from 45 μm to 65 μm, and including from 50 μm to 60 μm.

In some embodiments, the slit projection module is configured to provide a slit-shaped beam of light where the length of the slit-shaped beam is orthogonal to the length of a sample chamber being assayed. In other words, the length of the slit-shaped beam is positioned along the width of the sample chamber being assayed. Depending on the size of the sample chamber (as described in greater detail below) and slit-shaped beam projection, the slit-shaped beam may illuminate 50% or more of the width of the sample chamber, such as 55% or more, such as 60% or more, such as 65% or more, such as 70% or more, such as 75% or more, such as 80% or more, such as 85% or more, such as 90% or more, such as 95% or more, such as 97% or more and including illuminating 99% or more of the width of the sample chamber. In certain instances, the slit-shaped beam projection has a length which is substantially the same as width of the sample chamber. In other embodiments, the slit-projection module is configured to provide a slit-shaped beam projection which has a length that is greater than the width of the sample chamber. For example, the slit-shaped beam of light may have a length which is 1% or greater than the width of the sample chamber, such as 2% or greater, such as 5% or greater, such as 10% or greater, such as 15% or greater, such as 20% or greater and including a length which is 25% greater than the width of the sample chamber. In yet other embodiments, the slit-projection module is configured to provide a slit-shaped beam projection which has a length that is less than the width of the sample chamber. For example, the slit-shaped beam of light may have a length is which 1% or greater less than the width of the sample chamber, such as a length which is 2% or greater less than the width of the sample chamber, such as a length which is 5% or greater less than the width of the sample chamber, such as a length which is 10% or greater less than the width of the sample chamber, such as a length which is 15% or greater less than the width of the sample chamber, such as a length which is 20% or greater less than the width of the sample chamber and including a length which is 25% or greater less than the width of the sample chamber.

During interrogation of the sample, the sample chamber, the slit projection module or both the sample chamber and slit projection module may be moved (if desired) to displace the slit-shaped beam of light across the sample chamber. The term "move" refers to displacement between slit projection module and the sample chamber such that the slit-shaped beam of light projected onto the sample chamber changes position with time along the sample chamber during assay of the sample. In some embodiments, the sample chamber is moved while the slit-projection module is maintained in a stationary position in order to laterally displace the slit-shaped beam of light along the sample chamber during interrogation. In other embodiments, the slit-projection module is moved and the sample chamber is maintained in a stationary position in order to laterally displace the slit-shaped beam of light along the sample chamber during interrogation. In yet other embodiments, both the slit projection module and the sample are moved in order to laterally displace the slit-shaped beam of light along the sample chamber during interrogation.

In embodiments, the sample chamber or the slit-projection module may be moved such that the slit-shaped beam of light is displaced laterally relative to the sample chamber in any direction, where in some instances the length of the slit-shaped beam remains orthogonal to the length of the sample chamber. In some instances, the sample chamber or the slit-projection module is moved such that the slit-shaped beam of light is displaced from a distal end to a proximal end of the sample chamber. In other instances, the sample chamber or the slit-projection module is moved such that the slit-shaped beam of light is displaced from a proximal end to a distal end of the sample chamber. The sample chamber or the slit-projection module may be configured to move such that the slit-shaped beam of light is displaced along all or a portion of the length of the sample chamber to interrogate the sample. In some embodiments, the slit-shaped beam of light is displaced along 50% or more of the sample chamber, such as 55% or more, such as 60% or more, such as 65% or more, such as 70% or more, such as 75% or more, such as 80% or more, such as 85% or more, such as 90% or more, such as 95% or more, such as 97% or more and including along 99% or more of the length of the sample chamber. In certain instances, the slit-shaped beam is displaced along substantially the entire length of the sample chamber.

In certain embodiments, sample chamber or slit-projection module is moved so that the slit-shaped beam light is displaced in a back-and-forth motion relative to the sample chamber, such as moving from a distal end to a proximal end of the sample chamber and back from the proximal end to the distal end of the sample chamber. In other instances, the sample chamber or slit-projection module is moved so that the slit-shaped beam of light is displaced relative to the sample chamber from the proximal end to distal end of the sample chamber and back from the distal end to the proximal end of the sample chamber. The sample chamber or slit-projection module is moved so that the slit-shaped beam of light is, in certain instances, displaced in a back-and-forth motion along only a portion of the sample chamber. For example, the sample chamber or slit-projection module is moved so that the slit-shaped beam may be displaced in a back-and-forth motion along 99% or less of the sample chamber, such as 95% or less, such as 90% or less, such as 85% or less, such as 80% or less, such as 75% or less, such as 70% or less, such as 65% or more, including moving the sample chamber or slit-projection module is moved so that the slit-shaped beam is displaced in a back-and-forth motion along 50% or less of the length of the sample chamber.

Where the slit-shaped beam of light is moved in a back-and-forth motion, the movement of the sample chamber or slit-projection module may be repeated one or more times during any given interrogation period, such as 2 or more times, such as 5 or more times, such as 10 or more times, such as 15 or more times and including 25 or more times during each interrogation period.

The amplitude of displacement of the slit-shaped beam of light along the sample chamber during interrogation may vary. By "amplitude of displacement" or "total displacement" is meant the sum total of distance traversed by the slit-shaped beam of light along the sample chamber. In one example, where the slit-shaped beam of light is moved from a proximal end to a distal end of a 60 mm sample chamber, the total displacement of the slit-shaped beam of light is 60 mm. In another example, where the slit-shaped beam is moved from a distal end to a proximal end of a 60 mm sample chamber, the total displacement of the slit-shaped beam of light is 60 mm. In yet another example, where the slit-shaped beam is moved in a back-and-forth motion from the proximal end to a distal end and back from the distal end to the proximal end of a 60 mm sample chamber, the total displacement is 120 mm. In still another example, where the slit-shaped beam is moved in a back-and-forth motion (e.g., from proximal end to distal end and back from distal end to proximal end) along 50% of a 60 mm sample chamber, the total displacement is 60 mm. In still another example, where the slit-shaped beam is moved in a back-and-forth motion (e.g., from distal end to proximal end and back from proximal end to distal end) along 50% of a 60 mm sample chamber and repeated 5 times, the total displacement is 300 mm.

In embodiments of the present disclosure, the total displacement varies, ranging from 0.1 mm to 1000 mm, such as from 0.2 mm to 950 mm, such as from 0.3 mm to 900 mm, such as from 0.4 mm to 850 mm, such as from 0.5 mm to 800 mm, such as from 0.6 mm to 750 mm, such as from 0.7 mm to 700 mm, such as from 0.8 mm to 650 mm, such as from 0.9 mm to 600 mm, such as from 1 mm to 550 mm, such as from 1.25 mm to 500 mm, such as from 1.5 mm to 450 mm, such as from 1.75 mm to 400 mm, such as from 2 mm to 300 mm, such as from 2.5 mm to 250 mm and including from 3 mm to 200 mm.

The slit-shaped beam of light may be moved along the sample chamber at a rate which varies, such as at a rate of 0.001 mm/second or more, such as at a rate of 0.005 mm/second or more, such as at a rate of 0.01 mm/second or more, such as at a rate of 0.05 mm/second or more, such as at a rate of 0.1 mm/second or more, such as at a rate of 0.5 mm/second or more, such as at a rate of 1 mm/second or more, such as at a rate of 1.5 mm/second or more, such as at a rate of 2 mm/second or more, such as at a rate of 2.5 mm/second or more, such as at a rate of 3 mm/second, such as at a rate of 5 mm/second or more, such as at a rate of 10 mm/second or more, such as at a rate of 20 mm/second or more, such as at a rate of 30 mm/second or more, such as at a rate of 40 mm/second or more and including moving the slit-shaped beam along the sample chamber at a rate of 60 mm/second or more. Where the slit-shaped beam is moved along the sample chamber in a back-and-forth motion, the rate may be 1 back-and-forth cycle per minute or more, such as 2 cycles per minute or more, such as 3 cycles per minute or more, such as 4 cycles per minute or more, such as 5 cycles per minute or more, such as 10 cycles per minute or more, such as 15 cycles per minute or more, such as 20 cycles per minute or more, such as 30 cycles per minute or more, such as 45 cycles per minute or more and including 60 back-and-forth cycles per minute or more.

Movement of the sample chamber or slit-projection module to displace the slit-shaped beam along the sample chamber may be continuous or in discrete increments. In some embodiments, the sample chamber or slit-projection module is moved so that the slit-shaped beam of light is displaced along the sample chamber continuously throughout the entire time the sample is being assayed, such as at a rate of 0.001 mm/second or more, such as at a rate of 0.005 mm/second or more, such as at a rate of 0.01 mm/second or more, such as at a rate of 0.05 mm/second or more, such as at a rate of 0.1 mm/second or more, such as at a rate of 0.5 mm/second or more, such as at a rate of 1 mm/second or more, such as at a rate of 1.5 mm/second or more, such as at a rate of 2 mm/second or more, such as at a rate of 2.5 mm/second or more, such as at a rate of 3 mm/second, such as at a rate of 5 mm/second or more, such as at a rate of 10 mm/second or more, such as at a rate of 20 mm/second or more, such as at a rate of 30 mm/second or more, such as at a rate of 40 mm/second or more and including moving the sample chamber or slit-projection module so that the slit-shaped beam of light is continuously displaced relative to the sample chamber at a rate of 60 mm/second or more.

In other embodiments, the sample chamber or slit-projection module is moved so that the slit-shaped beam is displaced relative to the sample chamber in discrete increments. In these embodiments, the slit-shaped beam of light is, in some instances, displaced relative to the sample chamber in regular increments, such as at 0.01 mm increments, 0.05 mm increments, 0.1 mm increments, 0.2 mm increments, 0.3 mm increments, 0.5 mm increments, 0.75 mm increments, 1 mm increments, 2.5 mm increments, 5 mm increments, 7.5 mm increments, 10 mm increments, 15 mm increments, 20 mm increments or some other increment. In other instances, the slit-shaped beam of light is displaced relative to the sample chamber in random increments ranging from 0.01 mm to 20 mm increments, such as from 0.1 mm to 17.5 mm, such as from 0.5 mm to 15 mm increments, including random increments ranging from 1 mm to 10 mm increments.

As described above, in some embodiments the sample chamber is sequentially illuminated with a plurality of light sources. Where the sample chamber is sequentially illuminated with more than one light source, each light source independently provides a slit-shaped beam of light which is displaced relative to the sample chamber. The movement of each slit-shaped light beam of light relative to the sample chamber provided by the plurality of light sources may be the same or different, as described above. For example, where the sample chamber is sequentially illuminated with two light sources (e.g., a broadband white light LED and a near-IR LED), a first slit-shaped beam produced by the first light source (e.g., broadband white light LED) interrogates the sample chamber sequentially with a second slit-shaped beam produced by the second light source (e.g., near-IR LED). In other words, in these embodiments at least two slit-shaped beams are provided to interrogate the sample chamber. For example, in some embodiments a first light source providing a first slit-shaped beam may be moved along the sample chamber in a back-and-forth motion while a second light source providing a second slit-shaped beam may be moved along the sample chamber in only a single direction. In other embodiments, a first light source providing a first slit-shaped beam may be moved along the sample chamber in a back-and-forth motion for a plurality of cycles while the second light source providing a second slit-shaped beam may be moved in a back-and-forth motion for a single cycle.

FIG. 1 depicts displacement of a slit-shaped beam of light relative to a sample chamber. The slit-shaped beam (101) provided by a slit projection module is oriented across the width of the sample chamber (102) and the sample chamber is moved laterally (103) across the slit-shaped beam of light to illuminating all or part of the sample chamber. As desired, the sample chamber or the slit-projection module may be moved so that the slit-shaped beam can be displaced relative to the sample chamber one or more times or in a back-and-forth motion.

In some embodiments, the light transmitted though the sample chamber is collected and passed through one or more objective lenses. In certain instances, light transmitted through the sample chamber is collected and passed through a magnifying lens with a nominal magnification ranging from 1.2 to 2.5, such as a nominal magnification of from 1.3 to 2.4, such as a nominal magnification of from 1.4 to 2.3, such as a nominal magnification of from 1.5 to 2.2, such as a nominal magnification or from 1.6 to 2.1, including passing the transmitted light through a magnifying lens having a nominal magnification of from 1.7 to 2.0, for example a nominal magnification of 1.7. For example, the transmitted light is, in certain instances, collected and passed through a magnifying achromatic doublet lens with a nominal magnification of 1.7. Depending on the configuration of the light source, sample chamber and detector, properties of the objective lens may vary. For example, the numerical aperture of the subject objective lens may also vary, ranging from 0.01 to 1.7, such as from 0.05 to 1.6, such as from 0.1 to 1.5, such as from 0.2 to 1.4, such as from 0.3 to 1.3, such as from 0.4 to 1.2, such as from 0.5 to 1.1 and including a numerical aperture ranging from 0.6 to 1.0. Likewise, the focal length of the objective lens varies, ranging from 10 mm to 20 mm, such as from 10.5 mm to 19 mm, such as from 11 mm to 18 mm and including from 12 mm to 15 mm.

In some embodiments, the slit-shaped beam projection transmitted through the sample chamber is also focused using an autofocus module. For example, suitable protocols for focusing the slit-shaped beam projection transmitted through the sample chamber may include, but are not limited to, those described in U.S. Pat. No. 6,441,894, filed on Oct. 29, 1999, the disclosure of which is herein incorporated by reference.

Methods according to some embodiments of the present disclosure also include passing the transmitted light through one or more wavelength separators. The term "wavelength separator" is used herein in its conventional sense to refer to an optical protocol for separating polychromatic light into its component wavelengths for detection. Wavelength separation, according to certain embodiments, may include selectively passing or blocking specific wavelengths or wavelength ranges of the polychromatic light. To separate wavelengths of light, the transmitted light may be passed through any convenient wavelength separating protocol, including but not limited to colored glass, bandpass filters, interference filters, dichroic mirrors, diffraction gratings, monochromators and combinations thereof, among other wavelength separating protocols.

In some embodiments, methods include separating the light transmitted from the sample chamber by passing the transmitted light through one or more diffraction gratings. Diffraction gratings of interest may include, but are not limited to transmission, dispersive or reflective diffraction gratings. Suitable spacings of the diffraction grating may vary depending on the configuration of the light source, slit projection module, sample chamber, objective lens, ranging from 0.01 µm to 10 µm, such as from 0.025 µm to 7.5 µm, such as from 0.5 µm to 5 µm, such as from 0.75 µm to 4 µm, such as from 1 µm to 3.5 µm and including from 1.5 µm to 3.5 µm. In other embodiments, methods include separating the light transmitted from the sample chamber by passing the transmitted light through one or more optical filters, such as one or more bandpass filters. For example, optical filters of interest may include bandpass filters having minimum bandwidths ranging from 2 nm to 100 nm, such as from 3 nm to 95 nm, such as from 5 nm to 95 nm, such as from 10 nm to 90 nm, such as from 12 nm to 85 nm, such as from 15 nm to 80 nm and including bandpass filters having minimum bandwidths ranging from 20 nm to 50 nm. In certain instances, methods include passing the transmitted light from the sample chamber through one or more bandpass filters which selectively pass wavelengths in the ranges of: 498 nm-510 nm; 500 nm-600 nm; 500 nm-520 nm; 540 nm-550 nm; 545 nm-555 nm; 550 nm-570 nm; 550 nm-580 nm; 560 nm-590 nm; 575 nm-595 nm; 580 nm-590 nm; 600 nm-700 nm; 600 nm-630 nm; 650 nm-750 nm; 750 nm-850 nm; 810 nm-830 nm; 815 nm-825 nm or any combination thereof.

For example, in one instance methods include passing the transmitted light from the sample chamber through one or more bandpass filters which selectively passes wavelengths ranging from 500 nm-520 nm and from 650 nm-750 nm. In another instance, methods include passing the transmitted light from the sample chamber through one or more bandpass filters which selectively passes wavelengths ranging from 540 nm-560 nm and from 650 nm-750 nm. In yet another instance, methods include passing the transmitted light from the sample chamber through one or more bandpass filters which selectively passes wavelengths ranging from 560 nm-590 nm and from 650 nm-750 nm. In still another instance, methods include passing the transmitted light from the sample chamber through one or more bandpass filters which selectively passes wavelengths ranging from 500 nm-520 nm; 560 nm-590 nm and from 650 nm-750 nm.

In practicing methods according to aspects of the present disclosure, the light transmitted through the sample chamber is measured at one or more wavelengths. In embodiments, the transmitted light is measured at one or more wavelengths, such as at 5 or more different wavelengths, such as at 10 or more different wavelengths, such as at 25 or more different wavelengths, such as at 50 or more different wavelengths, such as at 100 or more different wavelengths, such as at 200 or more different wavelengths, such as at 300 or more different wavelengths and including measuring the light transmitted through the sample chamber at 400 or more different wavelengths.

In some embodiments, measuring light transmitted through the sample chamber includes measuring transmitted light over a range of wavelengths (e.g., 400 nm-800 nm; 495 nm-525 nm; 800 nm-835 nm, etc.). For example, methods may include measuring light transmitted through the sample chamber over one or more of the wavelength ranges of: 400 nm-800 nm; 498 nm-510 nm; 500 nm-600 nm; 500 nm-700 nm; 500 nm-575 nm; 500 nm-550 nm; 540 nm-550 nm; 545 nm-555 nm; 550 nm-570 nm; 550 nm-580 nm; 560 nm-590 nm; 575 nm-595 nm; 580 nm-590 nm; 600 nm-700 nm; 600 nm-630 nm; 650 nm-750 nm; 650 nm-830; 750 nm-850 nm; 810 nm-830 nm; 815 nm-825 nm and any combinations thereof. In one instance, methods include measuring transmitted light over the wavelengths ranging from 400 nm-800 nm. In another instance, methods include measuring transmitted light over the wavelengths ranging from 500 nm-520 nm and 650 nm-750 nm. In another instance, methods include measuring transmitted light over wavelengths ranging from 540 nm-560 nm and 650 nm-750 nm. In yet another instance, methods include measuring transmitted light over wavelengths ranging from 560 nm-590 nm and 650 nm-750 nm. In still another instance, methods include measuring transmitted light over wavelengths ranging from 500 nm-520 nm, 560 nm-590 nm, and 650-750 nm.

Measuring transmitted light over a range of wavelengths, in certain instances, includes collecting the spectra of the transmitted light over the range of wavelengths. For example, methods may include collecting the spectra of light transmitted through the sample chamber over one or more of the wavelength ranges of: 400 nm-800 nm; 498 nm-510 nm; 500 nm-600 nm; 500 nm-700 nm; 500 nm-520 nm; 540 nm-550 nm; 545 nm-555 nm; 550 nm-570 nm; 550 nm-580 nm; 560 nm-590 nm; 575 nm-595 nm; 580 nm-590 nm; 600 nm-700 nm; 600 nm-630 nm; 650 nm-750 nm; 750 nm-850 nm; 810 nm-830 nm; 815 nm-825 nm and any combinations thereof. In one instance, methods include collecting the spectra of transmitted light over the wavelengths ranging from 400 nm-800 nm. In another instance, methods include collecting the spectra of transmitted light over the wavelengths ranging from 500 nm-700 nm.

In certain embodiments, the light transmitted through the sample chamber is detected at one or more specific wavelengths (e.g., 548 nm or 675 nm). For example, methods may include detecting the transmitted light at 2 or more specific wavelengths, such as at 3 or more specific wavelengths, such as at 4 or more specific wavelengths, such as at 5 or more specific wavelengths, such as at 10 or more specific wavelengths and including detecting the transmitted light at 25 or more specific wavelengths. In some instances, methods include detecting the transmitted light at one or more of 504 nm, 506 nm, 514 nm, 532 nm, 543 nm, 548 nm, 550 nm, 561 nm, 568 nm, 579 nm, 580 nm, 585 nm, 586 nm, 675 nm, 710 nm, 808 nm, 815 nm, 830 nm and any combinations thereof. In certain embodiments, the transmitted light is detected at 548 nm. In other embodiments, the transmitted light is detected at 675 nm. In yet other embodiments, the transmitted light is detected at 830 nm. In still other embodiments, the transmitted light is detected at 548 nm and 675 nm. In still other embodiments, the transmitted light is detected at 548 nm, 675 nm and 830 nm. In still another embodiment, the transmitted light is detected at 504 nm, 506 nm, 514 nm, 532 nm, 543 nm, 548 nm, 550 nm, 561 nm, 568 nm, 579 nm, 580 nm, 585 nm, 586 nm, 650 nm, 675 nm, 710 nm, 808 nm, 815 nm and 830 nm.

Depending on the specific assay protocol, transmitted light may be measured continuously or in discrete intervals. For example, in some embodiments, measuring transmitted light is continuous throughout the entire time the sample is being assayed. Where measuring the transmitted light includes measuring two or more wavelengths or wavelength ranges, the wavelengths or wavelength ranges may be all measured simultaneously, or each wavelength or wavelength range may be measured sequentially.

In other embodiments, transmitted light is measured in discrete intervals, such as measuring light transmitted through the sample every 0.001 microseconds, every 0.01 microseconds, every 0.1 microseconds, every 1 microsecond, every 10 microseconds, every 100 microseconds and including every 1000 microseconds.

Depending on the quality (e.g., homogeneity) of the biological sample, presence of interferents, light source and wavelengths being measured, the light transmitted through sample chamber may be measured one or more times during the subject methods, such 2 or more times, such as 3 or more times, such as 5 or more times and including 10 or more times. In certain embodiments, the transmitted light is measured two or more times, with the data being averaged to calculate absorbance by the target analyte, as described below.

In certain embodiments, methods include projecting a slit-shaped beam onto the detector to provide a blank measurement. In these embodiments, the slit-shaped beam may be accomplished by illuminating a blank reference window with the slit-shaped beam and focusing the slit-shaped beam projected through the blank reference window onto the detector.

For example, the blank reference window may be integrated into the subject systems (as described below) where light from the light source is directed through the integrated blank reference window. In some instances, light transmitted through the blank reference window is directed through the objective lens and onto the wavelength separator and detector. In other instances, light transmitted through the blank reference window is provided directly onto the detector. In some instances, the blank reference window may be positioned on the microfluidic cartridge, such as along the same optical axis as the sample chamber.

The absorbance by the blank reference window is in certain embodiments, configured to be identical to absorbance by the sample chamber such that transmission through the blank reference window can be used to correct for absorption, scatter, etc. by the microfluidic cartridge when practicing the methods described herein. In certain embodiments, the blank reference window has an absorbance and transmission at the one or more wavelengths of incident light which is substantially the same as the capillary channel sample chamber. In other embodiments, the blank reference window scatters light at the one or more wavelengths which is substantially the same as the capillary channel sample chamber. In yet other embodiments, the blank reference window has an absorbance, transmission and scatters light at the one or more incident wavelengths which is substantially the same as the capillary channel sample chamber. In still other embodiments, the blank reference window has the same index of refraction as the capillary channel sample chamber.

In other embodiments, methods include projecting non-diffracted light from the light source onto the detector to provide for a blank of incident light. In certain embodiments, the non-diffracted light is used for calibrating the detector.

Light transmitted through the sample chamber may be measured by any convenient light detecting protocol, including but not limited to photosensors or photodetectors, such as active-pixel sensors (APSs), avalanche photodiode, image sensors, charge-coupled devices (CCDs), intensified charge-coupled devices (ICCDs), light emitting diodes, photon counters, bolometers, pyroelectric detectors, photoresistors, photovoltaic cells, photodiodes, photomultiplier tubes, phototransistors, quantum dot photoconductors or photodiodes and combinations thereof, among other photodetectors. In certain embodiments, the transmitted light is measured with a charge-coupled device (CCD). Where the transmitted light is measured with a CCD, the active detecting surface area of the CCD may vary, such as from 0.01 $cm^2$ to 10 $cm^2$, such as from 0.05 $cm^2$ to 9 $cm^2$, such as from, such as from 0.1 $cm^2$ to 8 $cm^2$, such as from 0.5 $cm^2$ to 7 $cm^2$ and including from 1 $cm^2$ to 5 $cm^2$.

As summarized above, aspects of the present disclosure include methods for assaying a sample for one or more analytes. In embodiments, to assay for the analyte, the absorbance of light by the target analyte is calculated using the measured transmitted light. In some embodiments, the absorbance is calculated at one or more wavelengths, such as at 2 or more different wavelengths, such as at 3 or more different wavelengths, such as at 4 or more different wavelengths and including calculating the absorbance of the target analyte at 5 or more different wavelengths. For example, absorbance of the target analyte may be calculated using the detected transmitted light at one or more of 504 nm, 506 nm, 514 nm, 532 nm, 543 nm, 548 nm, 550 nm, 561 nm, 568 nm, 579 nm, 580 nm, 585 nm, 586 nm, 675 nm, 710 nm, 808 nm, 815 nm, 830 nm or any combinations thereof. In certain embodiments, absorbance of the analyte is calculated using the detected transmitted light at 548 nm. In other embodiments, absorbance of the analyte is calculated using the detected transmitted light at 675 nm. In yet other embodiments, absorbance of the analyte is calculated using the detected transmitted light at 830 nm. In still other embodiments, absorbance of the analyte is calculated using the detected transmitted light at 548 nm and 675 nm. In still other embodiments, absorbance of the analyte is calculated using the detected transmitted light at 548 nm, 675 nm and 830 nm.

In some embodiments, calculating absorbance of light by the target analyte includes calculating absorbance over a range of wavelengths (e.g., 400 nm-800 nm; 495 nm-525 nm; 800 nm-835 nm, etc.). For example, methods may include calculating absorbance over one or more of the wavelength ranges of: 400 nm-800 nm; 498 nm-510 nm; 500 nm-600 nm; 500 nm-700 nm; 500 nm-520 nm; 540 nm-550 nm; 545 nm-555 nm; 550 nm-570 nm; 550 nm-580 nm; 560 nm-590 nm; 575 nm-595 nm; 580 nm-590 nm; 600 nm-700 nm; 600 nm-630 nm; 650 nm-750 nm; 750 nm-850 nm; 810 nm-830 nm; 815 nm-825 nm and any combinations thereof. For example, methods include calculating absorbance of light by the target analyte over the wavelengths ranging from 400 nm-800 nm. In another instance, methods include calculating absorbance of light by the target analyte over the wavelengths ranging from 500 nm-520 nm and 650 nm-750 nm. In another instance, methods include calculating absorbance of light by the target analyte over the wavelengths ranging from 540 nm-560 nm and 650 nm-750 nm. In yet another instance, methods include calculating absorbance of light by the target analyte over the wavelengths ranging from 560 nm-590 nm and 650 nm-750 nm. In still another instance, methods include calculating absorbance of light by the target analyte over the wavelengths ranging from 500 nm-520 nm, 560 nm-590 nm, and 650-750 nm.

For example, where the sample is whole blood and the analyte of interest is hemoglobin, the concentration of hemoglobin in whole blood may be calculated by measuring transmitted light at a first and a second wavelength, where the wavelengths may vary, and include, but are not limited to, isobestic points, etc. In some instances, the first wavelength is an isobestic point for hemoglobin with one or more of oxyhemoglobin, carboxyhemoglobin, methemoglobin, sulfo-hemoglobin, azide-methemoglobin and cyanomethemoglobin, such as an isobestic point for hemoglobin and oxyhemoglobin or a triple isobestic point for hemoglobin, oxyhemoglobin and carboxyhemoglobin. For example, a first wavelength is, in certain instances, 506 nm, 548 nm, 569 nm, 579 nm, 585 nm or 586 nm. The second wavelength is, in these embodiments, a low absorbing wavelength (e.g., near-IR) and may be also be an isosbestic point for hemoglobin with one or more of oxyhemoglobin, carboxyhemoglobin, methemoglobin, sulfo-hemoglobin, azide-methemoglobin and cyano-methemoglobin, such as a isosbestic point for hemoglobin and oxyhemoglobin or a triple isosbestic point for hemoglobin, oxyhemoglobin and carboxyhemoglobin. For example, a second wavelength is, in certain instances, 650 nm, 675 nm, 710 nm, 785 nm, 808 nm, 815 nm or 830 nm.

The absorbance of light by the target analyte may be calculated using any convenient principle, e.g., the Beer-Lambert Law:

$$\text{Absorbance }(\lambda) = -\text{Log}_{10}(I/I_0)$$

where I is the intensity of the light transmitted through the sample chamber and $I_0$ is the intensity of incident light used to interrogate the sample. Depending on the path length of the sample chamber (as described below), the concentration of the analyte can be determined using the calculated absorbance of the analyte:

$$\text{Absorbance }(\lambda) = [\text{molar absorptivity}] \times [\text{concentration}] \times [\text{pathlength}]$$

Absorbance may be calculated in conjunction with measurement of the transmitted light or may be conducted after a predetermined duration following measurement of the transmitted light. In some embodiments, absorbance is continuously calculated in conjunction with measurement of the transmitted light, such as where transmitted light is measured at one or more specific wavelengths. Where the subject methods include calculating absorbance of the analyte at two or more wavelengths, the absorbance may be calculated at both wavelengths simultaneously or absorbance may be calculated at each wavelength sequentially.

In other embodiments, absorbance is calculated a predetermined duration after measurement of the transmitted light, such as 0.001 seconds or longer after measurement, such as 0.01 seconds or longer after measurement, such as 0.1 seconds or longer after measurement, such as 0.5 seconds or longer after measurement, such as 1 second or longer after measurement and including 5 seconds or longer after measurement of the transmitted light. For example, in embodiments where a spectrum over a range of wavelengths is collected, absorbance may be calculated a predetermined duration after the entire spectrum is collected.

In some embodiments, methods include calculating concentration based on absorbance determined from the transmitted light. In embodiments, the concentration of the analyte can be calculated using the absorbance at any desired wavelength, such as at two or more wavelengths, such as at three or more wavelengths and including at five or more wavelengths. In some embodiments, concentration of the analyte in the sample is calculated at one or more peak absorbance values in the absorbance spectrum. In other embodiments, concentration of the analyte in the sample is calculated using one or more wavelengths where the analyte has the largest molar absorptivity. Where two or more analytes are of interest, the concentration of the analytes may, in certain instances, be calculated using the absorbance at a wavelength corresponding to an isosbestic point for the two or more analytes.

In calculating concentration of the analyte, the absorbance of light by the target analyte is first determined using the Beer-Lambert Law:

$$\text{Absorbance }(\lambda) = -\text{Log}_{10}(I/I_0)$$

where I is the intensity of the light transmitted through the sample chamber and $I_0$ is the intensity of incident light used to interrogate the sample. Depending on the path length of the sample chamber, the concentration of the analyte is then determined using the calculated absorbance of the analyte:

$$\text{Absorbance }(\lambda) = [\text{molar absorptivity}] \times [\text{concentration}] \times [\text{pathlength}]$$

In one embodiment, methods include calculating concentration of the analyte while accounting for scatter by the sample by measuring transmitted light at a first and a second wavelength. The first wavelength, in some instances, is a wavelength where the analyte has a high molar absorptivity. In other instances, the first wavelength is a wavelength at an isosbestic point with one or more derivatives of the analyte that are included in the analyte concentration. The second wavelength is, in these embodiments, a wavelength where the analyte has low molar absorptivity. The second wavelength may also be a wavelength at an isosbestic point with one or more derivatives of the analyte. To calculate concentration of the analyte accounting for scatter:

$$\text{Concentration}_{analyte} = A^*(\text{Abs}_{\lambda 1}) + B^*(\text{Abs}_{\lambda 2}) + C,$$

where A, B, and C are coefficients which depend on the wavelengths interrogated and analytes being measured. In embodiments, the value of A may vary, in certain instances, ranging from 20 g/dL to 60 g/dL, such as from 25 g/dL to 57.5 g/dL, such as from 30 g/dL to 55 g/dL, such as from 35 g/dL to 50 g/dL and including from 37.5 g/dL to 45 g/dL. The value of B may also vary, in certain instances, ranging from 0.01 g/dL to 5 g/dL, such as from 0.05 g/dL to 4.5 g/dL, such as from 0.1 g/dL to 4 g/dL, such as from 0.25 g/dL to 3.5 g/dL, such as from 0.5 g/dL to 3 g/dL and including from 0.5 g/dL to 2 g/dL. Likewise, the value of C may also vary, ranging from 0.01 g/dL to 2 g/dL, such as from 0.025 g/dL to 1.75 g/dL, such as from 0.05 g/dL to 1.5 g/dL, such as from 0.1 g/dL to 1.25 g/dL and including from 0.25 g/dL to 2 g/dL.

As discussed above, in certain embodiments the sample is whole blood and the analyte of interest is hemoglobin. In some instances, methods include calculating concentration of total hemoglobin in whole blood while accounting for scatter by the sample by measuring transmitted light at a first and a second wavelength. The first wavelength may be a wavelength where hemoglobin has a high molar absorptivity. In some instances, the first wavelength may be an isosbestic point for hemoglobin with one or more of oxyhemoglobin, carboxyhemoglobin, methemoglobin, sulfo-hemoglobin, azide-methemoglobin and cyano-methemoglobin, such as a isosbestic point for hemoglobin and oxyhemoglobin or a triple isosbestic point for hemoglobin, oxyhemoglobin and carboxyhemoglobin. For example, a first wavelength is, in certain instances, 506 nm, 548 nm, 569 nm, 579 nm, 585 nm or 586 nm. To account for scatter, a second wavelength where hemoglobin has low absorptivity may be chosen, such as a near infrared wavelength. In some instances, the second wavelength is an isosbestic point for hemoglobin with one or more of oxyhemoglobin, carboxyhemoglobin, methemoglobin, sulfo-hemoglobin, azide-methemoglobin and cyano-methemoglobin, such as a isosbestic point for hemoglobin and oxyhemoglobin or a triple isosbestic point for hemoglobin, oxyhemoglobin and carboxyhemoglobin. For example, a second wavelength is, in certain instances, 650 nm, 675 nm, 710 nm, 785 nm, 808 nm, 815 nm or 830 nm.

For example, where the first wavelength is 548 nm and the second wavelength is 675 nm, to calculate concentration of hemoglobin accounting for scatter:

$$\text{Concentration}_{Hb} = A^*(\text{Abs}_{548\ nm}) + B^*(\text{Abs}_{675\ nm}) + C,$$

In embodiments, the value of A for a whole blood sample may vary, in certain instances, ranging from 20 g/dL to 60 g/dL, such as from 25 g/dL to 57.5 g/dL, such as from 30 g/dL to 55 g/dL, such as from 35 g/dL to 50 g/dL and including from 37.5 g/dL to 45 g/dL. The value of B for a whole blood sample may also vary, in certain instances, ranging from 0.01 g/dL to 5 g/dL, such as from 0.05 g/dL to 4.5 g/dL, such as from 0.1 g/dL to 4 g/dL, such as from 0.25 g/dL to 3.5 g/dL, such as from 0.5 g/dL to 3 g/dL and including from 0.5 g/dL to 2 g/dL. Likewise, the value of C of a whole blood sample may also vary, ranging from 0.01 g/dL to 2 g/dL, such as from 0.025 g/dL to 1.75 g/dL, such as from 0.05 g/dL to 1.5 g/dL, such as from 0.1 g/dL to 1.25 g/dL and including from 0.25 g/dL to 2 g/dL.

In another example, where the first wavelength is 548 nm and the second wavelength is 650 nm, to calculate concentration of hemoglobin accounting for scatter:

$$\text{Concentration}_{Hb} = A*(\text{Abs}_{548\ nm}) + B*(\text{Abs}_{650\ nm}) + C,$$

In embodiments, the value of A for a whole blood sample may vary, in certain instances, ranging from 20 g/dL to 60 g/dL, such as from 25 g/dL to 57.5 g/dL, such as from 30 g/dL to 55 g/dL, such as from 35 g/dL to 50 g/dL and including from 37.5 g/dL to 45 g/dL. The value of B for a whole blood sample may also vary, in certain instances, ranging from 0.01 g/dL to 5 g/dL, such as from 0.05 g/dL to 4.5 g/dL, such as from 0.1 g/dL to 4 g/dL, such as from 0.25 g/dL to 3.5 g/dL, such as from 0.5 g/dL to 3 g/dL and including from 0.5 g/dL to 2 g/dL. Likewise, the value of C of a whole blood sample may also vary, ranging from 0.01 g/dL to 2 g/dL, such as from 0.025 g/dL to 1.75 g/dL, such as from 0.05 g/dL to 1.5 g/dL, such as from 0.1 g/dL to 1.25 g/dL and including from 0.25 g/dL to 2 g/dL.

In another embodiment, methods include calculating concentration of the analyte while accounting for interferents by measuring the transmitted light and determining the absorbance at a first wavelength and a second wavelength. In this embodiment, a concentration of the analyte is calculated by determining the concentration from the absorbance at the first wavelength and determining the concentration from the absorbance at the second wavelength and subtracting the concentration obtained at second wavelength from the concentration at the first wavelength.

In certain embodiments, the subject methods may be coupled with methods for interrogating the sample for one or more analytes by a fluorescence assay. For example, as described in greater detail below, the sample may be contacted with one or more reagents having fluorescent markers, the emission being detectable by one or more photosensors or photodetectors. As such, aspects of the present disclosure according to certain embodiments include assaying a sample for one or more analytes by contacting the sample with one or more reagents and optically interrogating the sample by an absorption assay (as discussed above) in combination with a fluorescence assay.

In embodiments, samples assayed for fluorescence may be illuminated with one or more light sources. Depending on the target analyte, the sample may be illuminated with one or more broadband light sources (e.g., a halogen lamp, deuterium arc lamp, xenon arc lamp, stabilized fiber-coupled broadband light source, a broadband LED with continuous spectrum, superluminescent emitting diode, semiconductor light emitting diode, wide spectrum LED white light source, an multi-LED integrated white light source, combinations thereof, as described above) or may be illuminated with one or more narrow band light sources emitting a particular wavelength or narrow range of wavelengths (e.g., narrow wavelength LED, laser diode or a broadband light source coupled to one or more optical bandpass filters, diffraction gratings, monochromators, combination thereof, as described above).

Depending on the dimensions and positioning of the sample chamber, the angle of incident illumination for fluorescence assay may vary, ranging from 30° to 60° with respect to the plane of the sample chamber, such as from 35° to 55°, such as from 40° to 50° and including illuminating the sample chamber at a 45° with respect to the plane of the sample chamber.

Where more than one light source is employed, the sample may be illuminated with the light sources simultaneously or sequentially, or a combination thereof. Where the sample is sequentially illuminated with two or more light sources, the time each light source illuminates the same may independently be 0.001 seconds or more, such as 0.01 seconds or more, such as 0.1 seconds or more, such as 1 second or more, such as 5 seconds or more, such as 10 seconds or more, such as 30 seconds or more and including 60 seconds or more. In embodiments where the sample is sequentially illuminated by two or more light sources, the duration the sample is illuminated by each light source may be the same or different. The time period between illumination by each light source may also vary, as desired, being separated independently by a delay of 1 second or more, such as 5 seconds or more, such as by 10 seconds or more, such as by 15 seconds or more, such as by 30 seconds or more and including by 60 seconds or more.

Depending on the specific analytes being assayed as well as the reagents and fluorescent markers employed, illumination of the sample may be continuous or in discrete intervals. For example, in some embodiments, the sample may be illuminated continuously throughout the entire time the sample is being assayed. In other embodiments, the sample may be illuminated in regular intervals, such as illuminating the sample every 0.001 microseconds, every 0.01 microseconds, every 0.1 microseconds, every 1 microsecond, every 10 microseconds, every 100 microseconds and including every 1000 microseconds. The sample may be illuminated with the light source one or more times at any given measurement period, such as 2 or more times, such as 3 or more times, including 5 or more times at each measurement period.

During fluorescence assay, the sample may be illuminated with a broadband light source having wavelengths ranging from 300 nm to 900 nm, such as from 325 nm to 875 nm, such as from 350 nm to 850 nm, such as from 375 nm to 825 nm and including from 400 nm to 800 nm or some other range. In other embodiments, the sample is illuminated with specific wavelengths of light or a narrow range of specific wavelengths (such as with a narrow band lamp or LED). For example, the sample may be illuminated for fluorescence with a narrow band light source or one or more monochromatic LEDs emitting light in the range of 450 nm to 700 nm, such as at 480 nm, 565 nm and 650 nm.

As the subject fluorescence assay is coupled with methods for absorption assay described above, emitted light from the sample may be collected, spatially separated into component wavelengths and detected in a similar manner as described above. As described in detail below, fluorescence detection systems and the absorbance detection systems employ one or more common components as described herein. For example, in some instances both fluorescence assay and absorbance assay employ a common objective lens module for collecting and focusing light from the sample chamber (e.g., emitted light or transmitted light). In other instances, both fluorescence assay and absorbance assay employ a common wavelength separation protocol (e.g., diffraction grating, optical filters, filter wheel having one or more diffraction gratings and optical filters) to spatially separate the collected light into component wavelengths. In yet other instances, both fluorescence assay and absorbance assay employ the same detection protocol for measuring light (e.g., emitted light or transmitted light) from the sample chamber.

In certain embodiments, the subject fluorescence assay may include methods for imaging samples in capillary channels such as those described in U.S. Pat. Nos. 8,248, 597; 7,927,561 and 7,738,094 as well as those described in co-pending U.S. patent application Ser. No. 13/590,114 filed Aug. 20, 2012, the disclosures of which are herein incorporated by reference.

In certain specific embodiments, the subject methods provide an absorbance assay for hemoglobin. As discussed above, hemoglobin may be present in any type of diagnostic sample, such as supernatants, lysates, buffered solution, as well as in biological samples including whole blood. In accordance with the methods described above, an amount of the sample is loaded into a sample chamber and illuminated through a slit projection module with one or more light sources, with light transmitted through the whole blood sample in the sample chamber being collected and spatially separated into component wavelengths for detection. Depending on the size of the whole blood sample, the sample chamber may be a microfluidic capillary channel sample chamber. Hemoglobin absorbance can be determined from the transmitted light at one or more wavelengths or alternatively, an entire spectrum of hemoglobin absorption may be calculated. Based on the absorbance at one or more wavelengths, the hemoglobin concentration in the whole blood sample can be determined in these embodiments of the subject methods.

In certain other specific embodiments, the subject methods provide a reagent free hemoglobin absorbance assay. By "reagent free" is meant that the assay of hemoglobin employs no reagents that interact or are used to visualize hemoglobin in the sample. As such, hemoglobin (including derivatives such oxy-hemoglobin and carboxyhemoglobin) is assayed in its native state without reagent modification. In these instances, an unaltered whole blood sample is loaded into a sample chamber and illuminated with one or more light sources through a slit projection module, with light transmitted through the whole blood sample in the sample chamber being collected and spatially separated into component wavelengths for detection. Depending on the size of the whole blood sample, the sample chamber may be a microfluidic capillary channel sample chamber. Hemoglobin absorbance can be detected at one or more wavelengths or alternatively, an entire spectrum of hemoglobin absorption may be calculated. Based on the absorbance at one or more wavelengths, the hemoglobin concentration in the unaltered whole blood sample can be determined in these embodiments of the subject methods.

In certain other specific embodiments, the subject methods provide a hemoglobin absorbance assay on a sample also being assayed for one or more additional analytes, such as for example cell surface markers. In these embodiments, one or more reagents, including specific binding members, enzymes, substrates, oxidizers as well as binding molecules coupled to one or more fluorescent markers are contacted with the whole blood and the reagent-mixed whole blood sample is loaded into a sample chamber. The loaded sample chamber (such as a microfluidic capillary channel sample chamber) is illuminated with one or more light sources through a slit projection module, with light transmitted through the whole blood sample in the sample chamber being collected and spatially separated into component wavelengths for detection. Hemoglobin absorbance can be detected at one or more wavelengths or alternatively, an entire spectrum of hemoglobin absorption may be calculated. Based on the absorbance at one or more wavelengths, the hemoglobin concentration in the reagent-mixed whole blood sample can be determined in these embodiments of the subject methods. In conjunction with assaying for hemoglobin in the reagent-mixed sample, one or more additional analytes may be assayed. In some instances, the subject methods provide a fluorescence assay performed in conjunction with the hemoglobin absorbance assay to assay for one or more cell surface markers binding to the one or more reagents mixed into the whole blood sample. In these instances, a fluorescence light source illuminates the sample chamber loaded with reagent-mixed whole blood sample and fluorescence emission from fluorescence tags bound to target analytes is collected and spatially separated for detection.

In certain other specific embodiments, the subject methods provide a hemoglobin absorbance assay on a sample for which is also fluorescence assayed for CD4 and % CD4. In these instances, the whole blood sample is applied to the sample application site of a microfluidic cartridge having a capillary channel sample chamber. The applied sample is carried through the inlet of the microfluidic capillary channel into a reagent mixing chamber having a porous disc for contacting the reagent mixture with the whole blood sample. The reagent mixture, in these instances, includes dried storage stable reagents CD4-PECy5, CD3-APC, CD45RA-APC and CD14-PE. The reagent mixed whole blood sample is carried by capillary action through to the sample chamber where the sample chamber is illuminated for hemoglobin assay by two light sources, a broadband white light LED and a near-infrared LED through a slit projection module which is moved laterally across the sample chamber. Light transmitted though the sample chamber is collected with an objective, magnifying lens and autofocused onto a diffraction grating to spatially separate the transmitted light on the surface of a CCD detector. The absorbance at two wavelengths, 548 nm and 675 nm are determined and the total hemoglobin absorbance accounting for scatter is calculated to assay for hemoglobin.

The reagent mixed whole blood sample in the capillary channel sample chamber is also assayed for CD4 by detecting fluorescence by fluorescent tags in the reagent mixture. CD4 may be assayed for by illuminating the reagent mixed whole blood sample in the capillary channel sample chamber with a light source and emission from the fluorescent tags in the reagent mixed whole blood sample is collected with a common objective, magnifying lens and autofocused onto the surface of the CDD detector. CD4 cell counting is then conducted by fluorescent image cytometry.

In certain embodiments, aspects of the methods include applying a sample to a microfluidic device configured to perform an assay of a liquid sample having a sample application site, an inlet for inputting the sample from the sample application site, a reagent contacting chamber for contacting the sample with one or more reagents and a capillary sample chamber in fluid communication with the reagent contacting chamber.

In some embodiments, the sample is applied to the application site of the microfluidic device and allowed to flow through the inlet and into the reagent contacting chamber, followed by flow through the capillary sample chamber such that sufficient sample is provided to be interrogated in the capillary sample chamber as described above.

In certain instances, methods include providing a sample contacted sample application site of the microfluidic device. By "sample-contacted sample application site" is meant a sample application site that has been contacted by the sample. In practicing methods of the present disclosure, a sample-contacted application site is provided by applying a sample to the sample application site of the microfluidic device. The amount of sample that is applied to the sample application site may vary, so long as it is sufficient to provide desired capillary flow through the sample chamber and adequate sample for interrogation by the subject methods described herein. For example, the amount of sample applied to the application site may range from 0.01 µL to 1000 µL, such as from 0.05 µL to 900 µL, such as from 0.1 µL to 800 µL, such as from 0.5 µL to 700 µL, such as from 1 µL to 600 µL, such as from 2.5 µL to 500 µL, such as from 5 µL to 400 µL, such as from 7.5 µL to 300 µL and including from 10 µL to 200 µL of sample.

The sample may be applied to the sample application site using any convenient protocol, e.g., via dropper, pipette, syringe and the like. The sample may be applied in conjunction or incorporated into a quantity of a suitable liquid, e.g., buffer, to provide for adequate fluid flow. Any suitable liquid may be employed, including but not limited to buffers, cell culture media (e.g., DMEM), etc. Buffers include, but are not limited to: tris, tricine, MOPS, HEPES, PIPES, MES, PBS, TBS, and the like. Where desired, detergents may be present in the liquid, e.g., NP-40, TWEEN™ or TritonX100 detergents.

In certain embodiments, the sample-contacted sample application site is provided by combining the sample with one or more assay components (e.g., a reagent, a buffer, and the like) prior to applying the sample which has the assay component(s) to the sample application site. When the sample is combined with one or more assay components prior to the application of the sample having the assay component(s) to the sample application site, the combination may be achieved using any convenient protocol. The amount of an assay component(s), when combined with the sample, may vary as desired. In some embodiments, the sample-contacted sample application site is provided by applying one or more assay components to the sample receiving application site prior to applying the sample to the sample application site. In some embodiments, the sample-contacted sample application site is provided by applying the sample to the sample application site prior to applying one or more assay components to the sample application site. As mentioned above, in some embodiments, the device includes one or more assay components (e.g., reagent). In such cases, the sample-contacted sample application site is provided by applying the sample to the sample application site, e.g., without prior combination with one or more assay components.

Following sample application, the sample is allowed to flow through the capillary sample chamber, and one or more portions of the channel, e.g., the detection region, including the entire channel, is then interrogated assay for the target analyte(s) in the sample. Depending on the target analyte and presence of one or more reagents, the sample may be interrogated immediately after sample application or following a predetermined period of time after sample application, such as a period of time ranging from 10 seconds to 1 hour, such as 30 seconds to 30 minutes, e.g., 30 seconds to 10 minutes, including 30 seconds to 1 minute.

One example of suitable methods and microfluidic devices for preparing a sample for interrogation by the subject methods may include, but are not limited to those described in copending U.S. patent application Ser. No. 14/152,954 filed on Jan. 10, 2014, the disclosure of which is herein incorporated by reference.

Systems for Assaying a Sample for an Analyte

Aspects of the present disclosure further include systems for practicing the subject methods. In embodiments, systems which include a light source, a slit projection module (e.g., a slit for narrowing a beam of light or a slit coupled to a focusing lens that focuses the narrowed light) and a detector for detecting one or more wavelengths of the transmitted light are provided. In certain embodiments, systems further include a microfluidic device for preparing and providing the sample for assay using the subject systems.

As summarized above, aspects of the present disclosure include assaying a sample for one or more analytes. Systems include one or more light sources for interrogating a sample chamber containing a sample of interest. In some embodiments, the light source is a broadband light source, emitting light having a broad range of wavelengths, such as for example, spanning 50 nm or more, such as 100 nm or more, such as 150 nm or more, such as 200 nm or more, such as 250 nm or more, such as 300 nm or more, such as 350 nm or more, such as 400 nm or more and including spanning 500 nm or more. For example, one suitable broadband light source emits light having wavelengths from 400 nm to 800 nm. Another example of a suitable broadband light source includes a light source that emits light having wavelengths from 500 nm to 700 nm. Any convenient broadband light source protocol may be employed, such as a halogen lamp, deuterium arc lamp, xenon arc lamp, stabilized fiber-coupled broadband light source, a broadband LED with continuous spectrum, superluminescent emitting diode, semiconductor light emitting diode, wide spectrum LED white light source, an multi-LED integrated white light source, among other broadband light sources or any combination thereof.

In other embodiments, the light source is a narrow band light source emitting a particular wavelength or a narrow range of wavelengths. In some instances, the narrow band light sources emit light having a narrow range of wavelengths, such as for example, 50 nm or less, such as 40 nm or less, such as 30 nm or less, such as 25 nm or less, such as 20 nm or less, such as 15 nm or less, such as 10 nm or less, such as 5 nm or less, such as 2 nm or less and including light sources which emit a specific wavelength of light (i.e., monochromatic light). Any convenient narrow band light source protocol may be employed, such as a narrow wavelength LED, laser diode or a broadband light source coupled to one or more optical bandpass filters, diffraction gratings, monochromators or any combination thereof.

The subject systems may include one or more light sources, as desired, such as two or more light sources, such as three or more light sources, such as four or more light sources, such as five or more light sources and including ten or more light sources. The light source may include an combination of types of light sources, for example, where two lights sources are employed, a first light source may be a broadband white light source (e.g., broadband white light LED) and second light source may be a broadband near-infrared light source (e.g., broadband near-IR LED). In other instances, where two light sources are employed, a first light source may be a broadband white light source (e.g., broadband white light LED) and the second light source may be a narrow spectra light source (e.g., a narrow band visible light or near-IR LED). In yet other instances, the light source is an plurality of narrow band light sources each emitting specific wavelengths, such as an array of two or more LEDs, such as an array of three or more LEDs, such as an array of five or more LEDs, including an array of ten or more LEDs.

In some embodiments, light sources emit light having wavelengths ranging from 400 nm to 900 nm, such as from 450 nm to 850 nm, such as from 500 nm to 800 nm, such as from 550 nm to 750 nm and including from 600 nm to 700 nm. For example, the light source may include a broadband light source emitting light having wavelengths from 400 nm to 900 nm. In other instances, the light source includes a plurality of narrow band light sources emitting wavelengths ranging from 400 nm to 900 nm. For example, the light source may be plurality of narrow band LEDs (1 nm-25 nm) each independently emitting light having a range of wavelengths between 400 nm to 900 nm.

In certain embodiments, systems include two broadband light sources, configured to collectively emit light having wavelengths ranging from 400 nm to 900 nm. For example, the light sources may be a white light LED emitting light having wavelengths ranging from 400 nm to 700 nm and a near-infrared LED emitting light having wavelengths ranging from 700 nm to 900 nm. In some embodiments, the irradiation profile of each light source may vary, having any number of emission peaks. In certain instances, the light source includes a white light LED emitting light having wavelengths ranging from 400 nm to 700 nm and having emission peaks at about 450 nm and 550 nm and a near-infrared LED emitting light having wavelengths ranging from 700 nm to 900 nm and having an emission peak at about 830 nm.

In other embodiments, the light source is a plurality of narrow band lamps or LEDs each independently emitting specific wavelengths of light in the range of 400 nm to 900 nm. In one example, the narrow band light source is one or more monochromatic LEDs emitting light in the range of 500 nm to 700 nm, such as at 504 nm, 506 nm, 514 nm, 532 nm, 543 nm, 548 nm, 550 nm, 561 nm, 568 nm, 579 nm, 580 nm, 585 nm, 586 nm or any combination thereof. In another example, the narrow band light source is an array of LEDs emitting light with wavelengths ranging from 400 nm to 900 nm. In another example, the narrow band light source is one or more narrow band lamps emitting light in the range of 500 nm to 700 nm, such as a narrow band cadmium lamp, cesium lamp, helium lamp, mercury lamp, mercury-cadmium lamp, potassium lamp, sodium lamp, neon lamp, zinc lamp or any combination thereof.

As summarized above, systems include a slit projection module configured to narrow a beam of light and produce a beam of light in the shape of a slit projected onto the sample chamber. In some embodiments, the slit projection module includes a slit. In other embodiments, the slit projection module includes a slit coupled to a focusing lens configured to focus the narrow slit-shaped beam of light at the sample chamber.

In some embodiments, systems of the present disclosure are configured such that the sample chamber, the slit projection module or both the sample chamber and slit projection module may be moved to displace the slit-shaped beam of light across the sample chamber. Where movement of the slit-shaped beam of light across the sample chamber is desired, in some embodiments systems are configured to move the sample chamber while the slit-projection module is maintained in a stationary position. In other embodiments, systems are configured to move the slit-projection and the sample chamber is maintained in a stationary. In yet other embodiments, the system is configured to move both the slit projection module and the sample chamber. Any displacement protocol may be employed in the subject systems to move the slit-shaped beam of light across the sample chamber, such as manually (i.e., movement of the sample chamber or slit projection module directly by hand), with assistance by a mechanical device or by a motor actuated displacement device. For example, in some embodiments the sample chamber is moved in the subject systems with a mechanically actuated translation stage, mechanical leadscrew assembly, mechanical slide device, mechanical lateral motion device, mechanically operated geared translation device. In other embodiments, the sample chamber is moved with a motor actuated translation stage, leadscrew translation assembly, geared translation device, such as those employing a stepper motor, servo motor, brushless electric motor, brushed DC motor, micro-step drive motor, high resolution stepper motor, among other types of motors. In certain instances, the sample chamber is housed in a cartridge holder which is operably or mechanically connected to the translation or displacement device. In these instances, the sample chamber (or microcartridge containing the sample chamber) is first loaded into the cartridge housing and the entire housing is displaced during the subject methods.

Likewise, the slit projection module, in certain instances, is moved in the subject systems with a mechanically actuated translation stage, mechanical leadscrew assembly, mechanical slide device, mechanical lateral motion device, mechanically operated geared translation device. In other embodiments, the slit projection module is moved with a motor-actuated translation stage, leadscrew translation assembly, geared translation device, such as those employing a stepper motor, servo motor, brushless electric motor, brushed DC motor, micro-step drive motor, high resolution stepper motor, among other types of motors.

In some embodiments, the system is configured to move the sample chamber relative to a stationary slit projection module to displace the slit-shaped beam laterally across the sample chamber in a single direction during interrogation of the sample. In other embodiments, the system is configured to move the sample chamber relative to a stationary slit projection module to displace the slit-shaped beam laterally across the sample chamber in back-and-forth motion during interrogation of the sample. For example, the sample chamber may be moved such that the slit-shaped beam is moved along 50% or more of the sample chamber, such as 55% or more, such as 60% or more, such as 65% or more, such as 70% or more, such as 75% or more, such as 80% or more, such as 85% or more, such as 90% or more, such as 95% or more, such as 97% or more and including along 99% or more of the length of the sample chamber. In certain instances, the sample chamber is moved such that slit-shaped beam is moved along substantially the entire length of the sample chamber.

In other embodiments, the system is configured to move the slit projection module relative to a stationary sample chamber to displace the slit-shaped beam laterally across the sample chamber in a single direction during interrogation of the sample. In other embodiments, the system is configured to move the slit projection module relative to a stationary sample chamber to displace the slit-shaped beam laterally across the sample chamber in back-and-forth motion during interrogation of the sample. For example, the slit projection module may be moved such that the slit-shaped beam is moved along 50% or more of the sample chamber, such as 55% or more, such as 60% or more, such as 65% or more, such as 70% or more, such as 75% or more, such as 80% or more, such as 85% or more, such as 90% or more, such as 95% or more, such as 97% or more and including along 99% or more of the length of the sample chamber. In certain instances, the slit projection module is moved such that slit-shaped beam is moved along substantially the entire length of the sample chamber. In yet other embodiments, the system is configured to move both the slit projection module and the sample chamber to displace the slit-shaped beam laterally across the sample chamber in a single direction during interrogation of the sample. In other embodiments, the system is configured to move both the slit projection module and sample chamber to displace the slit-shaped beam laterally across the sample chamber in back-and-forth motion during interrogation of the sample. For example, the slit projection module and the sample chamber may be both moved such that the slit-shaped beam is moved along 50% or more of the sample chamber, such as 55% or more, such as 60% or more, such as 65% or more, such as 70% or more, such as 75% or more, such as 80% or more, such as 85% or more, such as 90% or more, such as 95% or more, such as 97% or more and including along 99% or more of the length of the sample chamber. In certain instances, the slit projection module and sample chamber are both moved such that slit-shaped beam is moved along substantially the entire length of the sample chamber.

The slit aperture may be any convenient shape, including but not limited to an oval, rectangle or other suitable polygon. In certain embodiments, the slit aperture is rectangular. Depending on the size of the sample chamber and slit-shaped beam provided by the light source as well as the distance between the slit projection module, light source, sample chamber and detector, the dimensions of the slit aperture may vary, having a length which ranges from 1 mm to 10 mm, such as from 1.25 mm to 9.5 mm, such as from 1.5 mm to 9 mm, such as from 2 mm to 8 mm, such as from 2.5 mm to 7 mm, such as from 3 mm to 6 mm and including from 3.5 mm to 5 mm. The width of the slit aperture may range from 1 µm to 250 µm, such as from 2 µm to 225 µm, such as from 5 µm to 200 µm, such as from 10 µm to 150 µm, and including from 15 µm to 125 µm, for example a slit having an aperture width of 100 µm. Any convenient slit device may be employed so long as it is sufficient to provide the desired slit-shaped beam of light for interrogating the sample chamber. For example, the slit may be gold, silver, gold-plated copper, ceramic, chromium, copper, molybdenum and tungsten.

In some instances, the slit projection module also includes an optical adjustment protocol. By "optical adjustment" is meant that the beam of light in the shape of a slit may be changed as desired, such as to increase or decrease the dimensions or to enhance the optical resolution of the slit shaped beam. In some instances, optical adjustment is a magnification protocol configured to increase the width of the slit, such as by 5% or greater, such as by 10% or greater, such as by 25% or greater, such as by 50% or greater and including increasing the width of the slit shaped beam by 75% or greater. In other instances, optical adjustment is a de-magnification protocol configured to decrease the width of the slit, such as by 5% or greater, such as by 10% or greater, such as by 25% or greater, such as by 50% or greater and including decreasing the width of the slit shaped beam by 75% or greater. In certain embodiments, optical adjustment is an enhanced resolution protocol configured to improve the resolution of the slit shaped beam, such as by 5% or greater, such as by 10% or greater, such as by 25% or greater, such as by 50% or greater and including enhancing the resolution of the slit shaped beam by 75% or greater. The slit shaped beam may be adjusted with any convenient optical adjustment protocol, including but not limited to lens, mirrors, pinholes, slits, and combinations thereof.

In certain embodiments, the slit projection module may also include a focusing lens coupled to the slit that is configured to focus the narrowed slit-shaped beam of light. In some embodiments, the focusing lens is a de-magnifying lens having a magnification ratio ranging from 0.1 to 0.95, such as a magnification ratio of from 0.2 to 0.9, such as a magnification ratio of from 0.3 to 0.85, such as a magnification ratio of from 0.35 to 0.8, such as a magnification ratio of from 0.5 to 0.75 and including a magnification ratio of from 0.55 to 0.7, for example a magnification ratio of 0.6. For example, the focusing lens is, in certain instances, a double achromatic de-magnifying lens having a magnification ratio of about 0.6. Depending on the distance between the slit projection module, light source, sample chamber and detector as well as the size of the sample chamber and desired size of slit-shaped beam, the focal length of the focusing lens may vary, ranging from 5 mm to 20 mm, such as from 6 mm to 19 mm, such as from 7 mm to 18 mm, such as from 8 mm to 17 mm, such as from 9 mm to 16 mm and including a focal length ranging from 10 mm to 15 mm. In certain embodiments, the focusing lens has a focal length of about 13 mm.

In some embodiments, the slit and the focusing lens are in optical communication, but are not physically in contact. Depending on the size of the sample chamber as well as the desired shape and size of the slit-shaped beam projected onto the sample chamber, the slit may be positioned a distance from the focusing lens which varies and may be 0.1 mm or more, such as 0.2 mm or more, such as 0.5 mm or more, such as 1 mm or more, such as 5 mm or more, such as 10 mm or more, such as 25 mm or more, such as 50 mm or more, including 100 mm or more. In other embodiments, the slit is physically coupled to the focusing lens, such as with an adhesive, co-molded together or integrated together in a housing having the focusing lens positioned adjacent to the slit. As such, the slit and focusing lens may be integrated into a single unit.

As described above, the slit projection module is configured to provide a slit-shaped beam having a length and width which varies. In some embodiments, the slit projection module is configured to provide a slit-shaped beam having a length which ranges from 1 mm to 5 mm, such as from 1.5 mm to 4.5 mm, such as from 2 mm to 4 mm, such as from 2.5 mm to 3.5 mm and including a slit-shaped beam having a length of 3 mm. In these embodiments, the slit projection module is configured to provide a slit-shaped beam having a width which ranges from 10 µm to 100 µm, such as from 15 µm to 95 µm, such as from 20 µm to 90 µm, such as from 25 µm to 85 µm, such as from 30 µm to 80 µm, such as from 35 µm to 75 µm, such as from 40 µm to 70 µm, such as from 45 µm to 65 µm, and including from 50 µm to 60 µm.

As described above, in some embodiments the slit projection module is configured to provide a slit-shaped beam having a length that is orthogonal to the length of the sample chamber. Depending on the size of the sample chamber, as described below, the slit-projection module may be configured to provide a slit-shaped beam having a length that is 50% or more of the width of the sample chamber, such as 55% or more, such as 60% or more, such as 65% or more, such as 70% or more, such as 75% or more, such as 80% or more, such as 85% or more, such as 90% or more, such as 95% or more, such as 97% or more and including a slit projection module configured to provide a slit-shaped beam having a length that is 99% or more of the width of the sample chamber. In certain instances, the slit projection module is configured to provide a slit-shaped beam that has a length which is substantially the same as width of the sample chamber. In other embodiments, the slit-projection module is configured to provide a slit-shaped beam projection which has a length that is greater than the width of the sample chamber. For example, the slit projection module is, in certain instances, configured to provide a slit-shaped beam of light that has a length which is 1% or greater than the width of the sample chamber, such as 2% or greater, such as 5% or greater, such as 10% or greater, such as 15% or greater, such as 20% or greater and including a length which is 25% greater than the width of the sample chamber. In yet other instances, the slit projection module is configured to provide a slit-shaped beam of light that has a length which is less than the width of the sample chamber, such as a length that is 1% or greater less than the width of the sample chamber, such as a length that is 2% or greater less than the width of the sample chamber, such as a length that is 5% or greater less than the width of the sample chamber, such as a length that is 10% or greater less than the width of the sample chamber, such as a length that is 15% or greater less than the width of the sample chamber, such as a length that is 20% or greater less than the width of the sample chamber and including a length that 25% or greater less than the width of the sample chamber.

As discussed in greater detail below, in certain embodiments the subject systems are configured to receive a microfluidic cartridge device having a capillary sample chamber. In these embodiments, systems may also include a cartridge holder for receiving the cartridge into the system For example, the cartridge holder may include a support for receiving the microfluidic cartridge device and one or more cartridge retainers for maintaining the microfluidic cartridge device in the cartridge holder. In some instances, the cartridge holder includes vibration dampers for reducing agitation of the microfluidic cartridge device positioned in the cartridge holder as well as one or more cartridge presence flags configured to indicate that a microfluidic cartridge device is present in the cartridge holder.

Where the subject systems are configured to move the sample chamber during interrogation (as discussed above), systems may also include a cartridge shuttle coupled to the cartridge holder for moving the microfluidic cartridge device. In some embodiments, the cartridge shuttle is coupled to one or more translation or lateral movement protocols to move the microfluidic cartridge device. For example, the cartridge shuttle may be coupled to a mechanically actuated translation stage, mechanical leadscrew assembly, mechanical slide device, mechanical lateral motion device, mechanically operated geared translation device, a motor-actuated translation stage, leadscrew translation assembly, geared translation device, such as those employing a stepper motor, servo motor, brushless electric motor, brushed DC motor, micro-step drive motor, high resolution stepper motor, among other types of motors. Systems may also include a set of rails for positioning the cartridge shuttle to facilitate lateral movement of the cartridge holder.

In some embodiments, systems further include a blank reference window to provide a blank absorbance for use in calculating analyte concentration. The absorbance by the blank reference window is in certain embodiments, configured to be identical to absorbance by the sample chamber such that transmission through the blank reference window can be used to correct for absorption, scatter, etc. by the microfluidic cartridge when practicing the methods described herein. In certain embodiments, the blank reference window has an absorbance and transmission at the one or more wavelengths of incident light which is substantially the same as the capillary channel sample chamber. In other embodiments, the blank reference window scatters light at the one or more wavelengths which is substantially the same as the capillary channel sample chamber. In yet other embodiments, the blank reference window has an absorbance, transmission and scatters light at the one or more incident wavelengths which is substantially the same as the capillary channel sample chamber. In still other embodiments, the blank reference window has an index of refraction which is the same as the capillary channel sample chamber.

The blank reference window integrated into the subject systems may be any convenient size and shape. For example, the blank reference window may be in the form of a square, circle, oval, rectangle, pentagon, hexagon, octagon or any other suitable polygon. In some embodiments, the blank reference window has a ratio of length to width which ranges from 1 to 50, such as 3 to 25, such as from 4 to 10, such as from 5 to 8, including 15 to 20. In certain embodiments, the blank reference window is a square and has a ratio of length to width of 1. The length of the blank reference window may vary, ranging from 1 mm to 50 mm, such as 2 mm to 25 mm and including 5 mm to 20 mm. The width of the blank reference window may vary, ranging from 0.001 mm to 20 mm, such as from 0.005 mm to 19 mm, such as from 0.01 mm to 18 mm, such as from 0.05 mm to 17 mm, such as from 0.1 mm to 15 mm, such as from 0.5 mm to 12.5 mm, such as 1 to 10 and including 3 to 5 mm. In some instances the height of the channel ranges from 5 μm to 500 μm, such as 10 μm to 150 μm and including 20 μm to 70 μm. In certain embodiments, the blank reference window has a width which is substantially the same as the width of the capillary channel sample chamber. As described above, the slit-shaped beam of light that is transmitted through the sample chamber is collected and detected using one or photodetectors. In certain embodiments, systems include one or more objective lenses for collecting light transmitted through the sample chamber. For example, the objective lens may be a magnifying lens with a nominal magnification ranging from 1.2 to 2.5, such as a nominal magnification of from 1.3 to 2.4, such as a nominal magnification of from 1.4 to 2.3, such as a nominal magnification of from 1.5 to 2.2, such as a nominal magnification or from 1.6 to 2.1, including passing the transmitted light through a magnifying lens having a nominal magnification of from 1.7 to 2.0, for example a nominal magnification of 1.7. In certain instances, the objective lens is a magnifying achromatic doublet lens with a nominal magnification of 1.7. Depending on the configuration of the light source, sample chamber and detector, properties of the objective lens may vary. For example, the numerical aperture of the subject objective lens may also vary, ranging from 0.01 to 1.7, such as from 0.05 to 1.6, such as from 0.1 to 1.5, such as from 0.2 to 1.4, such as from 0.3 to 1.3, such as from 0.4 to 1.2, such as from 0.5 to 1.1 and including a numerical aperture ranging from 0.6 to 1.0. Likewise, the focal length of the objective lens varies, ranging from 10 mm to 20 mm, such as from 10.5 mm to 19 mm, such as from 11 mm to 18 mm and including from 12 mm to 15 mm.

In some embodiments, the objective lens is coupled to an autofocus module for focusing the slit-shaped beam projection transmitted through the sample chamber onto the detector for detection. For example, a suitable autofocus module for focusing the slit-shaped beam projection transmitted through the sample may include, but is not limited, to those described in U.S. Pat. No. 6,441,894, filed on Oct. 29, 1999, the disclosure of which is herein incorporated by reference.

Systems of the present disclosure may also include one or more wavelength separators. As discussed above, a "wavelength separator" is configured to separate polychromatic light into component wavelengths such that each wavelength may be suitably detected. Examples of suitable wavelength separators in the subject systems may include but are not limited to colored glass, bandpass filters, interference filters, dichroic mirrors, diffraction gratings, monochromators and combinations thereof, among other wavelength separating protocols. Depending on the light source and sample being assayed, systems may include one or more wavelength separators, such as two or more, such as three or more, such as four or more, such as five or more and including 10 or more wavelength separators. In one example, systems include two or more bandpass filters. In another example, systems include two or more bandpass filters and a diffraction grating. In yet another example, systems include a plurality of bandpass filters and a monochromator. In certain embodiments, systems include a plurality of bandpass filters and diffraction gratings configured into a filter wheel setup. Where systems include two or more wavelength separators, the wavelength separators may be utilized individually or in series to separate polychromatic light into component wavelengths. In some embodiments, wavelength separators are arranged in series. In other embodiments, wavelength separators are arranged individually such that one or more measurements are conducted to collect the desired absorbance data using each of the wavelength separators.

In some embodiments, systems include one or more diffraction gratings. Diffraction gratings of interest may include, but are not limited to transmission, dispersive or reflective diffraction gratings. Suitable spacings of the diffraction grating may vary depending on the configuration of the light source, slit projection module, sample chamber, objective lens, ranging from 0.01 µm to 10 µm, such as from 0.025 µm to 7.5 µm, such as from 0.5 µm to 5 µm, such as from 0.75 µm to 4 µm, such as from 1 µm to 3.5 µm and including from 1.5 µm to 3.5 µm.

In some embodiments, systems include one or more optical filters. In certain instances, systems include bandpass filters having minimum bandwidths ranging from 2 nm to 100 nm, such as from 3 nm to 95 nm, such as from 5 nm to 95 nm, such as from 10 nm to 90 nm, such as from 12 nm to 85 nm, such as from 15 nm to 80 nm and including bandpass filters having minimum bandwidths ranging from 20 nm to 50 nm. For example, systems may include one or more bandpass filters which selectively pass wavelengths in the ranges of: 498 nm-510 nm; 500 nm-600 nm; 500 nm-520 nm; 540 nm-550 nm; 545 nm-555 nm; 550 nm-570 nm; 550 nm-580 nm; 560 nm-590 nm; 575 nm-595 nm; 580 nm-590 nm; 600 nm-700 nm; 600 nm-630 nm; 650 nm-750 nm; 750 nm-850 nm; 810 nm-830 nm; 815 nm-825 nm or any combination thereof.

In certain instances, systems include one or more bandpass filters which selectively pass wavelengths ranging from 500 nm-520 nm and from 650 nm-750 nm. In other instances, systems include one or more bandpass filters which selectively pass wavelengths ranging from 540 nm-560 nm and from 650 nm-750 nm. In yet other instances, systems include one or more bandpass filters which selectively pass wavelengths ranging from 560 nm-590 nm and from 650 nm-750 nm. In still other instances, systems include one or more bandpass filters which selectively pass wavelengths ranging from 500 nm-520 nm; 560 nm-590 nm and from 650 nm-750 nm.

Systems of the present disclosure also include one or more detectors. Examples of suitable detectors may include, but are not limited to optical sensor or photodetectors, such as active-pixel sensors (APSs), avalanche photodiode, image sensors, charge-coupled devices (CCDs), intensified charge-coupled devices (ICCDs), light emitting diodes, photon counters, bolometers, pyroelectric detectors, photoresistors, photovoltaic cells, photodiodes, photomultiplier tubes, phototransistors, quantum dot photoconductors or photodiodes and combinations thereof, among other photodetectors. In certain embodiments, the transmitted light is measured with a charge-coupled device (CCD). Where the transmitted light is measured with a CCD, the active detecting surface area of the CCD may vary, such as from 0.01 $cm^2$ to 10 $cm^2$, such as from 0.05 $cm^2$ to 9 $cm^2$, such as from, such as from 0.1 $cm^2$ to 8 $cm^2$, such as from 0.5 $cm^2$ to 7 $cm^2$ and including from 1 $cm^2$ to 5 $cm^2$.

In embodiments of the present disclosure, detectors of interest are configured to measure light transmitted through the sample chamber at one or more wavelengths, such as at 2 or more wavelengths, such as at 5 or more different wavelengths, such as at 10 or more different wavelengths, such as at 25 or more different wavelengths, such as at 50 or more different wavelengths, such as at 100 or more different wavelengths, such as at 200 or more different wavelengths, such as at 300 or more different wavelengths and including measuring the light transmitted through the sample chamber at 400 or more different wavelengths.

In some embodiments, detectors of interest are configured to measure light transmitted through the sample chamber over a range of wavelengths (e.g., 400 nm-800 nm; 495 nm-525 nm; 800 nm-835 nm, etc.). For example, systems may include one or more detectors configured to measure light transmitted through the sample chamber over one or more of the wavelength ranges of: 400 nm-800 nm; 498 nm-510 nm; 500 nm-600 nm; 500 nm-700 nm; 500 nm-520 nm; 540 nm-550 nm; 545 nm-555 nm; 550 nm-570 nm; 550 nm-580 nm; 560 nm-590 nm; 575 nm-595 nm; 580 nm-590 nm; 600 nm-700 nm; 600 nm-630 nm; 650 nm-750 nm; 750 nm-850 nm; 810 nm-830 nm; 815 nm-825 nm and any combinations thereof. In certain instances, the detector is configured to measure transmitted light over the wavelengths ranging from 400 nm-800 nm. In other instances, the detector is configured to measure transmitted light over the wavelengths ranging from 500 nm-520 nm and 650 nm-750 nm. In other instances, the detector is configured to measure transmitted light over wavelengths ranging from 540 nm-560 nm and 650 nm-750 nm. In yet other instances, the detector is configured to measure transmitted light over wavelengths ranging from 560 nm-590 nm and 650 nm-750 nm. In still other instances, the detector is configured to measure transmitted light over wavelengths ranging from 500 nm-520 nm, 560 nm-590 nm, and 650-750 nm.

In certain embodiments, detectors of interest are configured to collect spectra of light over a range of wavelengths. For example, systems may include one or more detectors configured to collect spectra of light over one or more of the wavelength ranges of: 400 nm-800 nm; 498 nm-510 nm; 500 nm-600 nm; 500 nm-700 nm; 500 nm-520 nm; 540 nm-550 nm; 545 nm-555 nm; 550 nm-570 nm; 550 nm-580 nm; 560 nm-590 nm; 575 nm-595 nm; 580 nm-590 nm; 600 nm-700 nm; 600 nm-630 nm; 650 nm-750 nm; 750 nm-850 nm; 810 nm-830 nm; 815 nm-825 nm and any combinations thereof. In certain instances, the detector is configured to collect spectra of light having wavelengths ranging from 400 nm-800 nm. In other instances, the detector is configured to collect spectra of light having wavelengths ranging from 500 nm-700 nm.

In yet other embodiments, detectors of interest are configured to measure light at one or more specific wavelengths. For example, systems may include one or more detectors configured to measure light at one or more of 504 nm, 506 nm, 514 nm, 532 nm, 543 nm, 548 nm, 550 nm, 561 nm, 568 nm, 579 nm, 580 nm, 585 nm, 586 nm, 675 nm, 710 nm, 808 nm, 815 nm, 830 nm and any combinations thereof. In certain instances, the detector is configured to measure light at 548 nm. In other instances, the detector is configured to measure light at 675 nm. In other instances, the detector is configured to measure light at 830 nm. In yet other instances, the detector is configured to measure light at 548 nm and 675 nm. In still other embodiments, the detector is configured to measure at 548 nm, 675 nm and 830 nm.

In embodiments, the detector may be configured to measure light continuously or in discrete intervals. In some instances, detectors of interest are configured to measure light continuously. In other instances, detectors of interest are configured to take measurements in discrete intervals, such as measuring light every 0.001 millisecond, every 0.01 millisecond, every 0.1 millisecond, every 1 millisecond, every 10 milliseconds, every 100 milliseconds and including every 1000 milliseconds, or some other interval.

Embodiments of the subject systems may also include one or more optical components as desired to provide any desired configuration. For example, systems may having each component (i.e., light source, slit projection module, sample chamber, objective lens, wavelength separator and detector) in an "in-line" configuration where light emitted from the light source travels through each component without substantial diversion form its inline pathway. Where desired, one or more mirrors, beam splitters or other types of light diversion components may be used to divert light along a different path or to separate light into separate beams for detection.

Figure 2A:
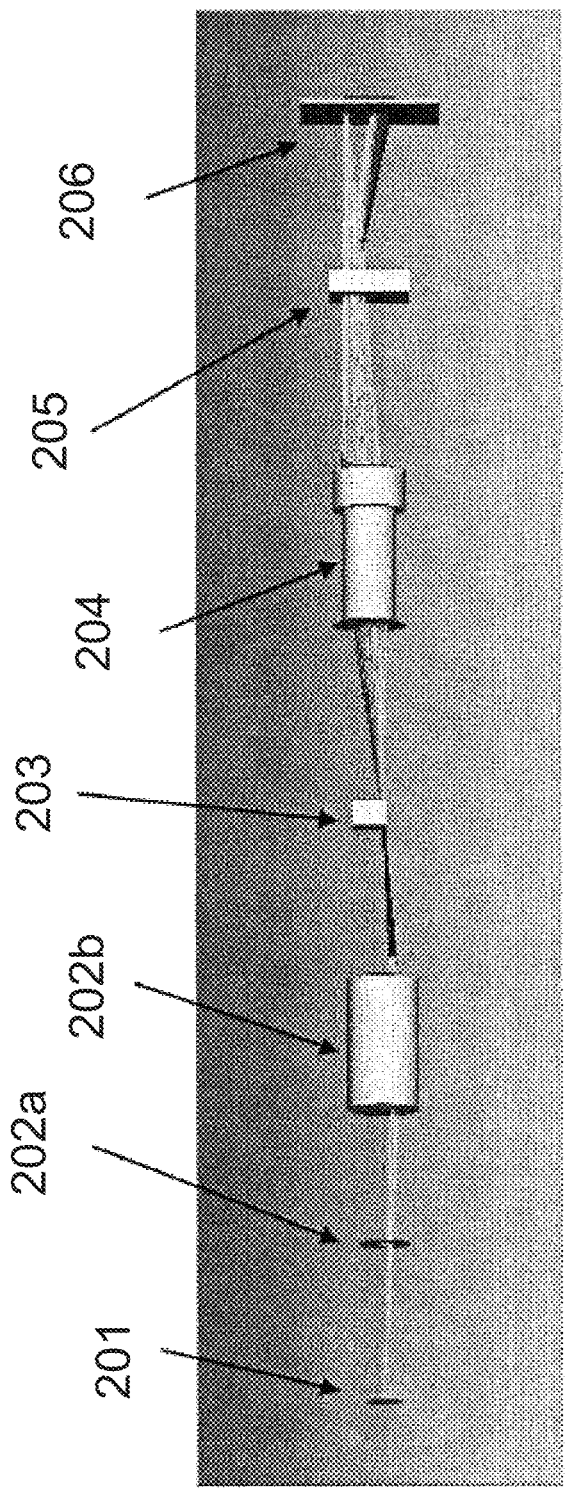
FIGS. 2a and 2b illustrates an example of configurations of absorbance systems having a slit projection module for illuminating a sample chamber with a slit-shaped beam according to certain embodiments.

FIG. 2a depicts a side configuration of the subject systems according to one embodiment. A light source (201) provides light emitting one or more wavelengths of light through a slit projection module which includes a slit (202a) for narrowing the beam of light producing a slit-shaped beam and an objective lens (202b) for focusing and de-magnifying the slit-shaped beam. The slit-shaped beam illuminates a sample chamber (203) where analyte in the sample absorbs light and a remaining portion of the light is transmitted and collected by an objective lens (204) which is configured to focus the light onto a wavelength separator (e.g., diffraction grating 205) that spatially separates the light into its component wavelengths. The spatially separated light is then detected by a detector (e.g., CCD, 206).

Figure 2B:
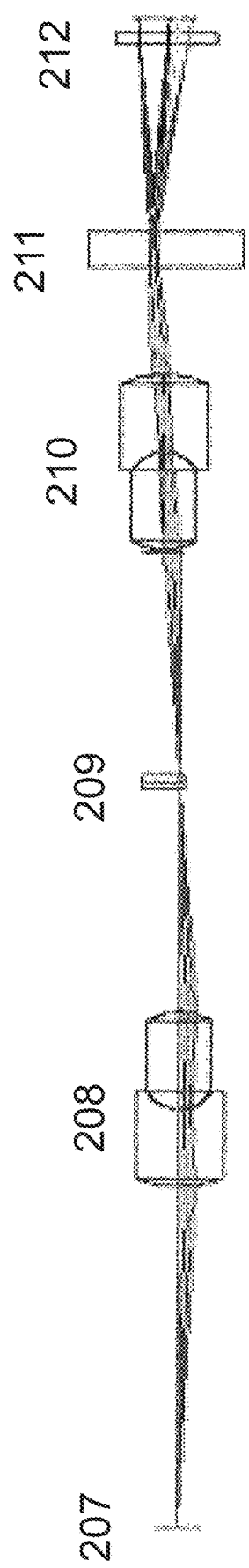

FIG. 2b depicts a top view of a configuration of the subject systems according to another embodiment. A light source (207) provides light emitting one or more wavelengths of light through a slit projection module (208) which includes a slit and an objective lens for providing a slit-shaped beam. The slit-shaped beam illuminates a sample chamber (209) where analyte in the sample absorbs light and a remaining portion of the light is transmitted and collected by an objective lens (210) and provided onto a wavelength separator (211) that spatially separates the light into its component wavelengths. The spatially separated light is then detected by a detector (212).

In some embodiments, systems are configured having one or more of the light source, slit projection module, sample chamber, objective lens, wavelength separator and detector is in an offset position. By "offset" is meant that the geometric center of the system component is positioned at a point in space not along the central optical axis that connects the light source and the detector. For example, in some embodiments, light source is in an offset position. In other embodiments, the slit projection module is in an offset position. Where the slit projection module includes a focusing lens, the focusing lens is, in certain instances, in an offset position. In yet other embodiments, the sample chamber is in an offset position. In still other embodiments, the objective lens for collecting and focusing transmitted light is in an offset position. In still other embodiments, the wavelength separator is in an offset position. In certain embodiments, the detector is in an offset position. In some instances, all of the light source, slit projection module, sample chamber, objective lens, wavelength separator and detector are in an offset position.

The offset distance may vary, as desired, ranging from 0.1 mm to 100 mm, such as from 0.2 mm to 95 mm, such as from 0.3 mm to 90 mm, such as from 0.4 mm to 85 mm, such as from 0.5 mm to 80 mm, such as from 0.6 mm to 75 mm, such as from 0.7 mm to 70 mm, such as from 0.8 mm to 65 mm, such as from 0.9 mm to 60 mm, such as from 1 mm to 55 mm, such as from 1.25 mm to 50 mm, such as from 1.5 mm to 45 mm, such as from 1.75 mm to 40 mm, such as from 2 mm to 30 mm, such as from 2.5 mm to 25 mm and including from 1 mm to 20 mm.

For example, where the wavelength separator is a diffraction grating, the diffraction grating may be in an offset position to facilitate diffraction of desired wavelengths (e.g., 548 nm, 675 nm, etc.) for a specific assay protocol. In another example, where the detector is a CCD detector, the CCD detector may be in an offset position to facilitated collection of light (e.g., transmitted or emitted) at position on the detector with calibrated pixels.

In certain embodiments, systems of interest include an integrated microfluidic sampling device having a capillary channel sample chamber with a sample application site coupled to an inlet for inputting a fluid sample. Accordingly, in these embodiments, the subject systems are not configured to receive the microfluidic cartridge device described above, but instead are configured to receive the fluid sample directly, which is subsequently removed following assay of the sample.

In embodiments, the integrated sampling device includes a capillary channel sample chamber and a sample application site coupled to an inlet for inputting the fluid sample. The capillary channel sample chamber of the integrated microfluidic sampling device may have an elongated structure, such that it has a length that is longer than its width. While the ratio of length to width may vary, in some instances the ratio of length to width ranges from 2 to 5000, such as 3 to 2500, such as from 4 to 1000, such as from 5 to 500, such as from 6 to 100, such as from 10 to 50 and including 15 to 20. In some instances, the length of the channel ranges from 10 mm to 500 mm, such as 20 mm to 250 mm and including 50 mm to 75 mm. In some instances, the channels have a micrometer sized cross-sectional dimension, e.g., a longest cross-sectional dimension (e.g., diameter in the case of the tubular channel) ranging from 0.1 mm to 20 mm, such as 1 mm to 10 mm and including 3 mm to 5 mm. In some instances the width of the channel ranges from 0.001 mm to 20 mm, such as from 0.005 mm to 19 mm, such as from 0.01 mm to 18 mm, such as from 0.05 mm to 17 mm, such as from 0.1 mm to 15 mm, such as from 0.5 mm to 12.5 mm, such as 1 to 10 and including 3 to 5 mm. In some instances the height of the channel ranges from 5 µm to 500 µm, such as 10 µm to 150 µm and including 20 µm to 70 µm. Likewise, the capillary channel may have a cross sectional shape such as rectilinear cross sectional shapes, e.g., squares, rectangles, trapezoids, triangles, hexagons, etc., curvilinear cross-sectional shapes, e.g., circles, ovals, etc., as well as irregular shapes, e.g., a parabolic bottom portion coupled to a planar top portion, etc.

The sample application site of the integrated microfluidic sampling device is a structure configured to receive a sample having a volume ranging from 5 µL to 100 µL, such as 10 µL to 50 µL and including 20 µL to 30 µL. The sample application site can have any convenient shape, so long as it provides for fluid access, either directly or through an intervening component(s) that provides for fluidic communication, to the capillary channel.

The inlet of the integrated microfluidic sampling device is in fluidic communication with sample application site and the capillary channel sample chamber and may be any suitable shape, where cross-sectional shapes of inlets of interest include, but are not limited to: rectilinear cross sectional shapes, e.g., squares, rectangles, trapezoids, triangles, hexagons, etc., curvilinear cross-sectional shapes, e.g., circles, ovals, etc., as well as irregular shapes, e.g., a parabolic bottom portion coupled to a planar top portion, etc. Depending on the shape of the inlet, the sample inlet may have an opening size which varies, ranging from 0.1 $mm^2$ to 100 $mm^2$, such as 1 $mm^2$ to 75 $mm^2$ and including 5 $mm^2$ to 50 $mm^2$.

In some instances, the integrated microfluidic sampling device includes a mixing chamber positioned in the fluidic path between the sample application site and the capillary channel sample chamber that is configured to combine sample which has been applied to the sample application and is flowing through the capillary channel with one or more reagents.

In some instances, the mixing chamber of the integrated microfluidic sampling device includes a contacting structure that provides for high surface area (e.g., porous disc) upon which one or more reagents may be positioned, where in certain instances the high surface area structure is configured to filter or facilitate contact between one or more components of the sample with reagents present in the mixing chamber. In certain instances, the high surface area structure is configured to not filter components of the sample and to simply facilitate contact between the reagents and the sample flowing therethrough. For example, where the sample is a whole blood sample, the high surface area structure may be one that is configured not to impede the flow of any of the whole blood components, e.g., white blood cells, red blood cells, platelets, etc., through the high surface area structure. In such instances, the high surface area structure may have a porosity ranging from 20 to 80, such as 30 to 70 and including 40 to 60. Suitable high surface area, porous materials for facilitating contact between sample and reagents include, but are not limited to, polymeric materials, glass materials, ceramic materials, metallic materials, etc. such as for example, polyethylene, polypropylene, polyvinylidine fluoride, and the like.

The reagents contained in the mixing chamber may, for example, include specific binding members, enzymes, substrates, oxidizers, fluorescent markers, etc., such as those described below. Likewise, the amount of reagent present in the mixing chamber or contacting structure of the integrated microfluidic sampling device may vary, e.g., depending on the particular type of assay for which the device is configured. In some instances, the amount of a reagent is sufficient to provide for a concentration of reagent in the sample following flow through the mixing chamber that ranges from 0.002 microgram/mL to 100 microgram/mL, such as 0.02 microgram/mL to 10 microgram/mL and including 0.2 to 1 microgram/mL. While the dry weight of a reagent present in the mixing chamber may vary, in some instances the dry weight ranges from 0.01 ng to 500 ng, such as 0.3 ng to 120 ng and including 3 ng to 12 ng.

As discussed above, where the subject systems include an integrated microfluidic sampling device, the sampling device is configured to receive a fluid sample which is subsequently removed following assay of the sample. By "removed" is meant that no amount of the sample remains in contact with the subject systems, including any of the capillary channel sample chamber, sample application site, inlet, as well as mixing chamber. In other words, when the sample is removed, all traces of the sample are cleared from the components of the system. In some embodiments, systems may further include one or more washing devices for cleaning the integrated microfluidic sampling device. For example, the washing devices may include microconduits with or without spray nozzles for delivering wash buffer to clean the sampling device. In certain embodiments, these systems include a reservoir for storage of one or more wash buffers.

In some instances, the subject systems may include one or more components for reading or interrogating a unique identifier (e.g., barcode, serial number) on the microfluidic cartridge, where identifiers of interest may provide information about the device, e.g., the particular assay for which it is configured, manufacturing lot number, etc., which identifiers may be unique identifiers. The identifiers may, in certain instances, provide information or characteristics about the microfluidic cartridge, including but not limited to index of refraction of the sample channel, index of refraction of the blank reference window, sample channel dimensions including sample channel height, sample channel width, sample channel length, overall sample channel depth, thickness of the sample channel walls. Likewise, the identifiers may include information about the blank reference window, such as index of refraction of the blank reference window, blank reference window dimensions including blank reference window height, blank reference window width, blank reference window length, overall blank reference window, thickness of the blank reference window walls.

Any convenient identification reader or interrogation protocol may be employed, including but not limited to a bar code reader, RFID interrogation systems, magnetic strip readers, tactile code identifiers, among other identification protocols.

In certain embodiments, the subject absorbance detection systems may be coupled to one or more fluorescence detection systems for interrogating the sample chamber for fluorescence. For example, fluorescence detection systems may include one or more light sources (e.g., broadband or narrow band light sources, such as those described above), optical module for collecting and focusing emission light, wavelength separators for spatially separating the collected light to be detected and one or more photosensors or photodetectors.

In certain embodiments, both the fluorescence detection systems and the absorbance detection systems employ one or more common components as described herein. For example, in some instances both fluorescence detection systems and absorbance detection systems employ a common objective lens module for collecting and focusing light from the sample chamber (e.g., emitted light or transmitted light). In other instances, both fluorescence detection systems and absorbance detection systems employ a common wavelength separator apparatus (e.g., diffraction grating, optical filters, filter wheel having one or more diffraction gratings and optical filters). In yet other instances, both fluorescence detection systems and absorbance detection systems employ the same detector for measuring light from the sample chamber.

Fluorescence imaging and digital processing systems which may be coupled to the subject systems, in certain instances, include systems for imaging samples in capillary channels such as those described in U.S. Pat. Nos. 8,248,597; 7,927,561 and 7,738,094 as well as those described in co-pending U.S. patent application Ser. No. 13/590,114 filed Aug. 20, 2012, the disclosures of which are herein incorporated by reference.

Figure 3:
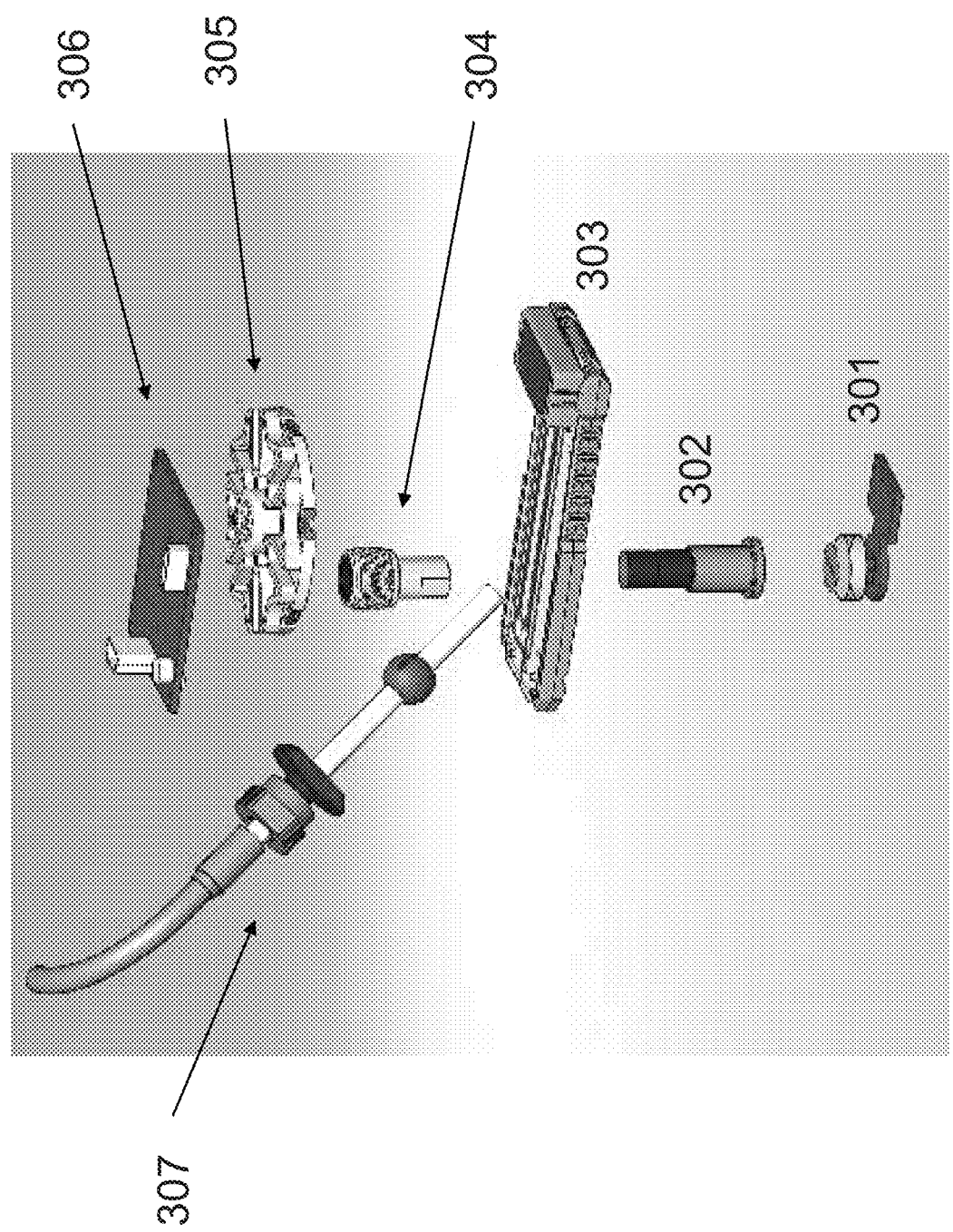
FIG. 3 illustrates an example of a configuration of absorbance systems having a slit-projection module coupled to a fluorescence detection system according to certain embodiments.

FIG. 3 depicts a configuration of the subject systems according to another embodiment where an absorbance detection system is coupled to a fluorescence detection system. As discussed above, the absorbance detection systems includes a light source (301) emitting one or more wavelengths of light through a slit projection module (302) which includes a slit for narrowing the beam of light producing a slit-shaped beam and an objective lens for focusing and de-magnifying the slit-shaped beam. The slit-shaped beam illuminates a sample chamber in a microfluidic cartridge (303) where analyte in the sample absorbs light and a remaining portion of the light is transmitted and collected by an objective lens (304) which is configured to focus the light onto a wavelength separator 305 (e.g., filter wheel having one or more optical filters and diffraction gratings) that spatially separates the light into its component wavelengths. The spatially separated light is then detected by a detector (e.g., CCD, 306). For fluorescence detection, the system includes a second light source (307) which is positioned above the sample chamber to illuminate the sample chamber and fluorescence produced by the analytes is collected with objective lens (304), spatially separated using filter wheel 305 and detected by detector 306. In this embodiment, the fluorescence detection system and the absorbance detection system employs a common objective lens (304) for collecting light from the sample chamber (303), wavelength separator apparatus (305) and detector (306).

In some embodiments, systems of interest also include one or more processors for processing assay data collected, a display, such as a liquid crystal display (LCD) for displaying raw data collected during assay or processed results received from the processor, as well as input devices, such as buttons, a keyboard, mouse or touch-screen. In addition, systems may include one or more of a wired or wireless communication protocols or an integrated printer to communicate the results to one or more users. For example, systems may include one or more computer system components, such as those as described in greater detail below.

Figure 4:
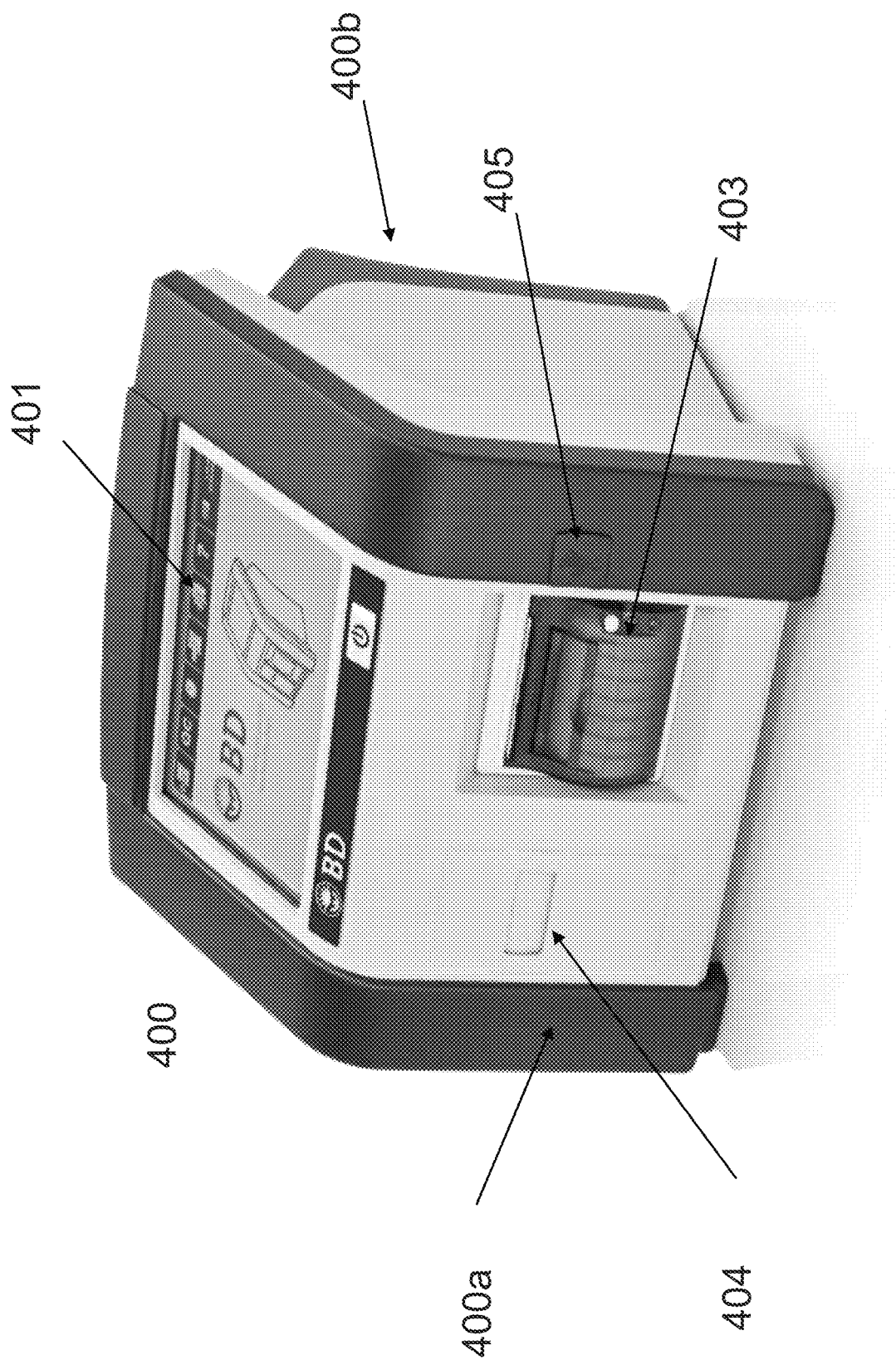
FIG. 4 depicts an example of a system of interest according to certain embodiments.

FIG. 4 depicts an example of an assay reader system of interest according one embodiment. System includes a housing (400) having a front side (400a) and a back side (400b). Front side (400a) includes a display (401), such as a liquid crystal display (LCD) for displaying raw data collected during assay or processed results received from the processor, an integrated printer (403) for communicating assay data to the user, as well as a slot for inserting (404) microfluidic cartridge device into the assay reader system. The assay reader system also includes a communication interface (405) to allow data communication (e.g., USB port) between the subject system and one or more other external devices such as a computer terminal that is configured for similar complementary data communication. Back side (400b) can include cable connections for power and data communication protocols (not shown) as well as cooling vents operably connected to cooling fans and heat sinks. Back side (400b) can also include one or more lift handles for manually moving or carrying the assay reader system. As shown in FIG. 4, the subject systems can be configured to be a unitary, "all-in-one"-type system which all of the optics, electronics (described in greater detail below), display, communication protocols in a single housing. In certain embodiments, systems of interest are configured to be capable for movement (lifted or carried a distance of 50 meters or more) by a human without machine assistance (e.g., with lift handles). As such, systems of interest, in these embodiments, are 25 kg or less, such as 20 kg or less, such as 15 kg or less and including 10 kg or less, e.g., 5 kg or less, and may include, as desired, a built in handle or other structure to provide for ease of manipulation/transportation.

Microfluidic Cartridge Devices

Aspects of the present disclosure also include a microfluidic cartridge device that is configured to be received by certain systems described herein. In embodiments, the microfluidic cartridge device includes a capillary channel sample chamber in fluid communication with a sample application site coupled to an inlet for inputting the fluid sample. The term "microfluidic" is used herein in its conventional sense to refer to a device that is configured to control and manipulate fluids geometrically constrained to a small scale (e.g., sub-millimeter). As the devices include a capillary channel sample chamber, they include an elongated structure that is configured to provide for capillary flow of liquid therethrough. In addition to the sample application site, capillary channel sample chamber and inlet, aspects of the microfluidic device includes a reagent mixing chamber in communication with the sample application site and inlet for contacting and mixing the fluidic sample with one or more reagents. In certain embodiments, the mixing chamber is configured as a porous disc containing reagents for contacting with the sample.

In embodiments of the present disclosure, the capillary channel sample chamber is an elongated structure, such that it has a length that is longer than its width. While the ratio of length to width may vary, in some instances the ratio of length to width ranges from 2 to 5000, such as 3 to 2500, such as from 4 to 1000, such as from 5 to 500, such as from 6 to 100, such as from 10 to 50 and including 15 to 20. In some instances, the length of the channel ranges from 10 mm to 500 mm, such as 20 mm to 250 mm and including 50 mm to 75 mm. In some instances, the channels have a micrometer sized cross-sectional dimension, e.g., a longest cross-sectional dimension (e.g., diameter in the case of the tubular channel) ranging from 0.1 mm to 20 mm, such as 1 mm to 10 mm and including 3 mm to 5 mm. In some instances the width of the channel ranges from 0.001 mm to 20 mm, such as from 0.005 mm to 19 mm, such as from 0.01 mm to 18 mm, such as from 0.05 mm to 17 mm, such as from 0.1 mm to 15 mm, such as from 0.5 mm to 12.5 mm, such as 1 to 10 and including 3 to 5 mm. In some instances the height of the channel ranges from 5 μm to 500 μm, such as 10 μm to 150 μm and including 20 μm to 70 μm.

The cross sectional shape of the capillary channels may vary, in some instances, cross-sectional shapes of channels of interest include, but are not limited to: rectilinear cross sectional shapes, e.g., squares, rectangles, trapezoids, triangles, hexagons, etc., curvilinear cross-sectional shapes, e.g., circles, ovals, etc., as well as irregular shapes, e.g., a parabolic bottom portion coupled to a planar top portion, etc.

Positioned at one end of capillary channel (i.e., the proximal end) is a sample application site having a fluidic inlet for conveying the sample into the capillary channel sample chamber. The sample application site is a site or location configured to receive a volume of sample, e.g., a biological sample, to be analyzed. In some instances, the sample application site is a structure configured to receive a sample having a volume ranging from 5 µL to 100 µL, such as 10 µL to 50 µL and including 20 µL to 30 µL. The sample application site can have any convenient shape, so long as it provides for fluid access, either directly or through an intervening component(s) that provides for fluidic communication, to the capillary channel.

The sample application site is in communication with an inlet to one end of the capillary channel sample chamber. The sample application site may be positioned along a side of the microfluidic device such that sample applied to the sample application site is drawn into the inlet of the capillary channel sample chamber. The inlet for conveying the sample into the capillary channel sample chamber may be any suitable shape, where cross-sectional shapes of channels of interest include, but are not limited to: rectilinear cross sectional shapes, e.g., squares, rectangles, trapezoids, triangles, hexagons, etc., curvilinear cross-sectional shapes, e.g., circles, ovals, etc., as well as irregular shapes, e.g., a parabolic bottom portion coupled to a planar top portion, etc. Depending on the shape of the inlet as well as the dimensions of the microfluidic cartridge, the sample inlet may have an opening size which varies, ranging from $0.1$ $mm^2$ to $100$ $mm^2$, such as $1$ $mm^2$ to $75$ $mm^2$ and including $5$ $mm^2$ to $50$ $mm^2$.

In some embodiments, the fluid sample is preloaded onto the sample application site and the preloaded microfluidic device is stored for a predetermined period of time before the sample is assayed. As such, systems of the present disclosure may also include one or more preloaded microfluidic cartridges. For example, the fluid sample may be preloaded onto the sample application site before assaying the sample for 0.001 hours or more, such as 0.005 hours or more, such as 0.01 hours or more, such as 0.05 hours or more, such as 0.1 hours or more, such as 0.5 hours or more, such as 1 hour or more, such as 2 hours or more, such as 4 hours or more, such as 8 hours or more, such as 16 hours or more, such as 24 hours or more, such as 48 hours or more, such as 72 hours or more, such as 96 hours or more, such as 120 hours or more, such as 144 hours or more, such as 168 hours or more and storing the preloaded microfluidic device for 240 hours or more before assaying the sample or the amount of storage time may range such as from 0.1 hours to 240 hours, such as from 0.5 hours to 216 hours, such as from 1 hour to 192 hours and including from 5 hours to 168 hours before assaying the sample.

In some embodiments, the microfluidic device includes a mixing chamber positioned in the fluidic path between the sample application site and the capillary channel sample chamber. By mixing chamber is meant an area or location in the fluidic path that is configured to combine sample which has been applied to the sample application and is flowing to the capillary channel with one or more reagents.

In some instances, the mixing chamber includes a contacting structure that provides for high surface area (e.g., porous disc) upon which one or more reagents may be positioned, where in certain instances the high surface area structure is configured to filter or facilitate contact between one or more components of the sample with reagents present in the mixing chamber. In certain instances, the high surface area structure is configured to not filter components of the sample and to simply facilitate contact between the reagents and the sample flowing therethrough. For example, where the sample is a whole blood sample, the high surface area structure may be one that is configured not to impede the flow of any of the whole blood components, e.g., white blood cells, red blood cells, platelets, etc., through the high surface area structure. In such instances, the high surface area structure may have a porosity ranging from 20 to 80, such as 30 to 70 and including 40 to 60. Suitable high surface area, porous materials for facilitating contact between sample and reagents include, but are not limited to, polymeric materials, glass materials, ceramic materials, metallic materials, etc. such as for example, polyethylene, polypropylene, polyvinylidine fluoride, and the like.

Present in the mixing chamber is one or more reagents, which reagents may be present on a surface of a high surface area structure when present. A variety of different reagents may be present in the mixing chamber or domain of the device, depending on the particular assay for which the device is configured. Reagents of interest include labeled specific binding members, enzymes, substrates, oxidizers, etc., among others. In certain embodiments, the one or more reagents in the mixing chamber include a labeled specific binding member. For example, the labeled specific binding member may include a specific binding domain and a label domain. The terms "specific binding," "specifically binds," and the like, refer to the preferential binding of a domain (e.g., one binding pair member to the other binding pair member of the same binding pair) relative to other molecules or moieties in a solution or reaction mixture. The specific binding domain may bind (e.g., covalently or non-covalently) to a specific epitope of an analyte of interest. In certain aspects, specific binding domain non-covalently binds to a target. In such instances, the specific binding domain association with the binding target (e.g., cell surface marker) may be characterized by a KD (dissociation constant) of $10-5$ M or less, $10-6$ M or less, such as $10-7$ M or less, including $10-8$ M or less, e.g., $10-9$ M or less, $10-10$ M or less, $10-11$ M or less, $10-12$ M or less, $10-13$ M or less, $10-14$ M or less, $10-15$ M or less, including $10-16$ M or less.

A variety of different types of specific binding domains may be employed as the capture ligands. Specific binding domains of interest include, but are not limited to, antibody binding agents, proteins, peptides, haptens, nucleic acids, etc. The term "antibody binding agent" as used herein includes polyclonal or monoclonal antibodies or fragments that are sufficient to bind to an analyte of interest. The antibody fragments can be, for example, monomeric Fab fragments, monomeric Fab' fragments, or dimeric F(ab)'2 fragments. Also within the scope of the term "antibody binding agent" are molecules produced by antibody engineering, such as single-chain antibody molecules (scFv) or humanized or chimeric antibodies produced from monoclonal antibodies by replacement of the constant regions of the heavy and light chains to produce chimeric antibodies or replacement of both the constant regions and the framework portions of the variable regions to produce humanized antibodies. In certain embodiments, reagents of interest include, CD4-PECy5, CD3-APC, CD45RA-APC, CD14-PE.

The label domain may be detectable based on, for example, fluorescence emission maxima, fluorescence polarization, fluorescence lifetime, light scatter, mass, molecular mass, or combinations thereof. In certain aspects, the label domain may be a fluorophore (i.e., a fluorescent label, fluorescent dye, etc.). Fluorophores can be selected from any of the many dyes suitable for use in analytical applications (e.g., flow cytometry, imaging, etc.). A large number of dyes are commercially available from a variety of sources, such as, for example, Molecular Probes (Eugene, Oreg.) and Exciton (Dayton, Ohio). Examples of fluorophores that may be incorporated into the microparticles include, but are not limited to, 4-acetamido-4'-isothiocyanatostilbene-2,2'disulfonic acid; acridine and derivatives such as acridine, acridine orange, acrindine yellow, acridine red, and acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide; anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanine and derivatives such as cyanosine, Cy3, Cy5, Cy5.5, and Cy7; 4',6-diaminidino-2-phenylindole (DAPI); 5',5''-dibromopyrogallol-sulfonephthalein (Bromopyrogallol Red); 7-diethylamino-3-(4'-isothiocyanatophenyl)-4-methylcoumarin; diethylaminocoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl) aminofluorescein (DTAF), 2'7'-dimethoxy-4'5'-dichloro-6-carboxyfluorescein (JOE), fluorescein isothiocyanate (FITC), fluorescein chlorotriazinyl, naphthofluorescein, and QFITC (XRITC); fluorescamine; IR144; IR1446; Green Fluorescent Protein (GFP); Reef Coral Fluorescent Protein (RCFP); Lissamine™; Lissamine rhodamine, Lucifer yellow; Malachite Green isothiocyanate; 4-methylumbelliferone; ortho cresolphthalein; nitrotyrosine; pararosaniline; Nile Red; Oregon Green; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), 4,7-dichlororhodamine lissamine, rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, and tetramethyl rhodamine isothiocyanate (TRITC); riboflavin; rosolic acid and terbium chelate derivatives; xanthene; or combinations thereof. Other fluorophores or combinations thereof known to those skilled in the art may also be used, for example those available from Molecular Probes (Eugene, Oreg.) and Exciton (Dayton, Ohio). The fluorescent label may be distinguishable based on fluorescence emission maxima, and optionally further based on light scatter or extinction.

The amount of reagent present in the mixing chamber or contacting structure may vary, e.g., depending on the particular type of assay for which the device is configured. In some instances, the amount of a reagent is sufficient to provide for a concentration of reagent in the sample following flow through the mixing chamber that ranges from 0.002 microgram/mL to 100 microgram/mL, such as 0.02 microgram/mL to 10 microgram/mL and including 0.2 to 1 microgram/mL. While the dry weight of a reagent present in the mixing chamber may vary, in some instances the dry weight ranges from 0.01 ng to 500 ng, such as 0.3 ng to 120 ng and including 3 ng to 12 ng.

In some instances, the device may include an analyte specific capture domain. An analyte specific capture domain is a domain or region of the capillary channel from which a result may be read during use of the device. The analyte specific capture domain is positioned at some distance downstream from the sample application site of the device. By "downstream" is meant the direction that the sample flows by capillary action, i.e., the direction of fluid flow from the sample application site. The total distance fluid flows between the sample receiving region and the detection region may vary, ranging in some instances from 2 cm to 500 cm, such as 10 cm to 100 cm and including 20 cm to 50 cm.

The analyte specific capture domain is a region that includes an amount of a capture probe, also referred to herein as a "detection capture probe." A detection capture probe is immobilized in the analyte specific capture domain and specifically binds to target molecule of interest, e.g., an analyte, a control molecule, etc. The size of the detection capture probe region may vary, and in some instances the capture probe region can have an area ranging from 0.01 $cm^2$ to 0.5 $cm^2$, such as 0.05 $cm^2$ to 0.1 $cm^2$ and including 0.1 $cm^2$ to 0.2 $cm^2$. An analyte specific capture domain can have a variety of different configurations, where the configuration can be random or the configuration can have a specific shape such as a line, circle, square, or more complex shape, such as a cross-shape, as desired. A given analyte specific capture domain can include a single capture probe or two or more different capture probes, where each of the two or more different capture probes, where when the detection region includes two or more capture probes, the capture probes can be distinct from each other (i.e., bind to different target molecules), as desired.

In some embodiments an analyte specific capture domain may be provided that includes particles displaying a specific binding member(s) for a target molecule(s), e.g., an analyte(s) of interest, a control or reference molecule, etc. For example, in some embodiments the device may include an analyte specific capture domain comprised of capture beads immobilized on a convenient surface, e.g., the upper surface, of a domain of the capillary channel, e.g., a capillary chamber in the capillary channel, e.g., as described in PCT Application Serial No. PCT/US2012/065683 filed on Nov. 16, 2012 and hereby incorporated by reference. The capture beads may be coated with a binding reagent that specifically binds to the analyte of interest. In some embodiments, the capture beads are coated with an antigen to which the antibody of interest specifically binds. In such instances, a fluorescently labeled reagent for detection may be added that specifically binds to the analyte, enabling the detection of the captured analyte by its fluorescence emissions. The capture beads may be immobilized to a spot on the upper surface of the capillary chamber through any suitable means. In some instances, beads stayed localized in the spot by passive interactions between the beads and the capillary chamber surface, but covalent binding can be used, as desired.

Capture beads coated with different antigens can be localized in different spots within the capillary chamber to enable the multiplexed detection of multiple analytes. Alternatively, capture beads coated with different antigens can be distinguishably labeled using fluorescent dyes that are distinguishable from each other and from the dye-labeled detection reagents that are used to measure the captured analytes. In this manner, the beads can be immobilized in the same spot, but distinguished by their fluorescent emissions. In other embodiments, labeling reagents may be disposed at an analyte specific capture domain disposed at the sample application site and labeled sample may flow to a reaction chamber in the capillary channel for detection.

In some instances, the microfluidic cartridge may include a quality control domain in the capillary channel, e.g., positioned near the end of the channel furthest from the sample application site. The quality control channel may vary, and may for example include a capture member, e.g., antibody, specific for a labeled reagent, etc., such as described in greater detail below, e.g., to provide a confirmation that sample flows through the device during a given assay.

In some instances, the microfluidic cartridge may include one or more identifiers, which identifiers may provide information about the device, e.g., the particular assay for which it is configured, manufacturing lot number, etc., which identifiers may be unique identifiers. The identifiers may be human and/or machine readable, e.g., may be text (e.g., serial numbers) or a bar code, as desired. The identifiers may, in certain instances, provide information or characteristics about the microfluidic cartridge, including but not limited to index of refraction of the sample channel, index of refraction of the blank reference window, sample channel dimensions including sample channel height, sample channel width, sample channel length, overall sample channel depth, thickness of the sample channel walls. Likewise, the identifiers may include information about the blank reference window, such as index of refraction of the blank reference window, blank reference window dimensions including blank reference window height, blank reference window width, blank reference window length, overall blank reference window, thickness of the blank reference window walls.

In some embodiments, the microfluidic cartridge further includes a blank reference window which is also interrogated by the slit projection module to provide a blank absorbance for use in calculating analyte concentration. The absorbance by the blank reference window is in certain embodiments, configured to be identical to absorbance by the sample chamber such that transmission through the blank reference window can be used to correct for absorption, scatter, etc. by the microfluidic cartridge when practicing the methods described herein. In certain embodiments, the blank reference window has an absorbance and transmission at the one or more wavelengths of incident light which is substantially the same as the capillary channel sample chamber. In other embodiments, the blank reference window scatters light at the one or more wavelengths which is substantially the same as the capillary channel sample chamber. In yet other embodiments, the blank reference window has an absorbance, transmission and scatters light at the one or more incident wavelengths which is substantially the same as the capillary channel sample chamber. In still other embodiments, the blank reference window has the same index of refraction as the capillary channel sample chamber.

The blank reference window may be any convenient size and shape. For example, the blank reference window may be in the form of a square, circle, oval, rectangle, pentagon, hexagon, octagon or any other suitable polygon. In some embodiments, the blank reference window has a ratio of length to width which ranges from 1 to 50, such as 3 to 25, such as from 4 to 10, such as from 5 to 8, including 15 to 20. In certain embodiments, the blank reference window is a square and has a ratio of length to width of 1. The length of the blank reference window may vary, ranging from 1 mm to 50 mm, such as 2 mm to 25 mm and including 5 mm to 20 mm. The width of the blank reference window may vary, ranging from 0.001 mm to 20 mm, such as from 0.005 mm to 19 mm, such as from 0.01 mm to 18 mm, such as from 0.05 mm to 17 mm, such as from 0.1 mm to 15 mm, such as from 0.5 mm to 12.5 mm, such as 1 to 10 and including 3 to 5 mm. In some instances the height of the channel ranges from 5 µm to 500 µm, such as 10 µm to 150 µm and including 20 µm to 70 µm. In certain embodiments, the blank reference window has a width which is substantially the same as the width of the capillary channel sample chamber.

The blank reference window may be positioned at any convenient location on the microfluidic cartridge. In certain embodiments, the blank reference window is positioned along the same axis as the capillary channel sample chamber. For example, the blank reference window may be positioned along the same axis as the capillary channel sample chamber at a position that is 1 mm away or more from the capillary channel sample chamber, such as 2 mm or more, such as 3 mm or more, such as 4 mm or more, such as 5 mm or more and including 10 mm or more away from the capillary channel sample chamber.

Figure 5:
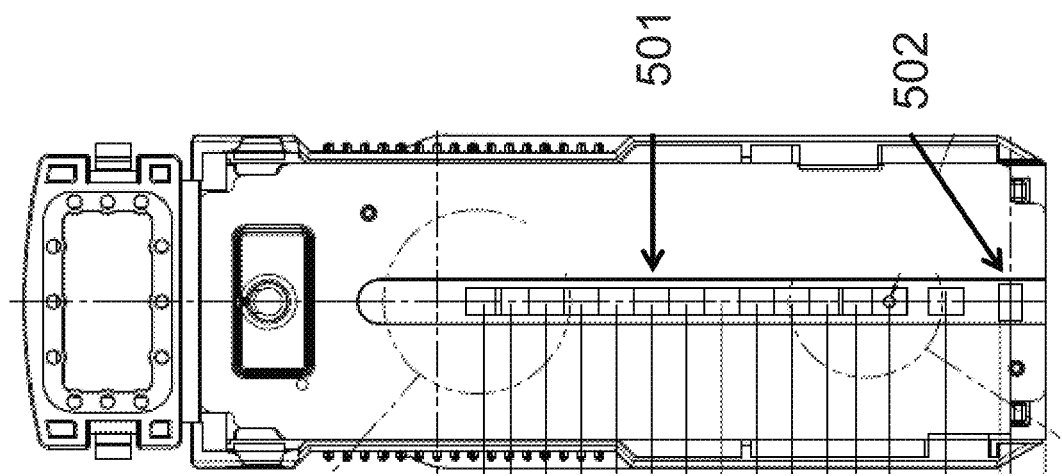
FIG. 5 illustrates an example a microfluidic cartridge having a microfluidic sample chamber and a reference slit window for providing blank transmittance according to certain embodiments.

FIG. 5 illustrates one example of a microfluidic cartridge having a microfluidic sample chamber for absorbance measurement (501) and a reference window to provide for a blank during absorbance measurement (502).

One example of a suitable microfluidic cartridge which may be received into the systems described herein may include, but are not limited to those described in copending U.S. patent application Ser. No. 14/152,954 filed on Jan. 10, 2014, the disclosure of which is herein incorporated by reference.

Computer-Controlled Systems

Aspects of the present disclosure further include computer controlled systems for practicing the subject methods, where the systems further include one or more computers for automation or semi-automation of a system for practicing methods described herein. In certain embodiments, systems include a computer having a computer readable storage medium with a computer program stored thereon, where the computer program when loaded on the computer includes algorithm illuminating a sample in a sample chamber with a light source; algorithm for moving a slit projection module along a length of the sample chamber; algorithm for detecting light transmitted through the sample chamber, algorithm for calculating absorbance of light at one or more wavelengths using the detected transmitted light and algorithm for calculating concentration of an analyte based on the absorbance determined from the transmitted light.

In some embodiments, systems include a computer program that includes algorithm for calculating absorbance of light at one or more wavelengths based on transmitted light detected by the detector. Absorbance of light by the target analyte is determined by inputting transmittance data from the detector into a processor which applies the Beer-Lambert Law to calculate absorbance at a given wavelength:

$$\text{Absorbance }(\lambda) = -\text{Log}_{10}(I/I_0)$$

where I is the intensity of the light transmitted through the sample chamber and $I_0$ is the intensity of incident light used to interrogate the sample.

Systems also include a computer program that includes algorithm for calculating concentration of the analyte based on calculated absorbance at one or more wavelengths. The concentration of analyte, in certain embodiments, is calculated by inputting absorbance values calculated based on transmittance data into a processor which applies the formula:

$$\text{Absorbance } (\lambda) = [\text{molar absorptivity} \lambda] \times [\text{concentration}] \times [\text{pathlength}].$$

In some embodiments, systems include algorithm for calculating absorbance of the analyte while accounting for scatter by the sample. The absorbance by the analyte while accounting for scatter by the sample is determined, in certain instances, by inputting absorbance values calculated based on transmittance data into a processor which applies the formula:

$$\text{Concentration}_{analyte} = A^*(\text{Abs}_{\lambda 1}) + B^*(\text{Abs}_{\lambda 2}) + C,$$

where A, B, and C are coefficients which depend on the wavelengths interrogated and analytes being measured. In embodiments, the value of A may vary, in certain instances, ranging from 20 g/dL to 60 g/dL, such as from 25 g/dL to 57.5 g/dL, such as from 30 g/dL to 55 g/dL, such as from 35 g/dL to 50 g/dL and including from 37.5 g/dL to 45 g/dL. The value of B may also vary, in certain instances, ranging from 0.01 g/dL to 5 g/dL, such as from 0.05 g/dL to 4.5 g/dL, such as from 0.1 g/dL to 4 g/dL, such as from 0.25 g/dL to 3.5 g/dL, such as from 0.5 g/dL to 3 g/dL and including from 0.5 g/dL to 2 g/dL. Likewise, the value of C may also vary, ranging from 0.01 g/dL to 2 g/dL, such as from 0.025 g/dL to 1.75 g/dL, such as from 0.05 g/dL to 1.5 g/dL, such as from 0.1 g/dL to 1.25 g/dL and including from 0.25 g/dL to 2 g/dL.

For example, in certain instances systems are configured to calculate the concentration of hemoglobin in whole blood while accounting for scatter. In these instances, systems include algorithm for calculating absorbance of hemoglobin in whole blood while accounting for scatter by the whole blood sample. The system includes a computer program with algorithm for choosing a first wavelength and second wavelength to interrogate the sample. In these embodiments, the computer algorithm includes choosing a first wavelength where hemoglobin has a high molar absorptivity, which may be an isosbestic point for hemoglobin with one or more of oxyhemoglobin, carboxyhemoglobin, methemoglobin, sulfo-hemoglobin, azide-methemoglobin and cyano-methemoglobin, such as a isosbestic point for hemoglobin and oxyhemoglobin or a triple isosbestic point for hemoglobin, oxyhemoglobin and carboxyhemoglobin. For example, thea first wavelength is, in certain instances, 506 nm, 548 nm, 569 nm, 579 nm, 585 nm or 586 nm. The computer algorithm also includes choosing a second wavelength to account for scatter. In some instances, the computer algorithm includes choosing a second wavelength is an isosbestic point for hemoglobin with one or more of oxyhemoglobin, carboxyhemoglobin, methemoglobin, sulfohemoglobin, azide-methemoglobin and cyano-methemoglobin, such as a isosbestic point for hemoglobin and oxyhemoglobin or a triple isosbestic point for hemoglobin, oxyhemoglobin and carboxyhemoglobin. For example, a second wavelength is, in certain instances, 650 nm, 675 nm, 710 nm, 785 nm, 808 nm, 815 nm or 830 nm.

For example, in certain embodiments systems include a computer program that includes algorithm for choosing a first wavelength of 548 nm and a second wavelength of 675 nm and determining the concentration of hemoglobin in whole blood while accounting for scatter in the whole blood sample by: 1) inputting transmittance data in to a processor applying the Beer Lambert Law; and 2) inputting the calculated absorbance values into a processor which applies the formula:

$$\text{Concentration}_{Hb} = A^*(\text{Abs}_{548\ nm}) + B^*(\text{Abs}_{675\ nm}) + C,$$

where the value of A for a whole blood sample ranges from 20 g/dL to 60 g/dL, such as from 25 g/dL to 57.5 g/dL, such as from 30 g/dL to 55 g/dL, such as from 35 g/dL to 50 g/dL and including from 37.5 g/dL to 45 g/dL; the value of B for a whole blood sample ranges from 0.01 g/dL to 5 g/dL, such as from 0.05 g/dL to 4.5 g/dL, such as from 0.1 g/dL to 4 g/dL, such as from 0.25 g/dL to 3.5 g/dL, such as from 0.5 g/dL to 3 g/dL and including from 0.5 g/dL to 2 g/dL and where the value of C of a whole blood sample ranges from 0.01 g/dL to 2 g/dL, such as from 0.025 g/dL to 1.75 g/dL, such as from 0.05 g/dL to 1.5 g/dL, such as from 0.1 g/dL to 1.25 g/dL and including from 0.25 g/dL to 2 g/dL.

In embodiments, the system includes an input module, a processing module and an output module. In some embodiments, the subject systems may include an input module such that parameters or information about each fluidic sample, intensity and wavelengths (discrete or ranges) of the applied light source, amplitude of movement by the slit projection module, number of scans and movement by the slit projection module, duration of illumination by the light source, number of different light sources, distance from light source to sample chamber, focal length of objective lens, parameters of the focusing module, path length of sample chamber, refractive index of sample, refractive index of sample chamber, number of wavelength separators, properties of wavelength separators including bandpass width, opacity, grating spacting and resolution as well as properties and sensitivity of photodetectors.

The processing module includes memory having a plurality of instructions for performing the steps of the subject methods, such as illuminating a sample in a sample chamber with a light source; moving a slit projection module along a length of the sample chamber; detecting light transmitted through the sample chamber and calculating absorbance of light at one or more predetermined wavelengths using the detected transmitted light.

After the processing module has performed one or more of the steps of the subject methods, an output module communicates the results (e.g., absorbance of the analyte at one or more wavelengths) to the user, such as by displaying on a monitor or by printing a report.

The subject systems may include both hardware and software components, where the hardware components may take the form of one or more platforms, e.g., in the form of servers, such that the functional elements, i.e., those elements of the system that carry out specific tasks (such as managing input and output of information, processing information, etc.) of the system may be carried out by the execution of software applications on and across the one or more computer platforms represented of the system.

Systems may include a display and operator input device. Operator input devices may, for example, be a keyboard, mouse, or the like. The processing module includes a processor which has access to a memory having instructions stored thereon for performing the steps of the subject methods, such as illuminating a sample in a sample chamber with a light source; moving a slit projection module along a length of the sample chamber; detecting light transmitted through the sample chamber and calculating absorbance of light at one or more predetermined wavelengths using the detected transmitted light.

The processing module may include an operating system, a graphical user interface (GUI) controller, a system memory, memory storage devices, and input-output controllers, cache memory, a data backup unit, and many other devices. The processor may be a commercially available processor or it may be one of other processors that are or will become available. The processor executes the operating system and the operating system interfaces with firmware and hardware in a well-known manner, and facilitates the processor in coordinating and executing the functions of various computer programs that may be written in a variety of programming languages, such as Java, Perl, C++, other high level or low level languages, as well as combinations thereof, as is known in the art. The operating system, typically in cooperation with the processor, coordinates and executes functions of the other components of the computer. The operating system also provides scheduling, input-output control, file and data management, memory management, and communication control and related services, all in accordance with known techniques.

The system memory may be any of a variety of known or future memory storage devices. Examples include any commonly available random access memory (RAM), magnetic medium such as a resident hard disk or tape, an optical medium such as a read and write compact disc, flash memory devices, or other memory storage device. The memory storage device may be any of a variety of known or future devices, including a compact disk drive, a tape drive, a removable hard disk drive, or a diskette drive. Such types of memory storage devices typically read from, and/or write to, a program storage medium (not shown) such as, respectively, a compact disk, magnetic tape, removable hard disk, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with the memory storage device.

In some embodiments, a computer program product is described comprising a computer usable medium having control logic (computer software program, including program code) stored therein. The control logic, when executed by the processor the computer, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

Memory may be any suitable device in which the processor can store and retrieve data, such as magnetic, optical, or solid state storage devices (including magnetic or optical disks or tape or RAM, or any other suitable device, either fixed or portable). The processor may include a general purpose digital microprocessor suitably programmed from a computer readable medium carrying necessary program code. Programming can be provided remotely to processor through a communication channel, or previously saved in a computer program product such as memory or some other portable or fixed computer readable storage medium using any of those devices in connection with memory. For example, a magnetic or optical disk may carry the programming, and can be read by a disk writer/reader. Systems of the invention also include programming, e.g., in the form of computer program products, algorithms for use in practicing the methods as described above. Programming according to the present invention can be recorded on computer readable media, e.g., any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; portable flash drive; and hybrids of these categories such as magnetic/optical storage media.

The processor may also have access to a communication channel to communicate with a user at a remote location. By remote location is meant the user is not directly in contact with the system and relays input information to an input manager from an external device, such as a a computer connected to a Wide Area Network ("WAN"), telephone network, satellite network, or any other suitable communication channel, including a mobile telephone (i.e., smartphone).

In some embodiments, systems according to the present disclosure may be configured to include a communication interface. In some embodiments, the communication interface includes a receiver and/or transmitter for communicating with a network and/or another device. The communication interface can be configured for wired or wireless communication, including, but not limited to, radio frequency (RF) communication (e.g., Radio-Frequency Identification (RFID), Zigbee communication protocols, WiFi, infrared, wireless Universal Serial Bus (USB), Ultra Wide Band (UWB), Bluetooth® communication protocols, and cellular communication, such as code division multiple access (CDMA) or Global System for Mobile communications (GSM).

In one embodiment, the communication interface is configured to include one or more communication ports, e.g., physical ports or interfaces such as a USB port, an RS-232 port, or any other suitable electrical connection port to allow data communication between the subject systems and other external devices such as a computer terminal (for example, at a physician's office or in hospital environment) that is configured for similar complementary data communication.

In one embodiment, the communication interface is configured for infrared communication, Bluetooth® communication, or any other suitable wireless communication protocol to enable the subject systems to communicate with other devices such as computer terminals and/or networks, communication enabled mobile telephones, personal digital assistants, or any other communication devices which the user may use in conjunction therewith, in managing the treatment of a health condition, such as HIV, AIDS or anemia.

In one embodiment, the communication interface is configured to provide a connection for data transfer utilizing Internet Protocol (IP) through a cell phone network, Short Message Service (SMS), wireless connection to a personal computer (PC) on a Local Area Network (LAN) which is connected to the internet, or WiFi connection to the internet at a WiFi hotspot.

In one embodiment, the subject systems are configured to wirelessly communicate with a server device via the communication interface, e.g., using a common standard such as 802.11 or Bluetooth® RF protocol, or an IrDA infrared protocol. The server device may be another portable device, such as a smart phone, Personal Digital Assistant (PDA) or notebook computer; or a larger device such as a desktop computer, appliance, etc. In some embodiments, the server device has a display, such as a liquid crystal display (LCD), as well as an input device, such as buttons, a keyboard, mouse or touch-screen.

In some embodiments, the communication interface is configured to automatically or semi-automatically communicate data stored in the subject systems, e.g., in an optional data storage unit, with a network or server device using one or more of the communication protocols and/or mechanisms described above.

Output controllers may include controllers for any of a variety of known display devices for presenting information to a user, whether a human or a machine, whether local or remote. If one of the display devices provides visual information, this information typically may be logically and/or physically organized as an array of picture elements. A graphical user interface (GUI) controller may include any of a variety of known or future software programs for providing graphical input and output interfaces between the system and a user, and for processing user inputs. The functional elements of the computer may communicate with each other via system bus. Some of these communications may be accomplished in alternative embodiments using network or other types of remote communications. The output manager may also provide information generated by the processing module to a user at a remote location, e.g., over the Internet, phone or satellite network, in accordance with known techniques. The presentation of data by the output manager may be implemented in accordance with a variety of known techniques. As some examples, data may include SQL, HTML or XML documents, email or other files, or data in other forms. The data may include Internet URL addresses so that a user may retrieve additional SQL, HTML, XML, or other documents or data from remote sources. The one or more platforms present in the subject systems may be any type of known computer platform or a type to be developed in the future, although they typically will be of a class of computer commonly referred to as servers. However, they may also be a main-frame computer, a work station, or other computer type. They may be connected via any known or future type of cabling or other communication system including wireless systems, either networked or otherwise. They may be co-located or they may be physically separated. Various operating systems may be employed on any of the computer platforms, possibly depending on the type and/or make of computer platform chosen. Appropriate operating systems include Windows NT®, Windows XP, Windows 7, Windows 8, iOS, Sun Solaris, Linux, OS/400, Compaq Tru64 Unix, SGI IRIX, Siemens Reliant Unix, and others.

Kits

Aspects of the invention further include kits, where kits include one or more microfluidic assay cartridges. In some instances, the kits can include one or more assay components (e.g., labeled reagents, buffers, etc., such as described above). In some instances, the kits may further include a sample collection device, e.g., a lance or needle configured to prick skin to obtain a whole blood sample, a pipette, etc., as desired.

Figure 6:
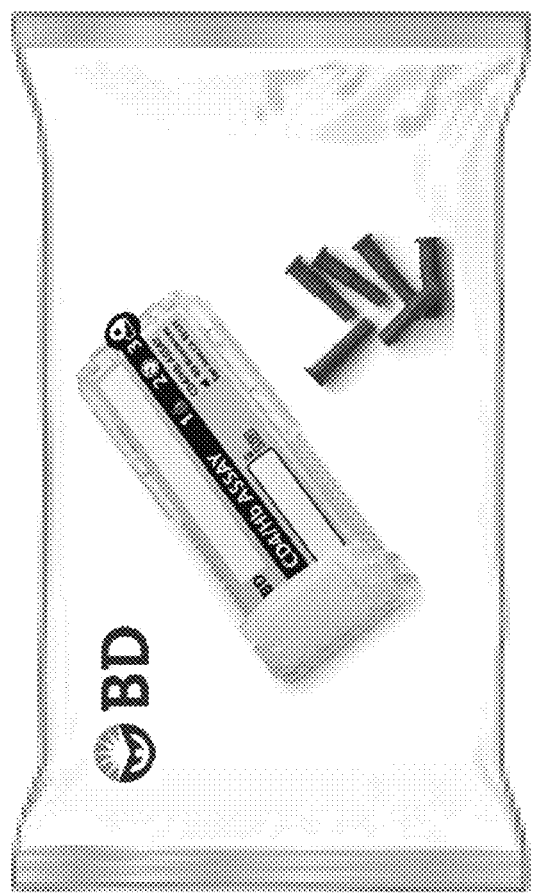
FIG. 6 shows an example of a kit having a microfluidic cartridge according to certain embodiments.
Figure 7:
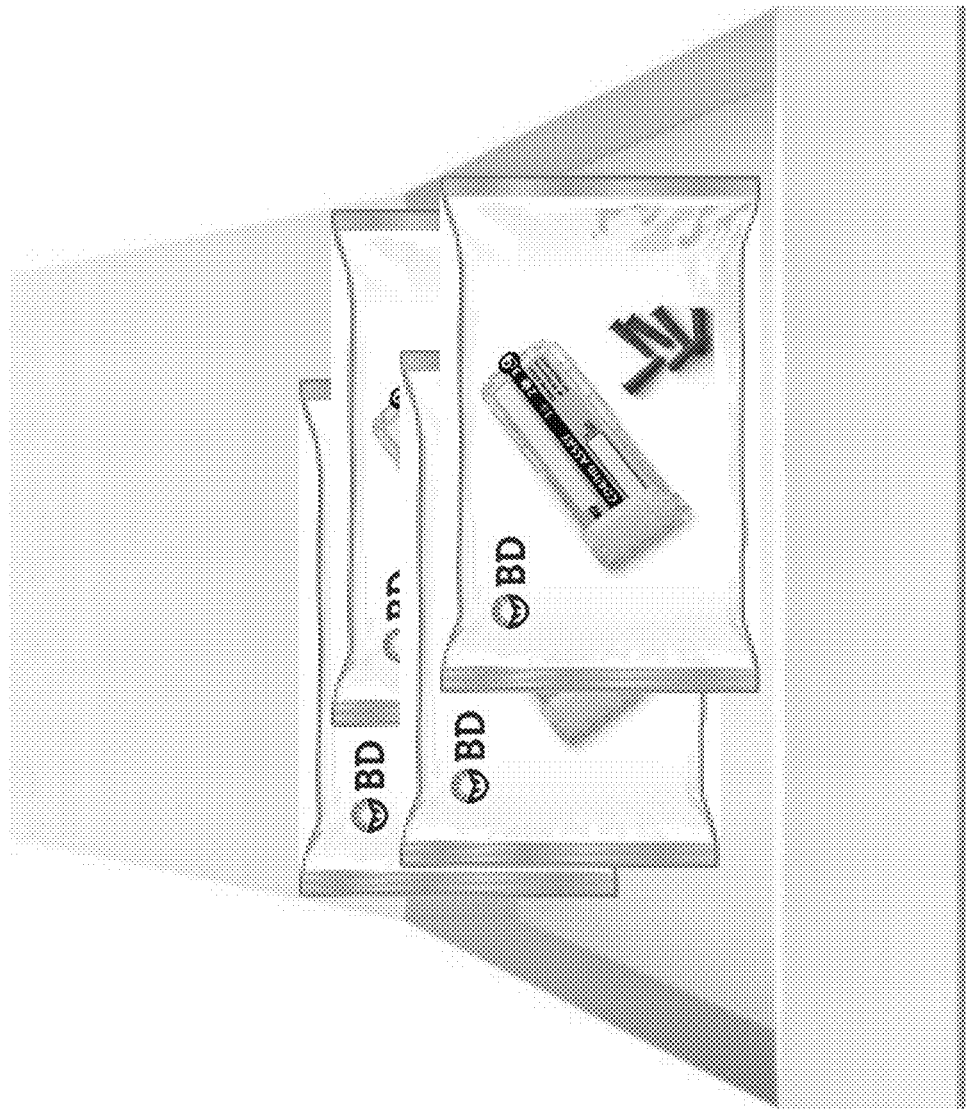
FIG. 7 shows an example of a collection of different types of kits provided together in a box according to certain embodiments.

FIG. 6 shows an example of a kit having a microfluidic cartridge packaged together with a lancet for obtaining whole blood. FIG. 7 shows an example of a collection of different types of kits, which in certain embodiments may be packaged together and provided in a box.

The various assay components of the kits may be present in separate containers, or some or all of them may be pre-combined into a reagent mixture. For example, in some instances, one or more components of the kit, e.g., the device, are present in a sealed pouch, e.g., a sterile foil pouch or envelope.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), portable flash drive, and the like, on which the information has been recorded. Yet another form of these instructions that may be present is a website address which may be used via the internet to access the information at a removed site.

Utility

Methods, systems, microfluidic cartridges and kits of the present disclosure find use in a variety of different applications and can be used to determine the presence and amount of an analyte in a large number of different sample types from a multitude of possible sources. Depending on the application and the desired output of the methods described herein, an analyte may be detected in a qualitative manner ("present" vs "absent"; "yes, above a predetermined threshold" vs "no, not above a predetermined threshold"; etc.) or a quantitative manner, e.g., as an amount in a sample (such as concentration in sample).

The subject methods and systems can be employed to characterize many types of analytes, in particular, analytes relevant to medical diagnosis or protocols for caring for a patient, including but not limited to: proteins (including both free proteins and proteins bound to surface of a structure, such as a cell), nucleic acids, viral particles, and the like. Further, samples can be from in vitro or in vivo sources, and samples can be diagnostic samples.

In practicing methods of the invention, the samples can be obtained from in vitro sources (e.g., extract from a laboratory grown cell culture) or from in vivo sources (e.g., a mammalian subject, a human subject, a research animal, etc.). In some embodiments, the sample is obtained from an in vitro source. In vitro sources include, but are not limited to, prokaryotic (e.g., bacterial) cell cultures, eukaryotic (e.g., mammalian, fungal) cell cultures (e.g., cultures of established cell lines, cultures of known or purchased cell lines, cultures of immortalized cell lines, cultures of primary cells, cultures of laboratory yeast, etc.), tissue cultures, column chromatography eluants, cell lysates/extracts (e.g., protein-containing lysates/extracts, nucleic acid-containing lysates/extracts, etc.), viral packaging supernatants, and the like. In some embodiments, the sample is obtained from an in vivo source. In vivo sources include living multi-cellular organisms and can yield diagnostic samples.

In some embodiments, the analyte is a diagnostic analyte. A "diagnostic analyte" is an analyte from a sample that has been obtained from or derived from a living multi-cellular organism, e.g., mammal, in order to make a diagnosis. In other words, the sample has been obtained to determine the presence of one or more disease analytes in order to diagnose a disease or condition. Accordingly, the methods are diagnostic methods. As the methods are "diagnostic methods," they are methods that diagnose (i.e., determine the presence or absence of) a disease (e.g., sickness, diabetes, etc.) or condition (e.g., pregnancy) in a living organism, such as a mammal (e.g., a human). As such, certain embodiments of the present disclosure are methods that are employed to determine whether a living subject has a given disease or condition (e.g., diabetes). "Diagnostic methods" also include methods that determine the severity or state of a given disease or condition.

In certain embodiments, the methods are methods of determining whether an analyte is present in a diagnostic sample. As such, the methods are methods of evaluating a sample in which the analyte of interest may or may not be present. In some cases, it is unknown whether the analyte is present in the sample prior to performing the assay. In other instances, prior to performing the assay, it is unknown whether the analyte is present in the sample in an amount that is greater than (exceeds) a predetermined threshold amount. In such cases, the methods are methods of evaluating a sample in which the analyte of interest may or may not be present in an amount that is greater than (exceeds) a predetermined threshold.

Diagnostic samples include those obtained from in vivo sources (e.g., a mammalian subject, a human subject, and the like.) and can include samples obtained from tissues or cells of a subject (e.g., biopsies, tissue samples, whole blood, fractionated blood, hair, skin, and the like). In some cases, cells, fluids, or tissues derived from a subject are cultured, stored, or manipulated prior to evaluation and such a sample can be considered a diagnostic sample if the results are used to determine the presence, absence, state, or severity of a disease (e.g., sickness, diabetes, etc.) or condition (e.g., pregnancy) in a living organism.

In some instances, a diagnostic sample is a tissue sample (e.g., whole blood, fractionated blood, plasma, serum, saliva, and the like) or is obtained from a tissue sample (e.g., whole blood, fractionated blood, plasma, serum, saliva, skin, hair, and the like). An example of a diagnostic sample includes, but is not limited to cell and tissue cultures derived from a subject (and derivatives thereof, such as supernatants, lysates, and the like); tissue samples and body fluids; non-cellular samples (e.g., column eluants; acellular biomolecules such as proteins, lipids, carbohydrates, nucleic acids; synthesis reaction mixtures; nucleic acid amplification reaction mixtures; in vitro biochemical or enzymatic reactions or assay solutions; or products of other in vitro and in vivo reactions, etc.); etc.

In some embodiments, the subject methods provide an assay for hemoglobin. As discussed above, hemoglobin may be present in any type of diagnostic sample, such as supernatants, lysates, buffered solution, as well as in biological samples including whole blood. An amount of whole blood is loaded into a sample chamber and illuminated through a slit projection module with one or more light sources, with light transmitted through the whole blood sample in the sample chamber being collected and spatially separated into component wavelengths for detection. Depending on the size of the whole blood sample, the sample chamber may be a microfluidic capillary channel sample chamber. Hemoglobin absorbance can be determined from the transmitted light at one or more wavelengths or alternatively, an entire spectrum of hemoglobin absorption may be calculated. Based on the absorbance at one or more wavelengths, the hemoglobin concentration in the whole blood sample can be determined in these embodiments of the subject methods.

In certain other instances, the subject methods provide a reagent free hemoglobin assay. As discussed above, a reagent free assay is an assay of hemoglobin which employs no reagents to interact or visualize hemoglobin in the sample. As such, hemoglobin (including derivatives such oxy-hemoglobin and carboxyhemoglobin) is assayed in its native state without reagent modification. In these instances, an unaltered whole blood sample is loaded into a sample chamber and illuminated with one or more light sources through a slit projection module, with light transmitted through the whole blood sample in the sample chamber being collected and spatially separated into component wavelengths for detection. Depending on the size of the whole blood sample, the sample chamber may be a microfluidic capillary channel sample chamber. Hemoglobin absorbance can be detected at one or more wavelengths or alternatively, an entire spectrum of hemoglobin absorption may be calculated. Based on the absorbance at one or more wavelengths, the hemoglobin concentration in the unaltered whole blood sample can be determined in these embodiments of the subject methods.

In certain other instances, the subject methods provide a hemoglobin assay on a sample also being assayed for one or more additional analytes, such as for example cell surface markers. In these embodiments, one or more reagents, including specific binding members, enzymes, substrates, oxidizers as well as binding molecules coupled to one or more fluorescent markers are contacted with the whole blood and the reagent-mixed whole blood sample is loaded into a sample chamber. The loaded sample chamber (such as a microfluidic capillary channel sample chamber) is illuminated with one or more light sources through a slit projection module, with light transmitted through the whole blood sample in the sample chamber being collected and spatially separated into component wavelengths for detection. Hemoglobin absorbance can be detected at one or more wavelengths or alternatively, an entire spectrum of hemoglobin absorption may be calculated. Based on the absorbance at one or more wavelengths, the hemoglobin concentration in the reagent-mixed whole blood sample can be determined in these embodiments of the subject methods. In conjunction with assaying for hemoglobin in the reagent-mixed sample, one or more additional analytes may be assayed. In some instances, the subject methods provide a fluorescence assay performed in conjunction with the hemoglobin absorbance assay to assay for one or more cell surface markers binding to the one or more reagents mixed into the whole blood sample. In these instances, a fluorescence light source illuminates the sample chamber loaded with reagent-mixed whole blood sample and fluorescence emission from fluorescence tags bound to target analytes is collected and spatially separated for detection.

In certain specific instances, the subject methods provide a hemoglobin assay on a sample for which is being fluorescence assayed for CD4 and % CD4. In these instances, the whole blood sample is applied to the sample application site of a microfluidic cartridge having a capillary channel sample chamber. The applied sample is carried through the inlet of the microfluidic capillary channel into a reagent mixing chamber having a porous disc for contacting the reagent mixture with the whole blood sample. The reagent mixture, in these instances, includes dried storage stable reagents CD4-PECy5, CD3-APC, CD45RA-APC and CD14-PE. The reagent mixed whole blood sample is carried by capillary action through to the sample chamber where the sample chamber is illuminated for hemoglobin assay by two light sources, a broadband white light LED and a near-infrared LED through a slit projection module which is moved laterally across the sample chamber. Light transmitted though the sample chamber is collected with an objective, magnifying lens and autofocused onto a diffraction grating to spatially separate the transmitted light on the surface of a CCD detector. The absorbance at two wavelengths, 548 nm and 675 nm are determined and the total hemoglobin absorbance accounting for scatter is calculated to assay for hemoglobin.

The reagent mixed whole blood sample in the capillary channel sample chamber is also assayed for CD4 by detecting fluorescence by fluorescent tags in the reagent mixture. CD4 may be assayed for by illuminating the reagent mixed whole blood sample in the capillary channel sample chamber with a light source and emission from the fluorescent tags in the reagent mixed whole blood sample is collected with a common objective, magnifying lens and autofocused onto the surface of the CDD detector. CD4 cell counting is then conducted by fluorescent image cytometry.

The subject methods can be employed with samples from a variety of different types of subjects. In some embodiments, a sample is from a subject within the class mammalia, including e.g., the orders carnivore (e.g., dogs and cats), rodentia (e.g., mice, guinea pigs, and rats), lagomorpha (e.g. rabbits) and primates (e.g., humans, chimpanzees, and monkeys), and the like. In certain embodiments, the animals or hosts, i.e., subjects are humans.

EXAMPLES

As can be appreciated from the disclosure provided above, the present disclosure has a wide variety of applications. Accordingly, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Those of skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Example 1

Figure 8:
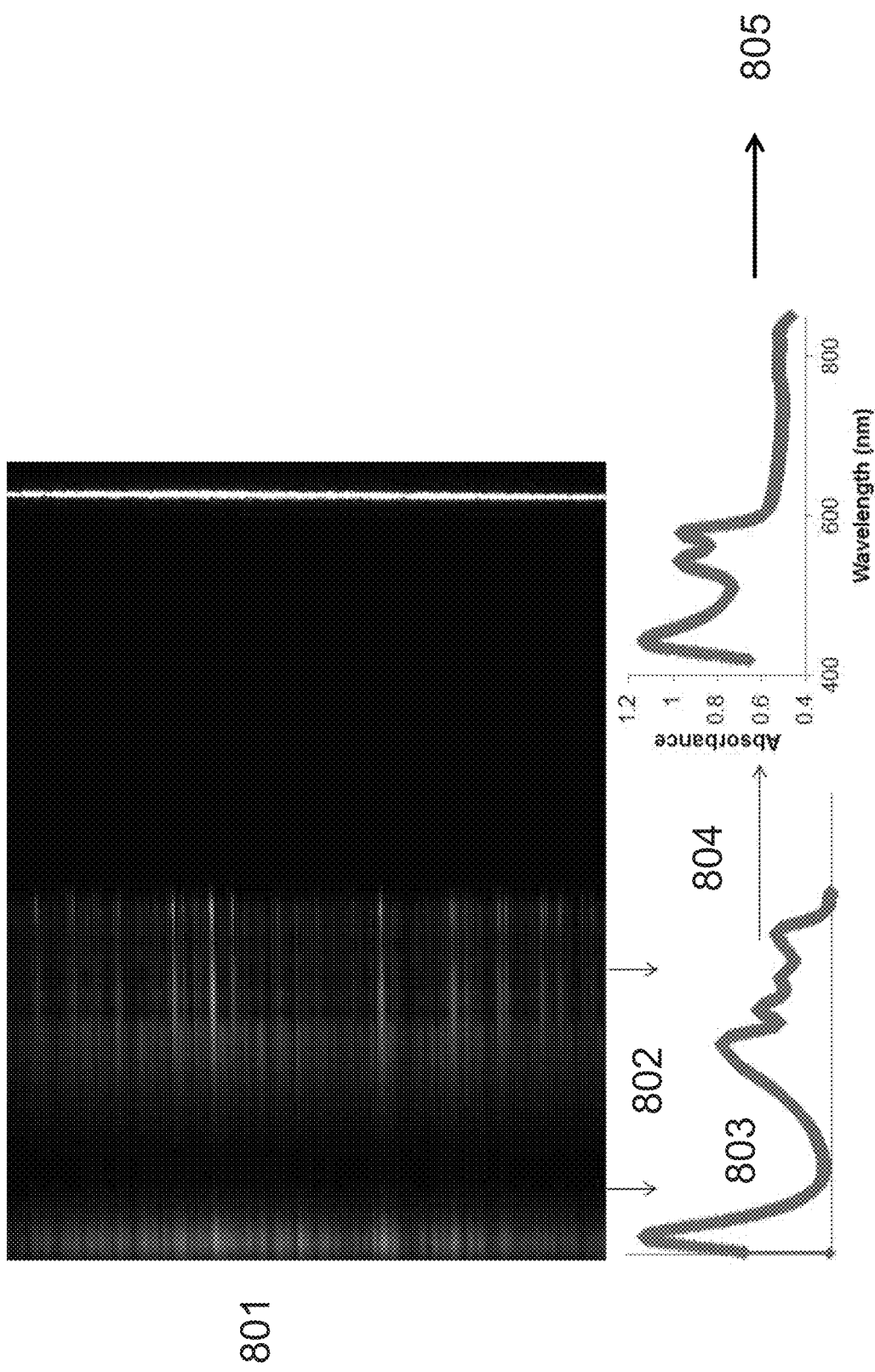
FIG. 8 shows a schematic of determining hemoglobin concentration according to certain embodiments.

A droplet (~25 µL) of whole blood sample is applied to the sample application site of a microfluidic cartridge device having a mixing chamber containing dried storage stable CD4 reagents (e.g., CD4-PECy5, CD3-APC, CD45RA-APC and CD14-PE) which are hydrated when mixed with the whole blood sample. The microfluidic cartridge device is allowed to sit until capillary action carries the reagent mixed sample into the capillary channel sample chamber. The sample chamber is illuminated by a broad spectrum LED light source (one white light LED and one near-IR LED, sequentially illuminated) with a wavelength range of 500 nm to 850 nm through a slit projection module having a slit and demagnifying lens to focus the slit-shaped beam at the surface of the sample chamber. The sample chamber is moved in a back-and-forth motion to pass light through the sample chamber which is diffracted using a diffraction grating having 300 µm spacings onto a CCD detector. FIG. 8 illustrates light detected by the CCD detector in a plot of pixel column with respect to wavelength (801) where white pixels indicate detected light. The plot at 801 is compressed into a 1-D spectrum at (802) by plotting each pixel column with respect to wavelength to detect a spectrum of transmitted light with respect to wavelength (803). Using the Beer-Lambert Law, absorbance is calculated at (804) to provide spectrum of absorbance by the sample at (805). The concentration of hemoglobin can be calculated based on the determined absorbance and the reference blank obtained during light measurement through the blank reference window on the microfluidic cartridge.

Example 2

Figure 9A:
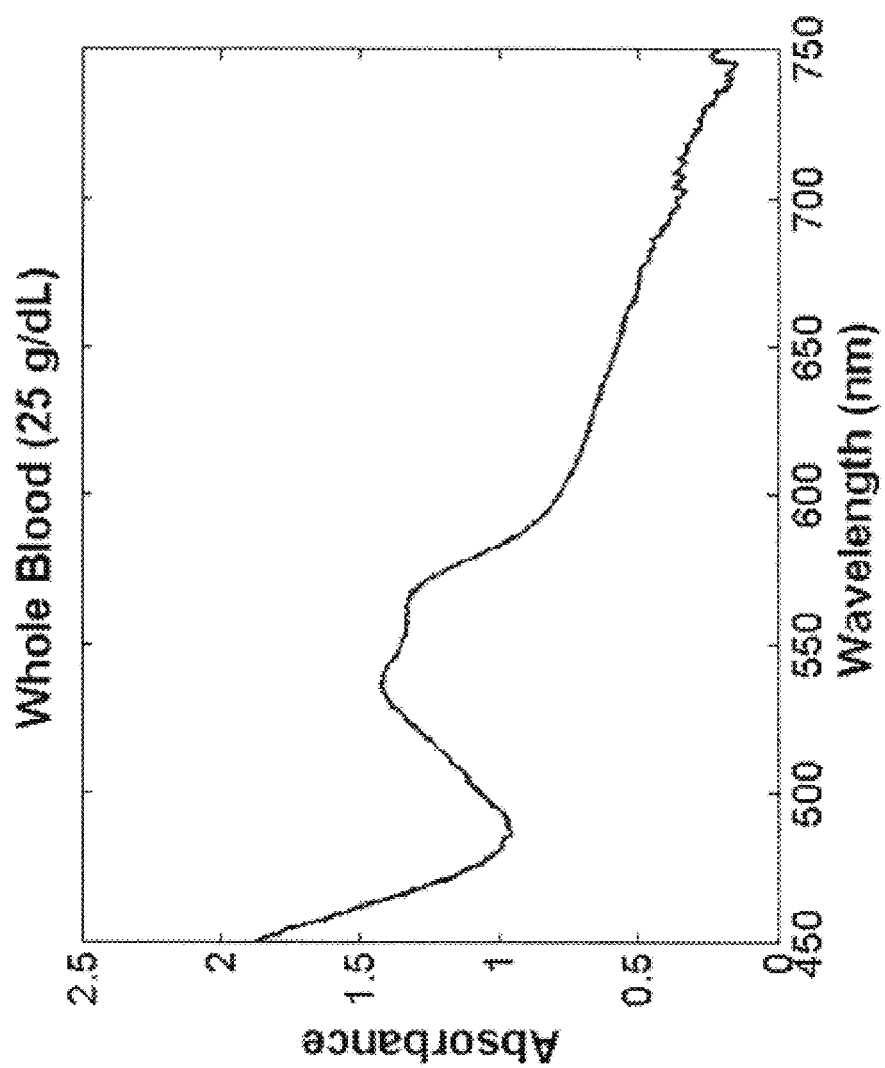
FIGS. 9a-c illustrate example hemoglobin absorbance spectra acquired by illuminating a sample chamber through a slit projection module according to certain embodiments.
Figure 9B:
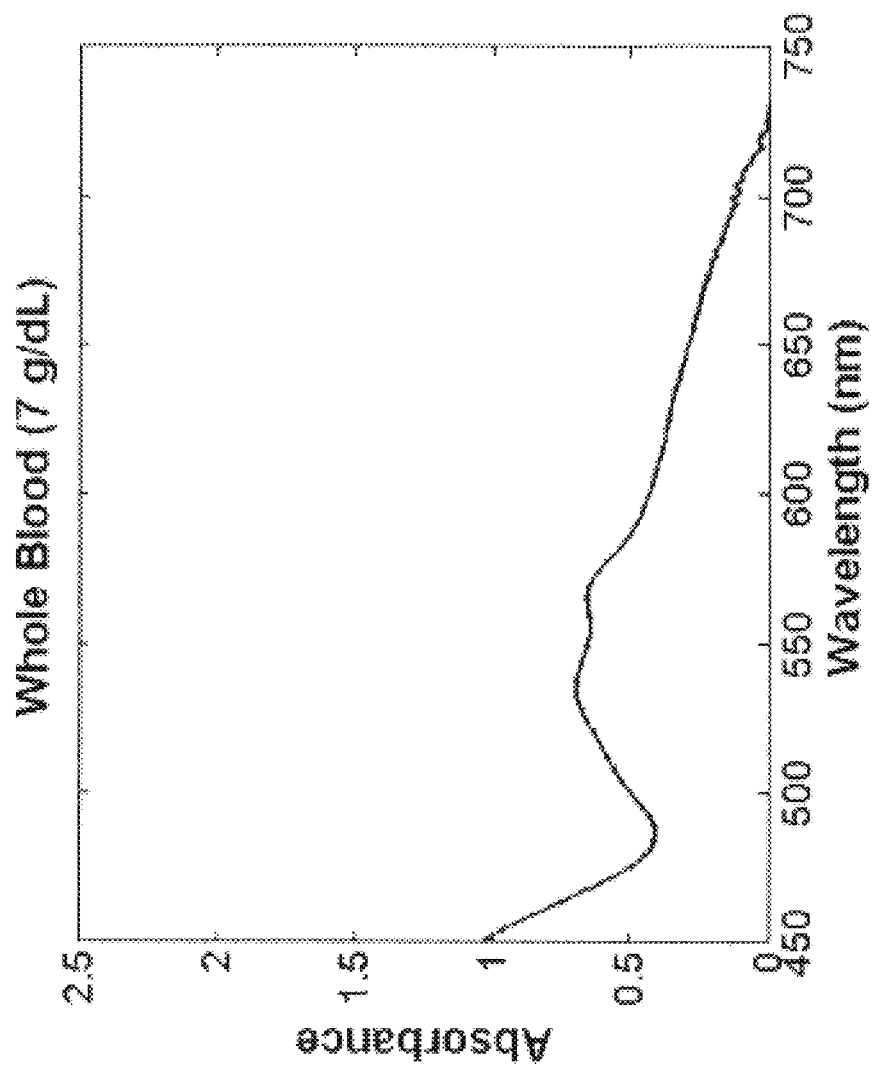
Figure 9C:
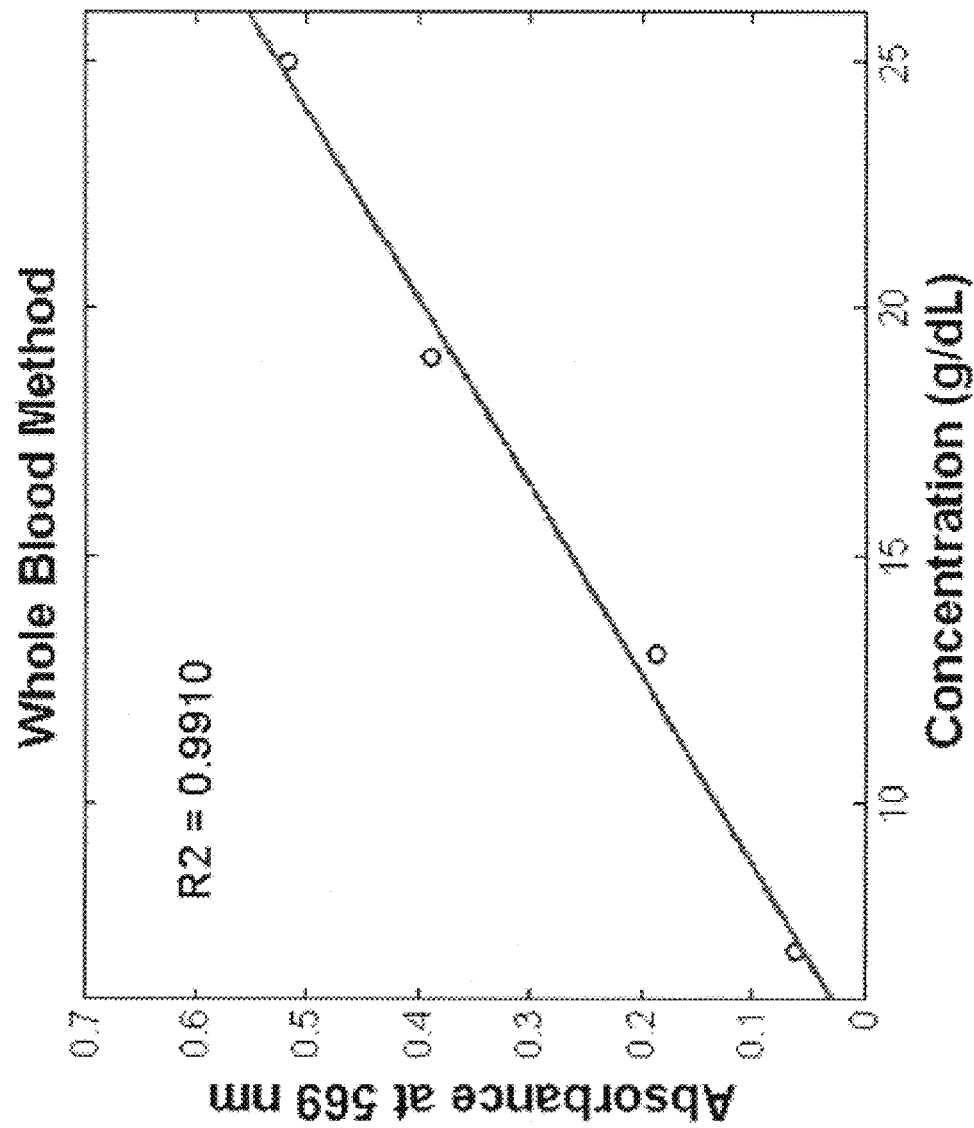

A droplet (~25 µL) of whole blood samples having either 25 g/L or 7 g/L hemoglobin is applied to the sample application site of a microfluidic cartridge device having a mixing chamber containing dried storage stable reagents. After the reagent-mixed sample reaches the capillary channel sample chamber, the sample chamber is illuminated by a broad spectrum LED light source (one white light LED and one near-IR LED, sequentially illuminated) with a wavelength range of 500 nm to 850 nm through a slit projection module having a slit and demagnifying lens to focus the slit-shaped beam at the surface of the sample chamber. The sample chamber is moved passing light through the sample chamber which is diffracted using a diffraction grating onto a CCD detector. Pixel plots from the CCD detector are compressed to a one-dimensional spectrum of transmitted light with respect to wavelength. Using the Beer-Lambert Law, absorbance spectra were calculated from the spectra of transmitted light. FIG. 9a shows absorbance spectra of hemoglobin in whole blood at a concentration of 25 g/dL. FIG. 9b shows absorbance spectra of hemoglobin in whole blood at a concentration of 7 g/dL. The absorbance at 569 nm was determined at each concentration of hemoglobin from the obtained spectra. The protocol was repeated with whole blood samples having hemoglobin concentrations of 3 g/dL, 13 g/dL, 19 g/dL and absorbance at 569 nm for each of the whole blood samples was plotted with respect to concentration. FIG. 9c illustrates a linear relationship between hemoglobin concentration and absorbance at 569 nm indicating that measurements using the slit-projection module can be used over a wide range of hemoglobin concentrations.

Example 3

Figure 10:
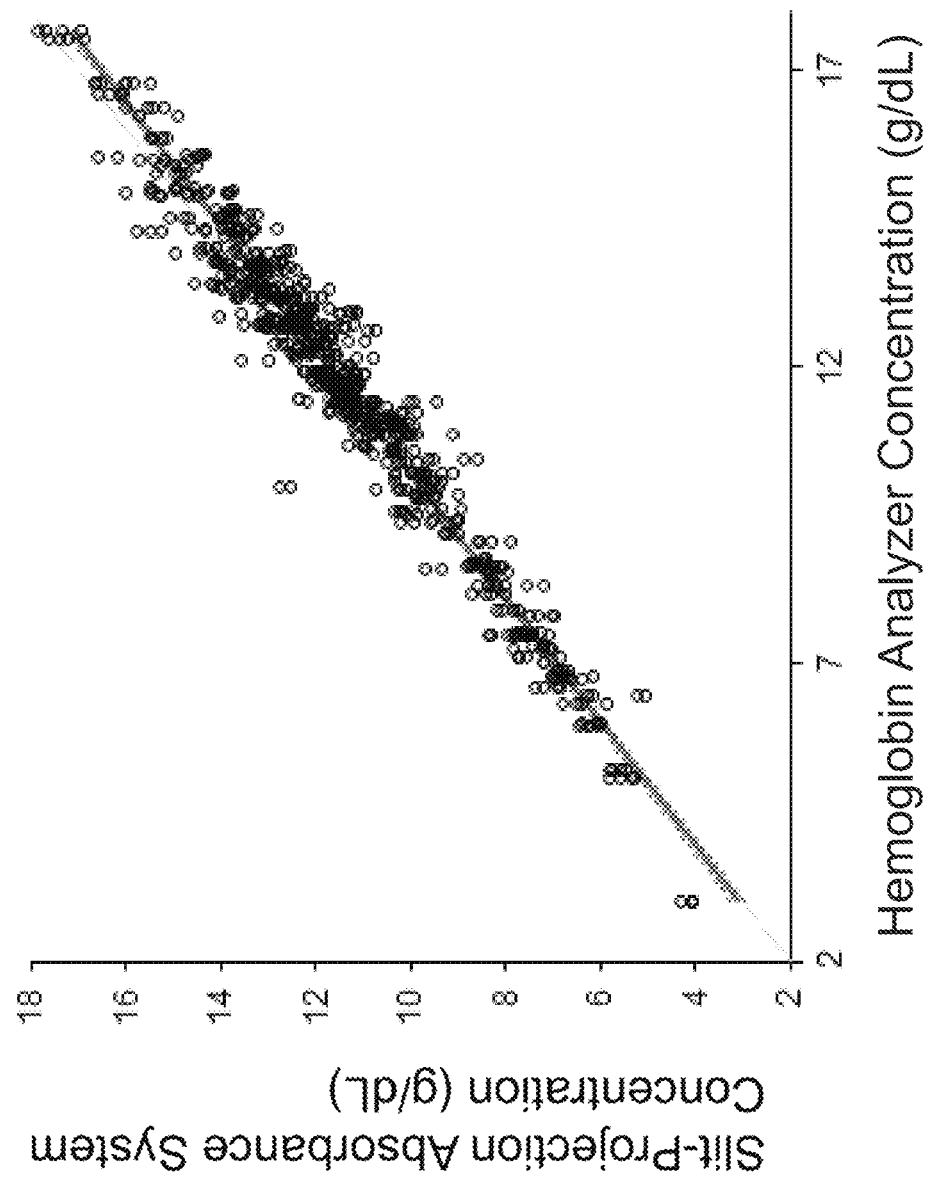
FIG. 10 illustrates a comparison of hemoglobin measurement in whole blood with methods according to certain embodiments and a hematology analyzer.

120 fresh HIV+ patient whole blood samples (both venipuncture and fingerstick samples) were analyzed using a Sysmex XS-1000i automated hematology system to determine concentration of hemoglobin in the whole blood samples. In conjunction, each sample was applied to the sample application site of a separate microfluidic cartridge device having a mixing chamber containing dried storage stable CD4 assay reagents. The sample chamber of each of the 120 microfluidic cartridge devices were illuminated by a broad spectrum LED light source (one white light LED and one near-IR LED, sequentially illuminated) with a wavelength range of 500 nm to 850 nm through a slit projection module having a slit and demagnifying lens to focus the slit-shaped beam at the surface of the sample chamber. The sample chamber is moved through the slit-shaped beam passing light through the sample chamber which is diffracted using a diffraction grating onto a CCD detector. Pixel plots from the CCD detector are compressed to a one-dimensional spectrum of transmitted light with respect to wavelength. Using the Beer-Lambert Law, absorbance spectra were calculated from the spectra of transmitted light. Concentration of hemoglobin for each sample was calculated using absorbance at 548 nm and corrected for scatter by measuring absorbance at 650 nm or 675 nm FIG. 10 shows a plot of the hemoglobin concentration as determined using the absorbance assay described herein and hemoglobin concentration determined using the Sysmex XS-1000i automated hematology system. As shown in FIG. 10, there is a strong linear relationship between the hemoglobin concentrations determined using the subject methods as compared to the hematology analyzer. This shows that the subject methods are suitable for providing clinically accurate concentrations of hemoglobin in whole blood (venipuncture or fingerstick).

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of assaying a sample for an analyte, the method comprising:
    illuminating a sample in a sample chamber with light from a light source that is propagated along an optical axis through a slit projection module to provide a slit-shaped beam on the sample chamber;
    detecting light transmitted through the sample, wherein the light does not deviate substantially from the optical axis prior to detection; and
    calculating absorbance of the detected light at one or more wavelengths to assay the sample for the analyte in the sample.

2. The method according to claim 1, wherein the method further comprises calculating absorbance of detected light at one or more wavelengths to compensate for scatter by the sample.

3. The method according to claim 1, wherein the sample is illuminated with one or more broad spectrum light sources.

4. The method according to claim 1, wherein the broad spectrum light source comprises a visible light source and a near infrared light source.

5. The method according to claim 1, wherein the sample chamber is moved in a manner sufficient to displace the slit shaped beam along the length of the sample chamber in discrete increments.

6. The method according to claim 1, wherein spatially separating wavelengths of light comprises diffracting light with a diffraction grating.

7. The method according to claim 1, wherein the method further comprises illuminating a blank reference window.

8. The method according to claim 1, wherein the method further comprises projecting a non-diffracted image of the slit on a detector.

9. The method according to claim 7, wherein the method comprises using the non-diffracted image of the slit for calibration.

10. The method according to claim 9, wherein absorbance is calculated at a wavelength between 500 nm and 600 nm.

11. The method according to claim 1, wherein the analyte is hemoglobin.

12. A method comprising:
    providing a system for assaying a sample for an analyte, the system comprising:
        a broad spectrum light source;
        a slit projection module coupled to the broad spectrum light source, wherein the slit projection module comprises:
            a slit that narrows a beam of light from the broad spectrum light source to a width equal to the width of the slit; and
            a focusing lens that focuses light from the slit;
        a cartridge holder configured to receive a microfluidic device having a capillary channel sample chamber; and
        a detector for detecting one or more predetermined wavelengths of the transmitted light;
    positioning the microfluidic device into the cartridge holder such that light from the broad spectrum light source is propagated along an optical axis and is transmitted through the slit projection module, sample chamber and to the detector without substantial diversion from the optical axis;
    illuminating a sample in a sample chamber with a light source through a slit projection module to provide a slit-shaped beam on the sample chamber;
    detecting light transmitted through the sample; and
    calculating absorbance of the detected light at one or more wavelengths to assay the sample for the analyte in the sample.

13. The method according to claim 12, wherein the sample has a volume of between 1 μL and 100 μL.

14. The method according to claim 12, wherein positioning the microfluidic device into the cartridge holder comprises sliding the microfluidic device into the interior of the system.

15. The method according to claim 12, wherein the cartridge holder is configured to slide out of the system to receive the microfluidic device.

16. The method according to claim 12, wherein the method further comprises calculating absorbance of detected light at one or more wavelengths to compensate for scatter by the sample.

17. The method according to claim 12, wherein the method comprises calculating absorbance of detected light at a wavelength of 700 nm or less to compensate for scatter by the sample.

18. The method according to claim 17, wherein the method comprises calculating absorbance of detected light at 650 nm to compensate for scatter by the sample.

19. The method according to claim 12, wherein the sample is illuminated with one or more broad spectrum light sources.

* * * * *